United States Patent
Wu et al.

(10) Patent No.: US 9,365,572 B2
(45) Date of Patent: Jun. 14, 2016

(54) PI3K AND/OR MTOR INHIBITOR

(71) Applicant: XUANZHU PHARMA CO., LTD., Jinan (CN)

(72) Inventors: Frank Wu, Jinan (CN); Chutian Shu, Jinan (CN)

(73) Assignee: Xuanzhu Pharma Co., Ltd., Jinan, Shandong Province (CN)

( * ) Notice: Subject to any disclaimer, the term of this patent is extended or adjusted under 35 U.S.C. 154(b) by 0 days.

(21) Appl. No.: 14/427,665

(22) PCT Filed: Sep. 12, 2013

(86) PCT No.: PCT/CN2013/001061
§ 371 (c)(1),
(2) Date: Mar. 12, 2015

(87) PCT Pub. No.: WO2014/040373
PCT Pub. Date: Mar. 20, 2014

(65) Prior Publication Data
US 2015/0239885 A1    Aug. 27, 2015

(30) Foreign Application Priority Data
Sep. 12, 2012  (CN) .......................... 2012 1 0334795

(51) Int. Cl.
| C07D 471/14 | (2006.01) |
| A61K 31/519 | (2006.01) |
| A61K 45/00 | (2006.01) |
| C07D 519/00 | (2006.01) |
| A61K 31/5377 | (2006.01) |
| A61K 45/06 | (2006.01) |

(52) U.S. Cl.
CPC ............ C07D 471/14 (2013.01); A61K 31/519 (2013.01); A61K 31/5377 (2013.01); A61K 45/06 (2013.01); C07D 519/00 (2013.01)

(58) Field of Classification Search
CPC ............. C07D 471/14; A61K 2300/00; A61K 31/519; A61K 45/00
See application file for complete search history.

(56) References Cited

FOREIGN PATENT DOCUMENTS

| CN | 102256966 | * 11/2011 | ........... C07D 401/14 |
| CN | 102399218 |   4/2012 | |
| CN | 102399220 | *  4/2012 | ........... A61K 31/519 |
| WO | 2010044885 |   4/2010 | |

OTHER PUBLICATIONS

West, Anthony R., Solid State Chemistry and Its Applications, Wiley, New York, 1988, 358.*
Liu et al., "Discovery of 9-(6-Aminopyridin-3-yl)-1-(3-(trifluoromethyl)-phenyl)benzo[h][1,6]naphthyridin-2(1H)-one (Torin2) as a Potent, Selective, and Orally Available Mammalian Target of Rapamycin (mTOR) Inhibitor for Treatment of Cancer", J Med Chem. Mar. 10, 2011; 54(5): 1473-1480.
International Application No. PCT/CN2013/001061, International Search Report dated Dec. 19, 2013.
Chinese Patent Application No. 201380047494.2, Office Action issued Jan. 6, 2016, 5 pages.
European Patent Application No. 13836950.9, Extended European Search Report, mailed Feb. 11, 2016, 7 pages.

* cited by examiner

*Primary Examiner* — Erich A Leeser
(74) *Attorney, Agent, or Firm* — Kilpatrick Townsend & Stockton LLP

(57) ABSTRACT

The present invention relates to a compound of formula (I), or a pharmaceutically acceptable salt, a stereoisomer or a solvate thereof, wherein $R^1$, $R^2$, $R^3$, $R^4$, X, Y, A and B are as defined in the specification. The present invention further relates to a method for preparing these compounds, a pharmaceutical composition containing these compounds, and a use of these compounds in manufacture of a medicament for treating and/or preventing proliferative diseases.

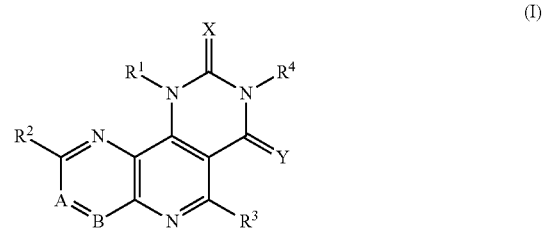

9 Claims, No Drawings

PI3K AND/OR MTOR INHIBITOR

PRIOR RELATED APPLICATIONS

This application is a National Phase application of International Application No. PCT/CN2013/001061, filed Sep. 12, 2013, which claims priority to the Chinese application of No. 201210334795.0, filed on Sep. 12, 2012, which are both incorporated herein by reference in their entireties. The contents of all the documents cited herein constitute a part of the present application.

The present application claims priority to the Chinese application of No. 201210334795.0, filed on Sep. 12, 2012, which is incorporated herein as a whole by reference. The contents of all the documents cited herein constitute a part of the present application.

TECHNICAL FIELD

The present invention relates to phosphatidylinositol 3-kinase (PI3K) and/or mammalian target protein of rapamycin (mTOR) inhibitors or a pharmaceutically acceptable salt, a stereoisomer or a solvate thereof, a method for preparing these compounds, a pharmaceutical composition comprising the same, as well as a use of these compounds in manufacture of a medicament for treating and/or preventing proliferative diseases.

BACKGROUND

Tumors are new creatures formed in the body due to actions of a variety of oncogenic factors and the following changes of genetic material of cells resulting in abnormal gene expression and cell proliferation. The tumor cells lose their normal growth regulatory function and have autonomous or relatively autonomous growth ability. The tumor cells can continue to grow even the oncogenic factors disappear and will cause a consumption of large quantities of human's nutrients. If not being found and treated early, the cancer cells will be transferred and grow throughout the body, and release a variety of toxins that cause the body weight loss, anemia, organ failure and even death.

The method of treating tumors mainly includes three aspects: drug therapy, surgery and radiation therapy. Drug therapy is becoming increasingly important in cancer treatment since surgery and radiation therapy are difficult to eradicate the tumor and fail to show obvious effect in patients with the mid-advanced cancer.

Conventional anticancer drugs do not distinguish between tumor cells and normal cells, and often cause serious side effects. Targeted drugs specifically target to cancer cells and can accurately act on the tumor, which greatly improves the level of treatment and reduces the adverse response rate, such as making the median survival time of patients with advanced colorectal cancer increased 66.7%, and the efficiency of the treatment of advanced breast cancer increased 71.3%.

As pharmaceutical companies are accelerating the development of targeted antineoplastic drugs, and there is a great market demand for this class of antineoplastic drugs, molecular targeted drugs have become the world's fastest growing unit in the worldwide market. PI3K pathway is the most common place where human cancer cells mutate, and it can lead to cell proliferation, activation and signal amplification. PI3K and mTOR are important kinases of PI3K signaling pathway.

PI3K is a member of lipid kinase family, it regulates cell metabolism and growth through phosphorylation at 3-position of phosphatidylinositol to produce phosphatidylinositol-triphosphate (PIP3). This PIP3, which is the second messenger of lipid, can make PI3K paired with downstream effectors (especially Akt), resulting in membrane recruitment and phosphorylation, cell proliferation and activation. Therefore, inhibition of phosphatidylinositol 3-kinase can affect the PI3K pathway, thereby inhibiting cancer cell proliferation and activation.

mTOR is a serine/threonine protein kinase present in the cytoplasm, it belongs to the phosphoinositide 3-kinase-related protein kinase family and exists in organism as two complexes forms, namely mTORC1 (rapamycin target) and mTORC2 (not inhibited by rapamycin). mTOR is a cellular signal transduction protein, which regulates the response of tumor cells to nutrients and growth factors, and controls tumor blood supply through the role of vascular endothelial growth factor. mTOR inhibitors can make cancer cells starved, and reduce the tumor volume by inhibiting mTOR.

Now PI3K and/or mTOR inhibitors have been developed as medicament, but no inhibitor goes to the market. The prior art literature, Journal of Medicinal Chemistry (2011), 54(5), 1473-1480, "Discovery of 9-(6-Aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer, discloses a compound named as Torin2 and reports the study result about its in vivo pharmacokinetics.

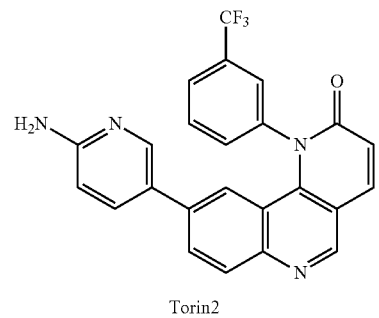 [SMILES: Nc1ccc(-c2ccc3ncc4ccc(=O)n(-c5cccc(C(F)(F)F)c5)c4c3c2)cn1]

Torin2

For the study of the kinase inhibitor (including PI3K and/or mTOR inhibitors), a great attention should be paid to the selectivity on the kinase target. Since the kinase has a high homology, a small compound can inhibit other kinase targets while it inhibits PI3K and/or mTOR. These kinases play important roles in the biosignal conduction. Once they are inhibited, the signal conduction disorder will appear, showing the harmful adverse effect or toxicity to the body. Therefore, it is urgently needed for the PI3K and/or mTOR kinase to develop the kinase inhibitor having good selectivity.

Besides the kinase selectivity, the selectivity on other non-kinase target is also significant. The non-kinase targets such as ion channel and various acceptors are also important for the physiological process such as the signal conduction and the neurotransmitter release. Once these non-kinase targets are inhibited, the body will have metabolic disturbance and physiological function impairment, which can bring a serious influence on the safety of the patient.

In summary, it becomes a hotspot in the current study of antitumor drug to develop a compound having a high selectivity on PI3K and/or mTOR, a good inhibitory activity and a good pharmacokinetics.

SUMMARY OF THE INVENTION

The object of the present invention is to provide a PI3K and/or mTOR inhibitor. Specifically, the present invention relates to:

(I) A compound of formula (I), or a pharmaceutically acceptable salt, a stereoisomer or a solvate thereof:

$$\text{(I)}$$

X and Y are each independently O or S;
A and B are each independently $CR^6$, $R^6$ is hydrogen, halogen, cyano, hydroxy, carboxyl, —$(CH_2)_nNR^{8a}R^{8b}$, —$(CH_2)_nC(O)R^9$, —$(CH_2)_nS(O)_mR^9$, —$(CH_2)_n S(O)_mNR^{8a}R^{8b}$, —$(CH_2)_nN(R^{8a})S(O)_mR^9$, —$(CH_2)_nC(O)NR^{8a}R^{8b}$, —$(CH_2)_nOC(O)R^9$, —$(CH_2)_nC(O)(CH_2)_nOR^9$, —$(CH_2)_nN(R^{8a})C(O)R^9$, $C_{1-6}$alkyl or $C_{1-6}$alkoxy, wherein $C_{1-6}$alkyl and $C_{1-6}$alkoxy may be optionally substituted with 1-3 substituents selected from halogen, hydroxy and carboxyl;
$R^1$ is hydrogen, $C_{1-6}$alkyl, $C_{2-8}$alkenyl, $C_{2-8}$alkynyl, $C_{3-8}$ cycloalkyl, 6- to 14-membered aryl, 5- to 14-membered heteroaryl, 3- to 14-membered heterocyclic group, 7- to 12-membered spirocyclic group, or 7- to 12-membered bridge group, all of which except hydrogen may be optionally substituted with 1-5 $R^{7a}(s)$;
$R^2$ is hydrogen, $C_{1-6}$alkyl, $C_{2-8}$alkenyl, $C_{2-8}$alkynyl, $C_{3-8}$cycloalkyl, 6- to 14-membered aryl, 5- to 14-membered heteroaryl, 3- to 14-membered heterocyclic group, 7- to 12-membered spirocyclic group, or 7- to 12-membered bridge group, all of which except hydrogen may be optionally substituted with 1-5 $R^{7b}(s)$;
$R^3$ is hydrogen, carboxyl, or $C_{1-6}$alkyl, wherein $C_{1-6}$alkyl may be optionally substituted with 1-3 substituents selected from halogen, hydroxy and carboxyl;
$R^4$ is hydrogen, $C_{3-8}$ cycloalkyl, $C_{1-6}$alkyl, wherein $C_{1-6}$alkyl may be optionally substituted with 1-3 substituents selected from halogen, hydroxy and carboxyl;
$R^{7a}$ and $R^{7b}$ are each independently
(1) halogen, cyano, hydroxy, —$(CH_2)_nNR^{8a}R^{8b}$, —$(CH_2)_nC(O)R^9$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nC(O)NR^{8a}R^{8b}$, —$(CH_2)_nOC(O)R^9$, —$(CH_2)_nC(O)(CH_2)_nOR^9$, or —$(CH_2)_nN(R^{8a})C(O)R^9$,
(2) $C_{1-6}$alkyl, $C_{2-8}$alkenyl, $C_{2-8}$alkynyl, or $C_{1-6}$alkoxy, all of which may be optionally substituted with 1-3 substituents selected from halogen, hydroxy, and cyano; or
(3) $C_{3-8}$cycloalkyl, 6- to 14-membered aryl, 5- to 14-membered heteroaryl, or 3- to 14-membered heterocyclic group, all of which may be optionally substituted with 1-3 substituents selected from halogen, hydroxy, cyano, trifluoromethyl, $C_{1-6}$alkyl, $C_{2-8}$alkenyl, $C_{2-8}$alkynyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nOC(O)R^9$, and —$(CH_2)_nN(R^{8a})C(O)R^9$;
$R^{8a}$ and $R^{8b}$ are each independently hydrogen, $C_{1-6}$alkyl, $C_{3-8}$ cycloalkyl, 6- to 14-membered aryl, 5- to 14-membered heteroaryl, or 3- to 14-membered heterocyclic group, all of which except hydrogen may be optionally substituted with 1-3 substituents selected from hydroxy, halogen, cyano, carboxyl, —$(CH_2)_nNR^{8a}R^{8b}$, sulfamoyl, carbamoyl, and sulfamino;
$R^9$ is hydrogen $C_{1-6}$alkyl, or $C_{1-6}$alkoxy, all of which except hydrogen may be optionally substituted with 1-3 substituents selected from halogen, cyano, hydroxy, carboxyl, —$(CH_2)_nNR^{8a}R^{8b}$, sulfamoyl, and carbamoyl;
m is 0, 1 or 2; and
n is 0-4.

(II) The compound of the above (I), or a pharmaceutically acceptable salt, a stereoisomer or a solvate thereof, wherein,
A and B are each independently $CR^6$, wherein $R^6$ is hydrogen, —$(CH_2)_nS(O)_mNR^{8a}R^{8b}$, —$(CH_2)_nN(R^{8a})S(O)_mR^9$, —$(CH_2)_nC(O)NR^{8a}R^{8b}$, $C_{1-6}$alkyl or $C_{1-6}$alkoxy, wherein $C_{1-6}$alkyl and $C_{1-6}$alkoxy may be optionally substituted with 1-3 substituents selected from halogen, hydroxy and carboxyl;
$R^1$ is $C_{3-8}$cycloalkyl, 6- to 10-membered aryl, 5- to 10-membered heteroaryl, or 5- to 10-membered heterocyclic group, all of which may be optionally substituted with 1-3 $R^{7a}(s)$;
$R^2$ is $C_{3-8}$cycloalkyl, 6- to 10-membered aryl, 5- to 10-membered heteroaryl, or 5- to 10-membered heterocyclic group, all of which may be optionally substituted with 1-3 $R^{7b}(s)$;
$R^3$ and $R^4$ are each independently hydrogen or $C_{1-6}$alkyl, wherein $C_{1-6}$alkyl may be optionally substituted with 1-3 substituents selected from halogen, hydroxy and carboxyl;
$R^{7a}$ and $R^{7b}$ are each independently
(1) halogen, cyano, hydroxy, —$(CH_2)_nNR^{8a}R^{8b}$, —$(CH_2)_nC(O)R^9$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nC(O)NR^{8a}R^{8b}$, —$(CH_2)_nOC(O)R^9$, —$(CH_2)_nC(O)(CH_2)_nOR^9$, or —$(CH_2)_nN(R^{8a})C(O)R^9$,
(2) $C_{1-6}$alkyl or $C_{1-6}$alkoxy, both of which may be optionally substituted with 1-3 substituents selected from halogen, hydroxy and cyano, or
(3) $C_{3-8}$cycloalkyl, 6- to 10-membered aryl, 5- to 10-membered heteroaryl or 5- to 10-membered heterocyclic group, all of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nOC(O)R^9$, and —$(CH_2)_nN(R^{8a})C(O)R^9$;
$R^{8a}$ and $R^{8b}$ are each independently hydrogen or $C_{1-6}$alkyl, wherein $C_{1-6}$alkyl may be optionally substituted with 1-3 substituents selected from hydroxy, halogen, cyano, carboxyl, sulfamoyl, carbamoyl, and sulfamino;
$R^9$ is hydrogen or $C_{1-6}$alkyl, wherein $C_{1-6}$alkyl may be optionally substituted with 1-3 substituents selected from halogen, cyano, hydroxy, carboxyl, —$NR^{8a}R^{8b}$, sulfamoyl, and carbamoyl;
m is 0, 1 or 2; and
n is 0-4.

(III) The compound of the above (II), or a pharmaceutically acceptable salt, a stereoisomer or a solvate thereof, wherein,
X and Y are each O;
A and B are each CH;
$R^1$ is 6- to 10-membered aryl, 5- to 6-membered monocyclic heteroaryl, 9- to 10-membered fused heteroaryl, 5- to 6-membered monocyclic heterocyclic group, or 9- to 10-membered fused heterocyclic group, all of which may be optionally substituted with 1-3 $R^{7a}(s)$;
$R^2$ is 6- to 10-membered aryl, 5- to 6-membered monocyclic heteroaryl, 9- to 10-membered fused heteroaryl, 5- to 6-membered monocyclic heterocyclic group, or 9- to 10-membered fused heterocyclic group, all of which may be optionally substituted with 1-3 $R^{7b}(s)$;
$R^3$ is hydrogen;

$R^4$ is hydrogen or $C_{1-6}$alkyl, wherein $C_{1-6}$alkyl may be optionally substituted with 1-3 substituents selected from halogen, hydroxy and carboxyl;

$R^{7a}$ and $R^{7b}$ are each independently (1) halogen, cyano, hydroxy, —$(CH_2)_nNR^{8a}R^{8b}$, —$(CH_2)_nC(O)R^9$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nC(O)NR^{8a}R^{8b}$, —$(CH_2)_nOC(O)R^9$, —$(CH_2)_nC(O)(CH_2)_nOR^9$, —$(CH_2)_nN(R^{8a})C(O)R^9$, (2) $C_{1-6}$alkyl or $C_{1-6}$alkoxy, both of which may be optionally substituted with 1-3 substituents selected from halogen, hydroxy and cyano, or (3) 5- to 10-membered heteroaryl or 5- to 10-membered heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nS(O)_mR^9$, —$(CH_2)_nS(O)_mNR^{8a}R^{8b}$, —$(CH_2)_nN(R^{8a})S(O)_mR^9$, —$(CH_2)_nOC(O)R^9$, and —$(CH_2)_nN(R^{8a})C(O)R^9$;

$R^{8a}$ and $R^{8b}$ are each independently hydrogen or $C_{1-6}$alkyl;

$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;

m is 0, 1 or 2; and n is 0-3.

In a further preferable embodiment according to the compound of formula (I) of the present invention:

X and Y are each O;

A and B are each CH;

$R^1$ is 6- to 10-membered aryl or 5- to 6-membered monocyclic heteroaryl, both of which may be optionally substituted with 1-3 $R^{7a}$(s);

$R^2$ is 6- to 10-membered aryl, 5- to 6-membered monocyclic heteroaryl, or 9- to 10-membered fused heteroaryl, all of which may be optionally substituted with 1-3 $R^{7b}$(s);

$R^3$ is hydrogen;

$R^4$ is hydrogen or $C_{1-6}$alkyl, wherein $C_{1-6}$alkyl may be optionally substituted with hydroxy;

$R^{7a}$ and $R^{7b}$ are each independently (1) halogen, cyano, hydroxy, —$(CH_2)_nNR^{8a}R^{8b}$, —$(CH_2)_nC(O)R^9$, —$(CH_2)_nS(O)_mR^9$, —$(CH_2)_nC(O)NR^{8a}R^{8b}$, —$C(O)(CH_2)_nOR^9$, or —$(CH_2)_nN(R^{8a})C(O)R^9$, (2) $C_{1-6}$alkyl or $C_{1-6}$alkoxy, both of which may be optionally substituted with 1-3 substituents selected from halogen, hydroxy and cyano, or (3) 5- to 6-membered monocyclic heteroaryl or 5- to 6-membered monocyclic heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nOC(O)R^9$, and —$(CH_2)_nN(R^{8a})C(O)R^9$;

$R^{8a}$ and $R^{8b}$ are each independently hydrogen or $C_{1-6}$alkyl;

$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;

m is 0, 1 or 2; and n is 0-3.

In a further preferable embodiment according to the compound of formula (I) of the present invention:

X and Y are each O;

A and B are each CH;

$R^1$ is phenyl, pyridyl, or pyrimidyl, all of which may be optionally substituted with 1-3 $R^{7a}$(s);

$R^2$ is phenyl, pyridyl, pyrimidyl, thienyl, pyrazolyl, indazolyl, indolyl, pyridopyrrolyl, pyrazolylpyridyl, or quinolyl, all of which may be optionally substituted with 1-3 $R^{7b}$(s);

$R^3$ is hydrogen;

$R^4$ is hydrogen, methyl, ethyl or hydroxymethyl;

$R^{7a}$ and $R^{7b}$ are each independently (1) cyano, hydroxy, —$NR^{8a}R^{8b}$, —$C(O)R^9$, —$S(O)_mR^9$, —$C(O)NR^{8a}R^{8b}$, —$C(O)(CH_2)_nOR^9$, or —$N(R^{8a})C(O)R^9$, (2) $C_{1-6}$alkyl or $C_{1-6}$alkoxy, both of which may be optionally substituted with 1-3 substituents selected from halogen, hydroxy and cyano, or (3) pyrrolyl, pyrazolyl, imidazolyl, piperidyl, piperazinyl, or morpholinyl, all of which may be optionally substituted with 1-3 substituents selected from halogen, hydroxy, cyano, trifluoromethyl, $C_{1-6}$alkyl, $C_{1-6}$alkoxy, —$NR^{8a}R^{8b}$, —$C(O)R^9$, —$C(O)NR^{8a}R^{8b}$, —$OC(O)R^9$, and —$N(R^{8a})C(O)R^9$;

$R^{8a}$ and $R^{8b}$ are each independently hydrogen or $C_{1-6}$alkyl;

$R^9$ is hydrogen or $C_{1-6}$alkyl, wherein $C_{1-6}$alkyl may be optionally substituted with 1-3 substituents selected from halogen, cyano, and hydroxy;

m is 0, 1 or 2.

(IV) The compound of the above (III), or a pharmaceutically acceptable salt, a stereoisomer or a solvate thereof, wherein, X and Y are each O;

A and B are each CH;

$R^1$ is 5- to 6-membered monocyclic heterocyclic group, which may be optionally substituted with 1-3 $R^{7a}$(s);

$R^2$ is 6- to 10-membered aryl, 5- to 6-membered monocyclic heteroaryl, or 9- to 10-membered fused heteroaryl, all of which may be optionally substituted with 1-3 $R^{7b}$(s);

$R^3$ is hydrogen;

$R^4$ is hydrogen, methyl, or hydroxymethyl;

$R^{7a}$ and $R^{7b}$ are each independently (1) cyano, hydroxy, —$(CH_2)_nNR^{8a}R^{8b}$, —$(CH_2)_nC(O)R^9$, —$(CH_2)_nS(O)_mR^9$, —$(CH_2)_nC(O)NR^{8a}R^{8b}$, —$C(O)(CH_2)_nOR^9$, or —$(CH_2)_nN(R^{8a})C(O)R^9$, (2) $C_{1-6}$alkyl or $C_{1-6}$alkoxy, both of which may be optionally substituted with 1-3 substituents selected from halogen, hydroxy and cyano, or (3) 5- to 6-membered monocyclic heteroaryl or 5- to 6-membered monocyclic heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nOC(O)R^9$, and —$(CH_2)_nN(R^{8a})C(O)R^9$;

$R^{8a}$ and $R^{8b}$ are each independently hydrogen or $C_{1-6}$alkyl;

$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;

m is 0, 1 or 2; and n is 0-3.

(V) A pharmaceutical composition, containing the compound according to any of the above (I)-(IV), or a pharmaceutically acceptable salt, a stereoisomer or a solvate thereof and one or more pharmaceutically acceptable carriers, and optionally further containing one or more antitumor agents and immunosuppressants, wherein the antitumor agents and immunosuppressive agents are:

(1) anti-metabolites selected from capecitabine, gemcitabine and pemetrexed disodium;

(2) growth factor inhibitors selected from pazopanib, imatinib, erlotinib, lapatinib, gefitinib and vandetanib;

(3) antibodies selected from Herceptin and Avastin;

(4) mitotic inhibitors selected from paclitaxel, vinorelbine, docetaxel and doxorubicin;

(5) anti-tumor hormones selected from letrozole, tamoxifen, fulvestrant, flutamide and triptorelin;

(6) alkylating agents selected from cyclophosphamide, nitrogen mustard, melphalan, chlorambucil and carmustine;
(7) platinum metals selected from carboplatin, cisplatin and oxaliplatin;
(8) topoisomerase inhibitors selected from camptothecin, topotecan and irinotecan;
(9) immunosuppressants selected from everolimus, sirolimus and temsirolimus;
(10) purine analogues selected from 6-mercaptopurine, 6-thioguanine and azathioprine;
(11) antibiotics selected from streptozotocin D, daunorubicin, doxorubicin, mitoxantrone, bleomycin and plicamycin; or
(12) adrenal cortex inhibitor which is aminoglutethimide.

(VI) A use of the compound according to any of the above (I)-(IV), or a pharmaceutically acceptable salt, a stereoisomer or a solvate thereof in manufacture of a medicament for treating and/or preventing proliferative diseases including cancer and non-cancer diseases, wherein the cancer disease is selected from a brain tumor, lung cancer, non-small cell lung cancer, squamous cell carcinoma, bladder cancer, stomach cancer, ovarian cancer, peritoneal cancer, pancreatic cancer, breast cancer, head and neck cancer, cervical cancer, endometrial cancer, colorectal cancer, liver cancer, kidney cancer, esophageal adenocarcinoma, esophageal squamous cell carcinoma, solid tumors, non-Hodgkin's lymphoma, glioma, glioblastoma multiforme, gliosarcoma, prostate cancer, thyroid carcinoma, genital tract carcinoma, carcinoma in situ, lymphoma, histiocytic lymphoma, neurofibromatosis, bone cancer, skin cancer, brain cancer, colon cancer, testicular cancer, small cell lung cancer, gastrointestinal stromal tumor, prostate tumor, mast cell tumor, multiple myeloma, melanoma, glioma glioblastoma, astrocytoma, neuroblastoma, sarcomas; and the non-cancer disease is selected from a skin disease or benign prostate hyperplasia.

(VII) A method for treating and/or preventing proliferative diseases, which comprises administering to a patient a therapeutically effective amount of the compound according to any of the above (I)-(IV), or a pharmaceutically acceptable salt, a stereoisomer or a solvate thereof.

The following compound, or a pharmaceutically acceptable salt, a stereoisomer or a solvate thereof is preferable:

TABLE 1

The preferable compound of the present invention

| Nos. | Structure |
|---|---|
| 1 | 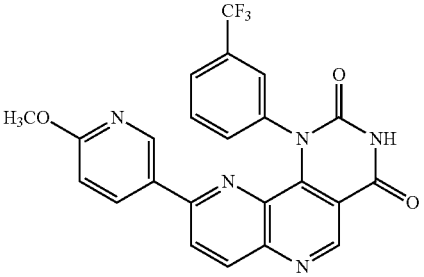 [SMILES: COc1ccc(-c2ccc3ncc4c(=O)[nH]c(=O)n(-c5cccc(C(F)(F)F)c5)c4c3n2)cn1] |
| 2 | 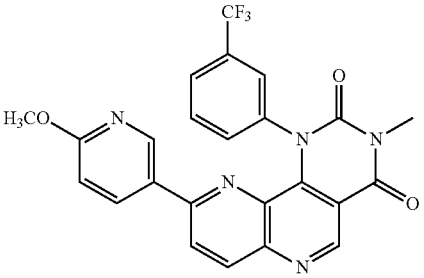 [SMILES: COc1ccc(-c2ccc3ncc4c(=O)n(C)c(=O)n(-c5cccc(C(F)(F)F)c5)c4c3n2)cn1] |
| 3 | 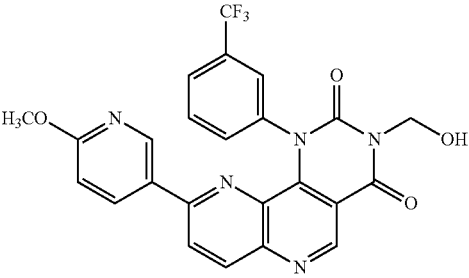 [SMILES: COc1ccc(-c2ccc3ncc4c(=O)n(CO)c(=O)n(-c5cccc(C(F)(F)F)c5)c4c3n2)cn1] |
| 4 | 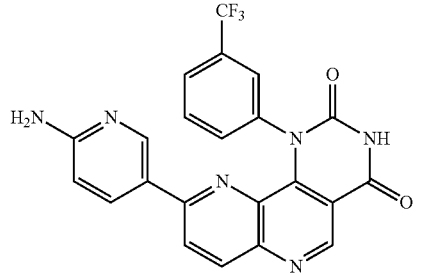 |
| 5 | 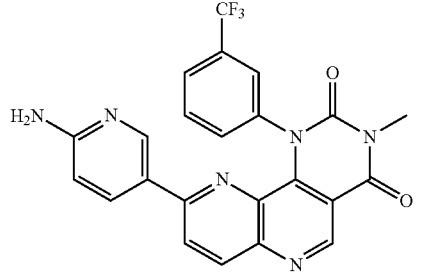 |
| 6 | 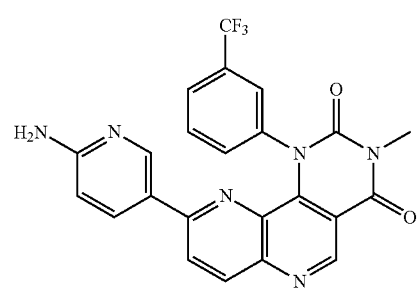 [SMILES: Cn1c(=O)c2cnc3ccc(-c4ccc(N)nc4)nc3c2n(-c2cccc(C(F)(F)F)c2)c1=O] |

TABLE 1-continued

The preferable compound of the present invention

| Nos. | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |

TABLE 1-continued

The preferable compound of the present invention

| Nos. | Structure |
|---|---|
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |

TABLE 1-continued

The preferable compound of the present invention

| Nos. | Structure |
|---|---|
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |

TABLE 1-continued

The preferable compound of the present invention

| Nos. | Structure |
|------|-----------|
| 37 | 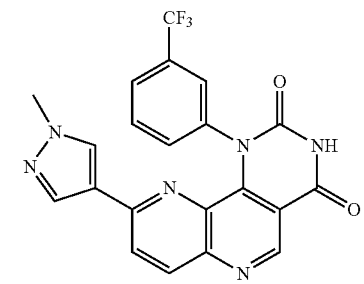 [SMILES: Cn1cc(-c2ccc3ncc4c(=O)[nH]c(=O)n(-c5cccc(C(F)(F)F)c5)c4c3n2)cn1] |
| 38 | 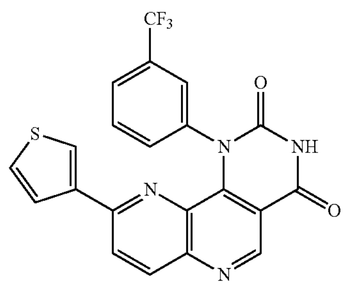 [SMILES: O=c1[nH]c(=O)n(-c2cccc(C(F)(F)F)c2)c2c1cnc1ccc(-c3ccsc3)nc12] |
| 39 | 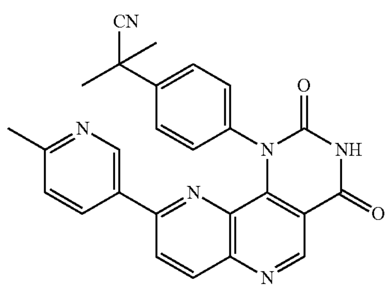 [SMILES: Cc1ccc(-c2ccc3ncc4c(=O)[nH]c(=O)n(-c5ccc(C(C)(C)C#N)cc5)c4c3n2)cn1] |
| 40 | 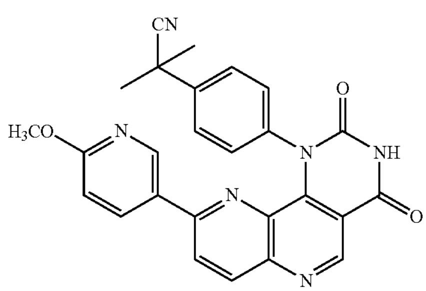 [SMILES: COc1ccc(-c2ccc3ncc4c(=O)[nH]c(=O)n(-c5ccc(C(C)(C)C#N)cc5)c4c3n2)cn1] |
| 41 | 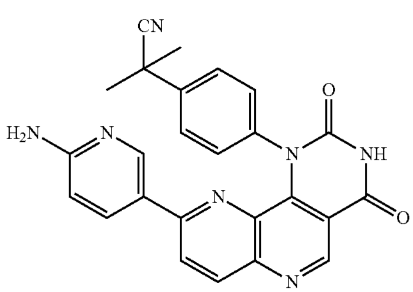 [SMILES: CC(C)(C#N)c1ccc(-n2c(=O)[nH]c(=O)c3cnc4ccc(-c5ccc(N)nc5)nc4c32)cc1] |
| 42 | |
| 43 | |
| 44 | |
| 45 | |
| 46 | |

TABLE 1-continued

The preferable compound of the present invention

| Nos. | Structure |
| --- | --- |
| 47 | *(structure)* |
| 48 | *(structure)* |
| 49 | *(structure)* |
| 50 | *(structure)* |
| 51 | *(structure)* |
| 52 | *(structure)* |
| 53 | *(structure)* |
| 54 | *(structure)* |
| 55 | *(structure)* |
| 56 | *(structure)* |

TABLE 1-continued

The preferable compound of the present invention

| Nos. | Structure |
|------|-----------|
| 57   | 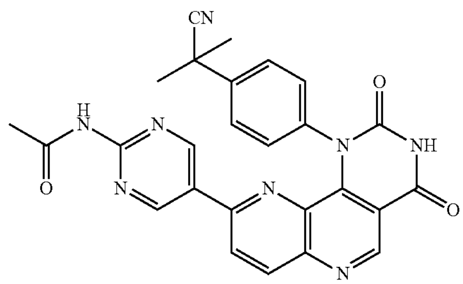 [SMILES: CC(=O)Nc1ccc(-c2ccc3ncc4c(=O)[nH]c(=O)n(-c5ccc(C(C)(C)C#N)cc5)c4c3n2)cn1]          |
| 58   | 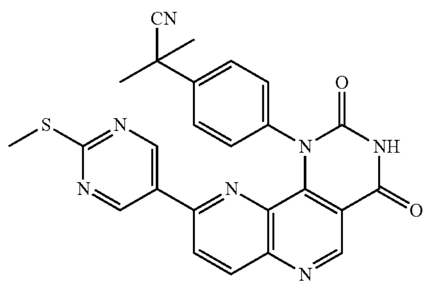 [SMILES: CSc1ncc(-c2ccc3ncc4c(=O)[nH]c(=O)n(-c5ccc(C(C)(C)C#N)cc5)c4c3n2)cn1]          |
| 59   | 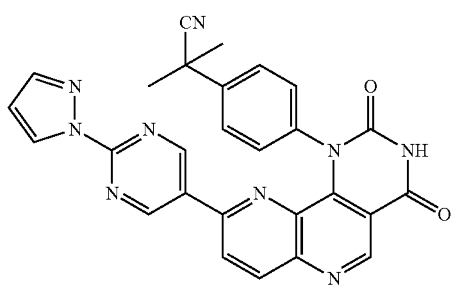 [SMILES: CC(C)(C#N)c1ccc(-n2c(=O)[nH]c(=O)c3cnc4ccc(-c5cnc(-n6cccn6)nc5)nc4c32)cc1]          |
| 60   | 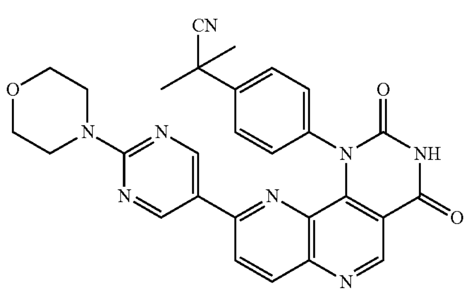 [SMILES: CC(C)(C#N)c1ccc(-n2c(=O)[nH]c(=O)c3cnc4ccc(-c5cnc(N6CCOCC6)nc5)nc4c32)cc1]          |
| 61   | 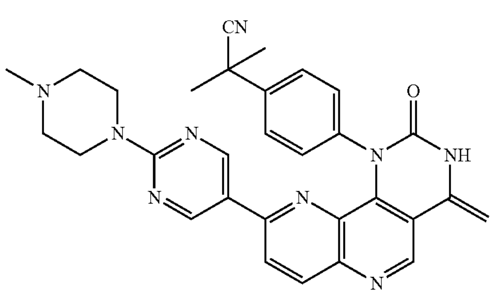          |
| 62   |           |
| 63   |           |
| 64   |           |
| 65   |           |
| 66   |           |

TABLE 1-continued

The preferable compound of the present invention

| Nos. | Structure |
|---|---|
| 67 | 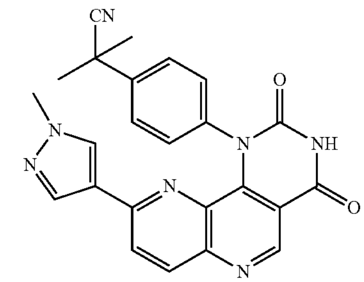 [SMILES: Cn1cc(-c2ccc3ncc4c(=O)[nH]c(=O)n(-c5ccc(C(C)(C)C#N)cc5)c4c3n2)cn1] |
| 68 | 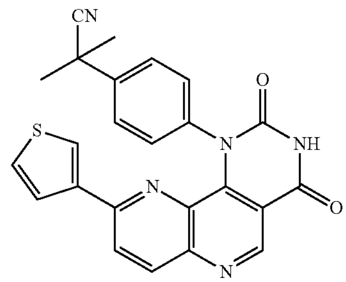 [SMILES: CC(C)(C#N)c1ccc(-n2c(=O)[nH]c(=O)c3cnc4ccc(-c5ccsc5)nc4c32)cc1] |
| 69 | 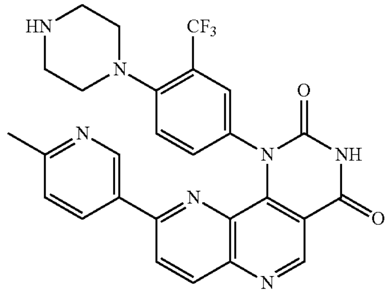 [SMILES: Cc1ccc(-c2ccc3ncc4c(=O)[nH]c(=O)n(-c5ccc(N6CCNCC6)c(C(F)(F)F)c5)c4c3n2)cn1] |
| 70 | 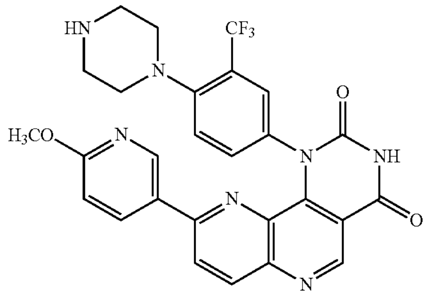 [SMILES: COc1ccc(-c2ccc3ncc4c(=O)[nH]c(=O)n(-c5ccc(N6CCNCC6)c(C(F)(F)F)c5)c4c3n2)cn1] |
| 71 | 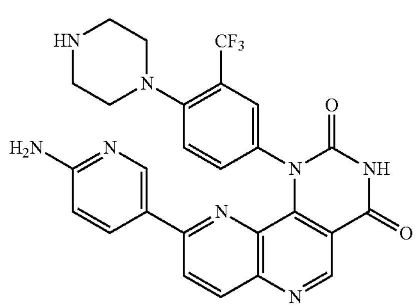 [SMILES: Nc1ccc(-c2ccc3ncc4c(=O)[nH]c(=O)n(-c5ccc(N6CCNCC6)c(C(F)(F)F)c5)c4c3n2)cn1] |
| 72 | |
| 73 | |
| 74 | |
| 75 | |
| 76 | |

TABLE 1-continued

The preferable compound of the present invention

| Nos. | Structure |
|---|---|
| 77 | 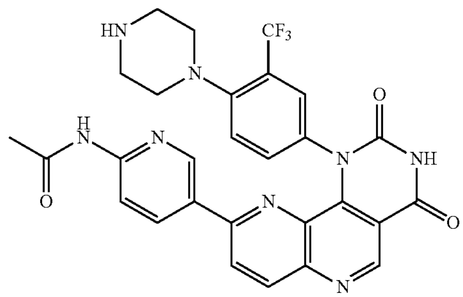 [SMILES: CC(=O)Nc1ccc(-c2ccc3ncc4c(=O)[nH]c(=O)n(-c5ccc(N6CCNCC6)c(C(F)(F)F)c5)c4c3n2)cn1] |
| 78 | 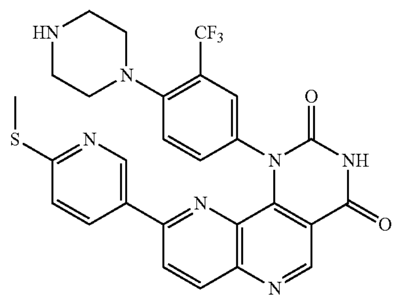 [SMILES: CSc1ccc(-c2ccc3ncc4c(=O)[nH]c(=O)n(-c5ccc(N6CCNCC6)c(C(F)(F)F)c5)c4c3n2)cn1] |
| 79 | 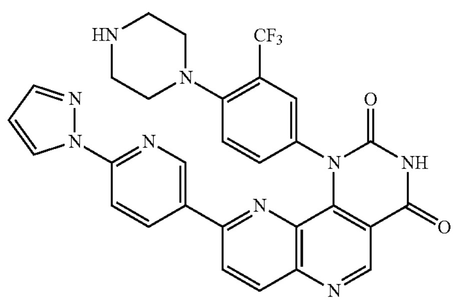 [SMILES: O=c1[nH]c(=O)n(-c2ccc(N3CCNCC3)c(C(F)(F)F)c2)c2c1cnc1ccc(-c3ccc(-n4cccn4)nc3)nc12] |
| 80 | 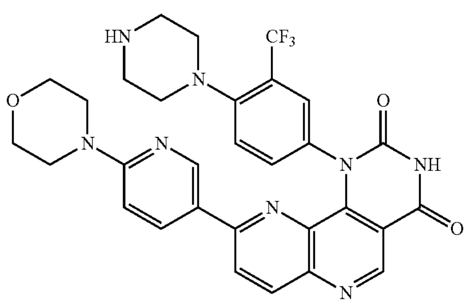 [SMILES: O=c1[nH]c(=O)n(-c2ccc(N3CCNCC3)c(C(F)(F)F)c2)c2c1cnc1ccc(-c3ccc(N4CCOCC4)nc3)nc12] |
| 81 | 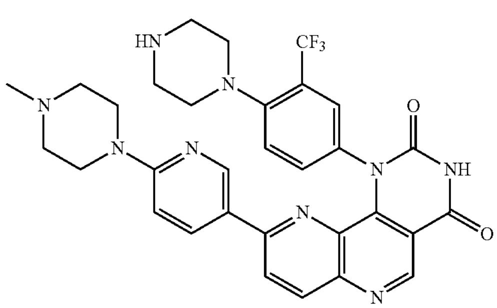 |
| 82 | |
| 83 | |
| 84 | |
| 85 | |
| 86 | |

TABLE 1-continued

The preferable compound of the present invention

| Nos. | Structure |
|---|---|
| 87 | 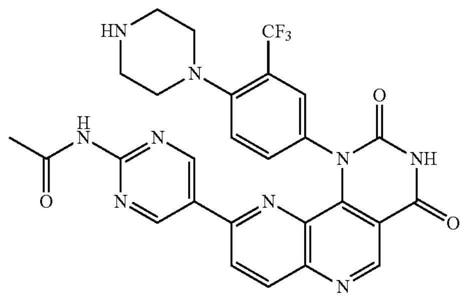 |
| 88 | 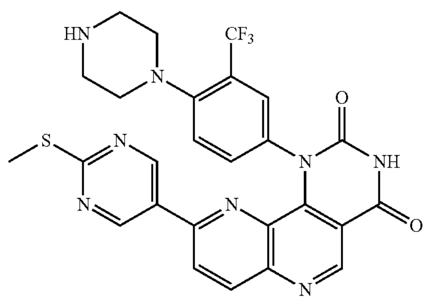 [SMILES: CSc1ncc(-c2ccc3ncc4c(=O)[nH]c(=O)n(-c5ccc(N6CCNCC6)c(C(F)(F)F)c5)c4c3n2)cn1] |
| 89 | 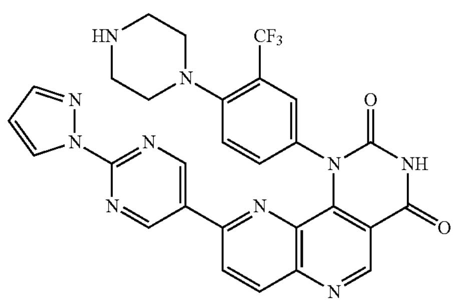 [SMILES: O=c1[nH]c(=O)n(-c2ccc(N3CCNCC3)c(C(F)(F)F)c2)c2c1cnc1ccc(-c3cnc(-n4cccn4)nc3)nc12] |
| 90 | 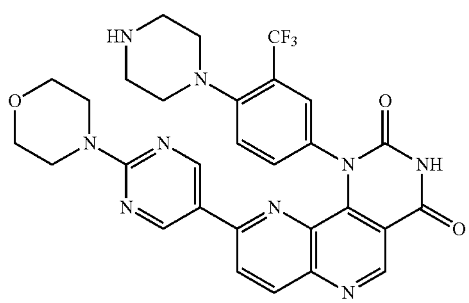 [SMILES: O=c1[nH]c(=O)n(-c2ccc(N3CCNCC3)c(C(F)(F)F)c2)c2c1cnc1ccc(-c3cnc(N4CCOCC4)nc3)nc12] |
| 91 | 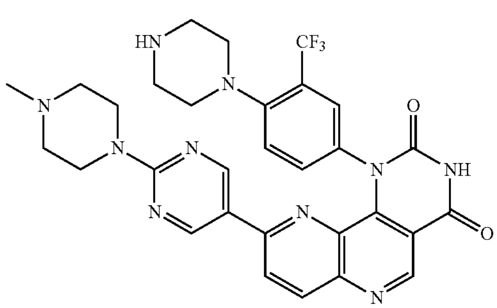 [SMILES: CN1CCN(c2ncc(-c3ccc4ncc5c(=O)[nH]c(=O)n(-c6ccc(N7CCNCC7)c(C(F)(F)F)c6)c5c4n3)cn2)CC1] |
| 92 | 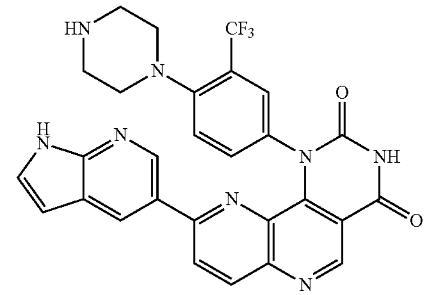 [SMILES: O=c1[nH]c(=O)n(-c2ccc(N3CCNCC3)c(C(F)(F)F)c2)c2c1cnc1ccc(-c3cnc4[nH]ccc4c3)nc12] |
| 93 | 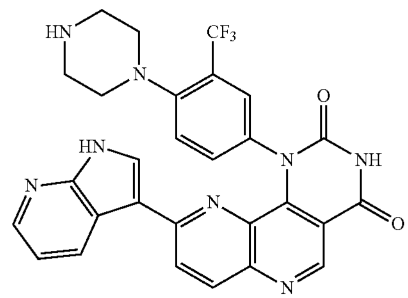 [SMILES: O=c1[nH]c(=O)n(-c2ccc(N3CCNCC3)c(C(F)(F)F)c2)c2c1cnc1ccc(-c3c[nH]c4ncccc34)nc12] |
| 94 | 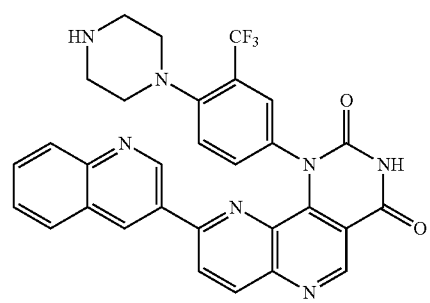 [SMILES: O=c1[nH]c(=O)n(-c2ccc(N3CCNCC3)c(C(F)(F)F)c2)c2c1cnc1ccc(-c3cnc4ccccc4c3)nc12] |
| 95 | 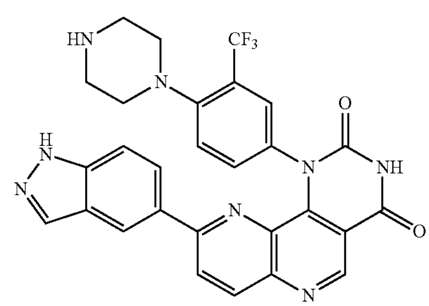 [SMILES: O=c1[nH]c(=O)n(-c2ccc(N3CCNCC3)c(C(F)(F)F)c2)c2c1cnc1ccc(-c3ccc4[nH]ncc4c3)nc12] |
| 96 | 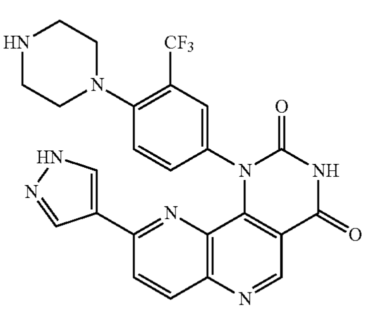 [SMILES: O=c1[nH]c(=O)n(-c2ccc(N3CCNCC3)c(C(F)(F)F)c2)c2c1cnc1ccc(-c3cn[nH]c3)nc12] |

TABLE 1-continued

The preferable compound of the present invention

| Nos. | Structure |
|---|---|
| 97 | 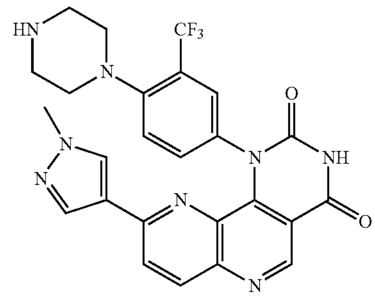 [SMILES: Cn1cc(-c2ccc3ncc4c(=O)[nH]c(=O)n(-c5ccc(N6CCNCC6)c(C(F)(F)F)c5)c4c3n2)cn1] |
| 98 | 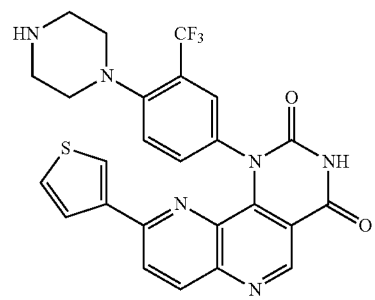 [SMILES: O=c1[nH]c(=O)n(-c2ccc(N3CCNCC3)c(C(F)(F)F)c2)c2c1cnc1ccc(-c3ccsc3)nc12] |

TABLE 2

The preferable compound of the present invention

| Nos. | Structure |
|---|---|
| 99 | |
| 100 | |
| 101 | 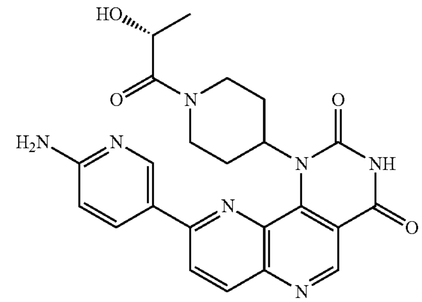 [SMILES: C[C@@H](O)C(=O)N1CCC(n2c(=O)[nH]c(=O)c3cnc4ccc(-c5ccc(N)nc5)nc4c32)CC1] |
| 102 | 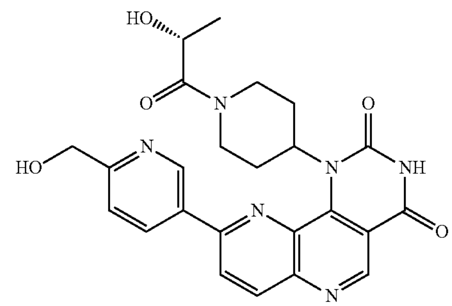 [SMILES: C[C@@H](O)C(=O)N1CCC(n2c(=O)[nH]c(=O)c3cnc4ccc(-c5ccc(CO)nc5)nc4c32)CC1] |
| 103 | 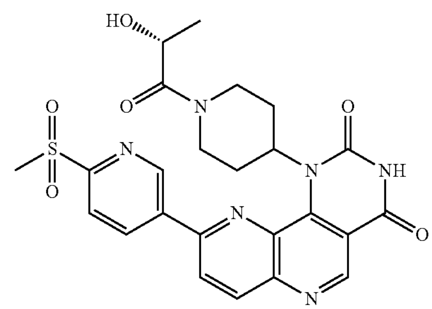 [SMILES: C[C@@H](O)C(=O)N1CCC(n2c(=O)[nH]c(=O)c3cnc4ccc(-c5ccc(S(C)(=O)=O)nc5)nc4c32)CC1] |
| 104 | 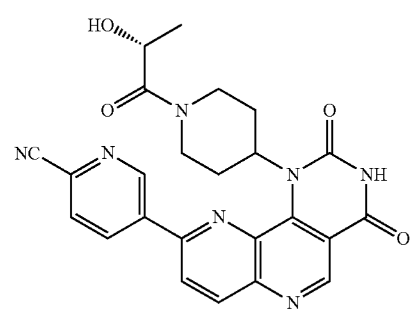 [SMILES: C[C@@H](O)C(=O)N1CCC(n2c(=O)[nH]c(=O)c3cnc4ccc(-c5ccc(C#N)nc5)nc4c32)CC1] |
| 105 | 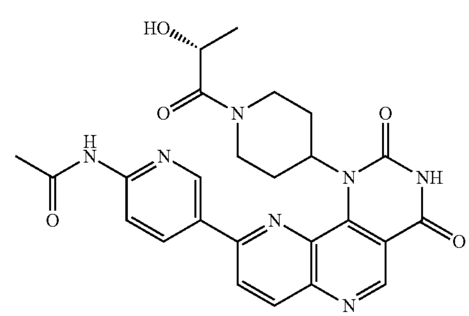 [SMILES: CC(=O)Nc1ncc(-c2ccc3ncc4c(=O)[nH]c(=O)n(C5CCN(C(=O)[C@@H](C)O)CC5)c4c3n2)cn1] |

TABLE 2-continued

The preferable compound of the present invention

| Nos. | Structure |
|------|-----------|
| 106 | (structure) |
| 107 | (structure) |
| 108 | (structure) |
| 109 | (structure) |
| 110 | (structure) |
| 111 | (structure) |
| 112 | (structure) |
| 113 | (structure) |
| 114 | (structure) |
| 115 | (structure) |

TABLE 2-continued

The preferable compound of the present invention

| Nos. | Structure |
|---|---|
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |
| 125 | (structure) |

TABLE 2-continued

The preferable compound of the present invention

| Nos. | Structure |
|---|---|
| 126 | 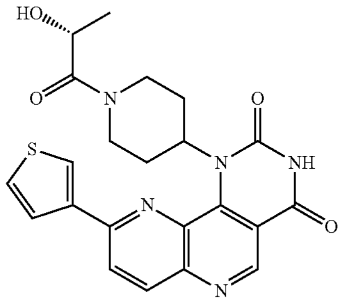 [SMILES: C[C@@H](O)C(=O)N1CCC(n2c(=O)[nH]c(=O)c3cnc4ccc(-c5ccsc5)nc4c32)CC1] |
| 127 | 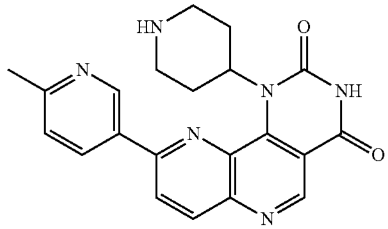 |
| 128 | 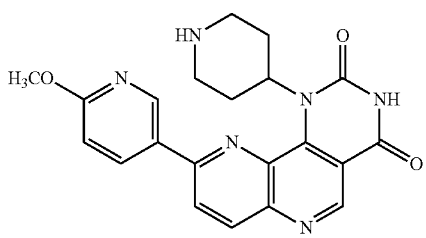 [SMILES: COc1ccc(-c2ccc3ncc4c(=O)[nH]c(=O)n(C5CCNCC5)c4c3n2)cn1] |
| 129 | 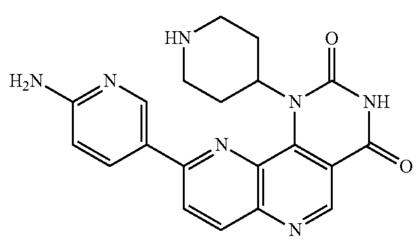 [SMILES: Nc1ccc(-c2ccc3ncc4c(=O)[nH]c(=O)n(C5CCNCC5)c4c3n2)cn1] |
| 130 | 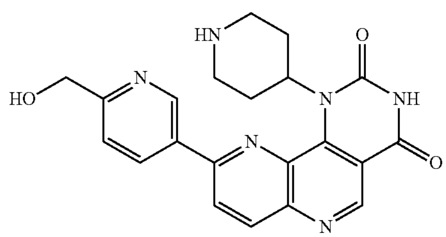 [SMILES: O=c1[nH]c(=O)n(C2CCNCC2)c2c1cnc1ccc(-c3ccc(CO)nc3)nc12] |
| 131 | 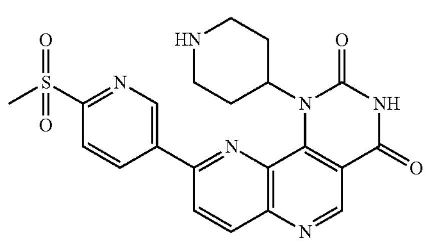 [SMILES: CS(=O)(=O)c1ccc(-c2ccc3ncc4c(=O)[nH]c(=O)n(C5CCNCC5)c4c3n2)cn1] |
| 132 | 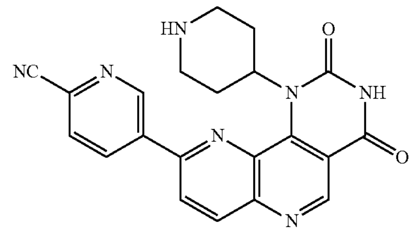 |
| 133 | 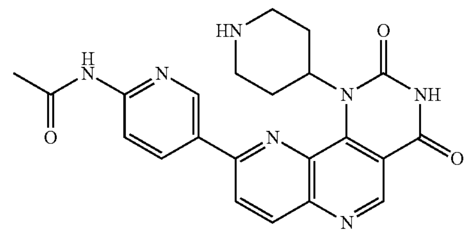 |
| 134 | 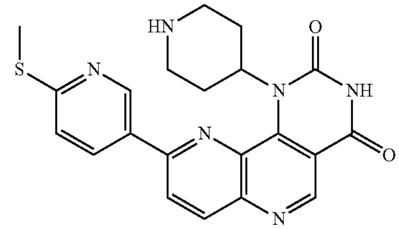 [SMILES: CSc1ccc(-c2ccc3ncc4c(=O)[nH]c(=O)n(C5CCNCC5)c4c3n2)cn1] |
| 135 | 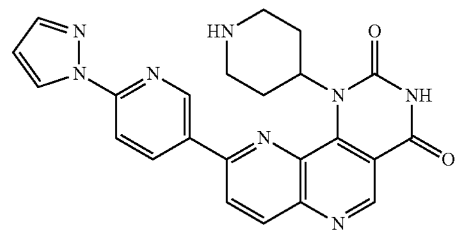 |
| 136 | 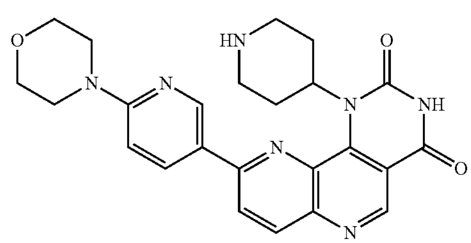 |
| 137 | 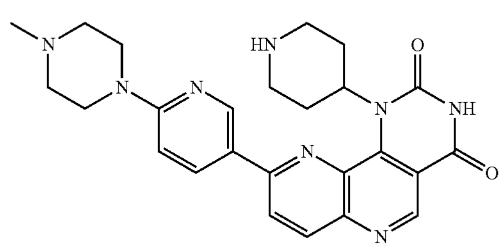 |

TABLE 2-continued

The preferable compound of the present invention

| Nos. | Structure |
|---|---|
| 138 | 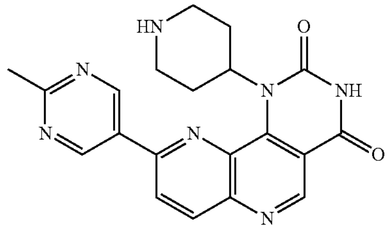 [SMILES: Cc1ncc(-c2ccc3ncc4c(=O)[nH]c(=O)n(C5CCNCC5)c4c3n2)cn1] |
| 139 | 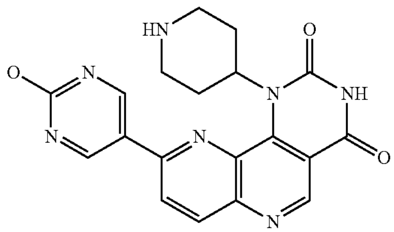 [SMILES: O=c1[nH]c(=O)n(C2CCNCC2)c2c1cnc1ccc(-c3cnc(O)nc3)nc12] |
| 140 | 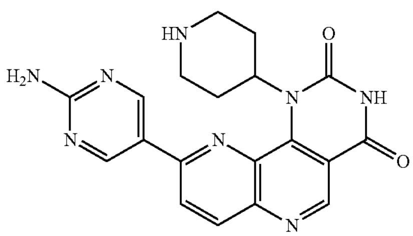 [SMILES: Nc1ncc(-c2ccc3ncc4c(=O)[nH]c(=O)n(C5CCNCC5)c4c3n2)cn1] |
| 141 | 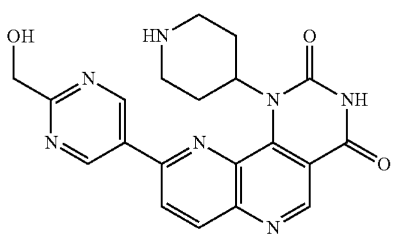 [SMILES: O=c1[nH]c(=O)n(C2CCNCC2)c2c1cnc1ccc(-c3cnc(CO)nc3)nc12] |
| 142 | 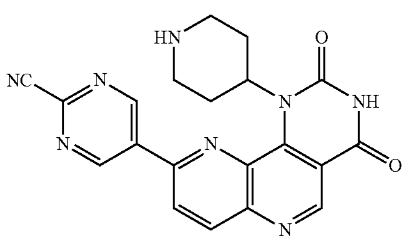 |
| 143 | 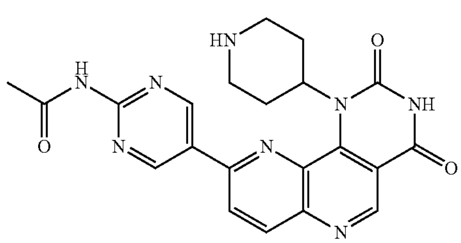 |
| 144 | |
| 145 | |
| 146 | |
| 147 | |
| 148 | |
| 149 | |

TABLE 2-continued

The preferable compound of the present invention

| Nos. | Structure |
|---|---|
| 150 | (structure) |
| 151 | (structure) |
| 152 | (structure) |
| 153 | (structure) |
| 154 | (structure) |
| 155 | (structure) |
| 156 | (structure) |
| 157 | (structure) |
| 158 | (structure) |
| 159 | (structure) |
| 160 | (structure) |

TABLE 2-continued

The preferable compound of the present invention

| Nos. | Structure |
|---|---|
| 161 | 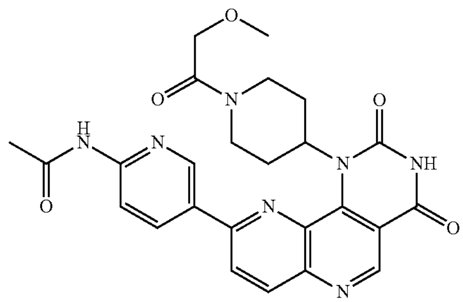 [SMILES: COCC(=O)N1CCC(n2c(=O)[nH]c(=O)c3cnc4ccc(-c5ccc(NC(C)=O)nc5)nc4c32)CC1] |
| 162 | 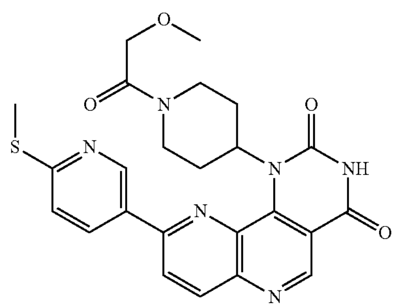 [SMILES: COCC(=O)N1CCC(n2c(=O)[nH]c(=O)c3cnc4ccc(-c5ccc(SC)nc5)nc4c32)CC1] |
| 163 | 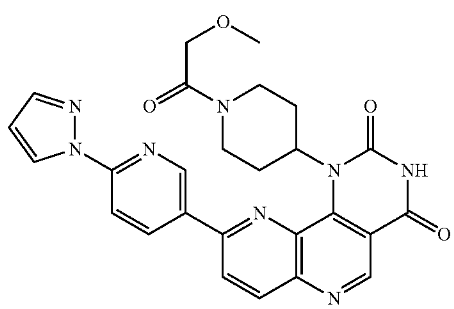 [SMILES: COCC(=O)N1CCC(n2c(=O)[nH]c(=O)c3cnc4ccc(-c5ccc(-n6cccn6)nc5)nc4c32)CC1] |
| 164 | 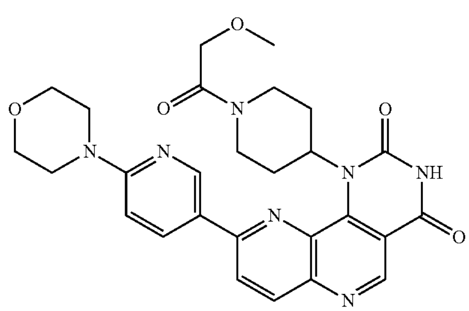 [SMILES: COCC(=O)N1CCC(n2c(=O)[nH]c(=O)c3cnc4ccc(-c5ccc(N6CCOCC6)nc5)nc4c32)CC1] |
| 165 | 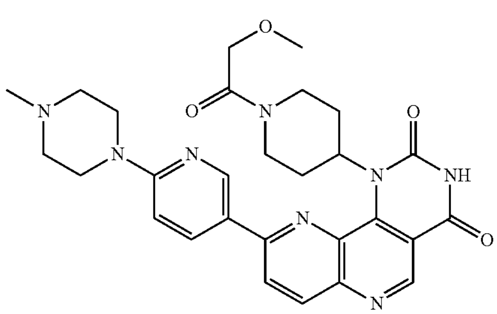 [SMILES: COCC(=O)N1CCC(n2c(=O)[nH]c(=O)c3cnc4ccc(-c5ccc(N6CCN(C)CC6)nc5)nc4c32)CC1] |
| 166 | |
| 167 | |
| 168 | |
| 169 | |
| 170 | |

TABLE 2-continued

The preferable compound of the present invention

| Nos. | Structure |
|------|-----------|
| 171 | 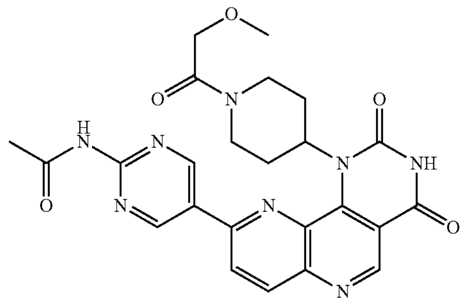 [SMILES: COCC(=O)N1CCC(n2c(=O)[nH]c(=O)c3cnc4ccc(-c5cnc(NC(C)=O)nc5)nc4c32)CC1] |
| 172 | 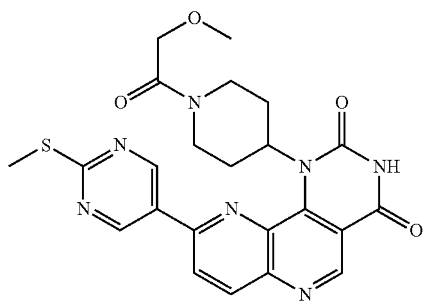 [SMILES: COCC(=O)N1CCC(n2c(=O)[nH]c(=O)c3cnc4ccc(-c5cnc(SC)nc5)nc4c32)CC1] |
| 173 | 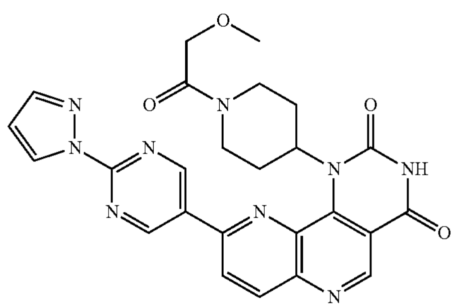 [SMILES: COCC(=O)N1CCC(n2c(=O)[nH]c(=O)c3cnc4ccc(-c5cnc(-n6cccn6)nc5)nc4c32)CC1] |
| 174 | 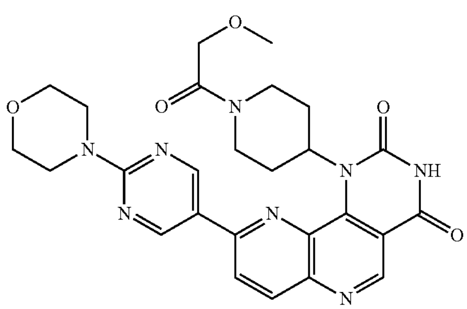 [SMILES: COCC(=O)N1CCC(n2c(=O)[nH]c(=O)c3cnc4ccc(-c5cnc(N6CCOCC6)nc5)nc4c32)CC1] |
| 175 | 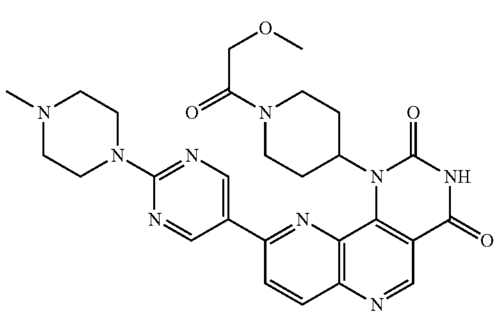 |
| 176 | 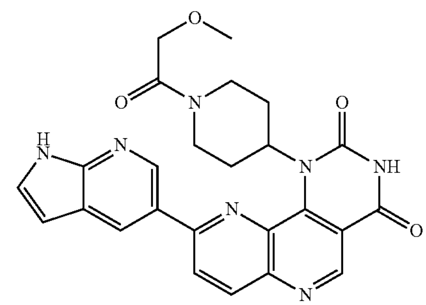 [SMILES: COCC(=O)N1CCC(n2c(=O)[nH]c(=O)c3cnc4ccc(-c5cnc6[nH]ccc6c5)nc4c32)CC1] |
| 177 | 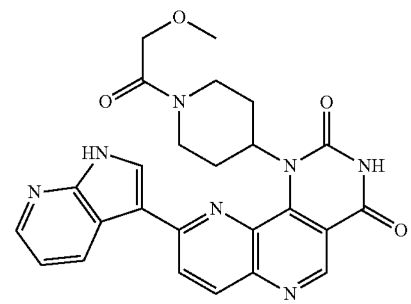 [SMILES: COCC(=O)N1CCC(n2c(=O)[nH]c(=O)c3cnc4ccc(-c5c[nH]c6ncccc56)nc4c32)CC1] |
| 178 | 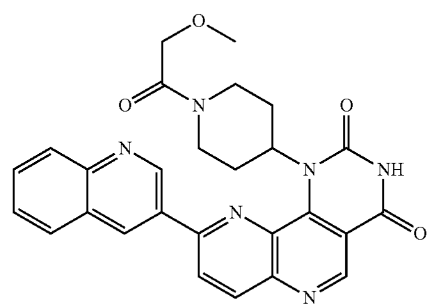 [SMILES: COCC(=O)N1CCC(n2c(=O)[nH]c(=O)c3cnc4ccc(-c5cnc6ccccc6c5)nc4c32)CC1] |
| 179 | 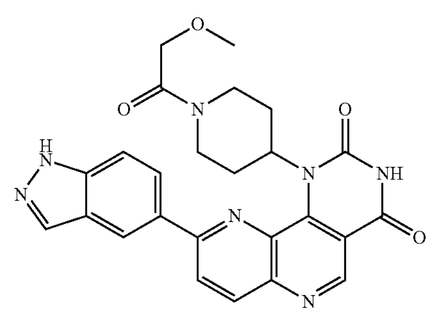 [SMILES: COCC(=O)N1CCC(n2c(=O)[nH]c(=O)c3cnc4ccc(-c5ccc6[nH]ncc6c5)nc4c32)CC1] |
| 180 | 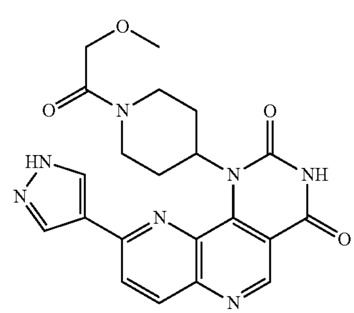 [SMILES: COCC(=O)N1CCC(n2c(=O)[nH]c(=O)c3cnc4ccc(-c5cn[nH]c5)nc4c32)CC1] |

TABLE 2-continued

The preferable compound of the present invention

| Nos. | Structure |
|---|---|
| 181 | 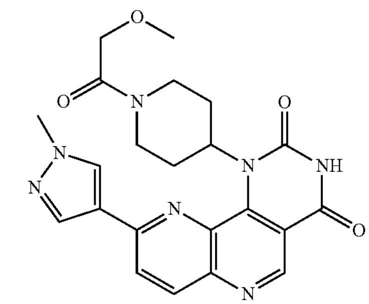 [SMILES: COCC(=O)N1CCC(n2c(=O)[nH]c(=O)c3cnc4ccc(-c5cnn(C)c5)nc4c32)CC1] |
| 182 | 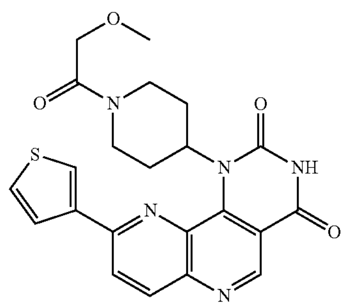 [SMILES: COCC(=O)N1CCC(n2c(=O)[nH]c(=O)c3cnc4ccc(-c5ccsc5)nc4c32)CC1] |
| 183 | 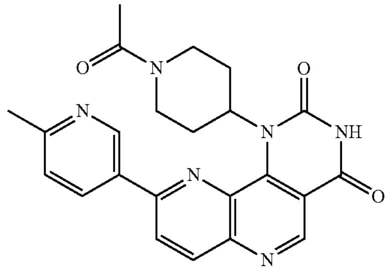 [SMILES: CC(=O)N1CCC(n2c(=O)[nH]c(=O)c3cnc4ccc(-c5ccc(C)nc5)nc4c32)CC1] |
| 184 | 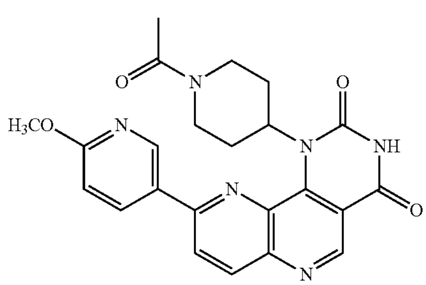 [SMILES: COc1ccc(-c2ccc3ncc4c(=O)[nH]c(=O)n(C5CCN(C(C)=O)CC5)c4c3n2)cn1] |
| 185 | 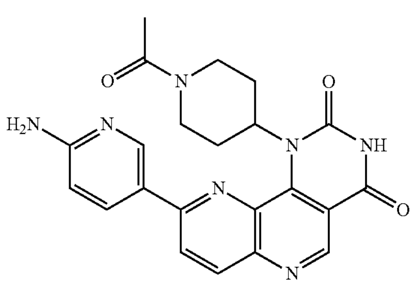 [SMILES: CC(=O)N1CCC(n2c(=O)[nH]c(=O)c3cnc4ccc(-c5ccc(N)nc5)nc4c32)CC1] |
| 186 | |
| 187 | |
| 188 | |
| 189 | |
| 190 | |

TABLE 2-continued
The preferable compound of the present invention
| Nos. | Structure |
|---|---|
| 191 | 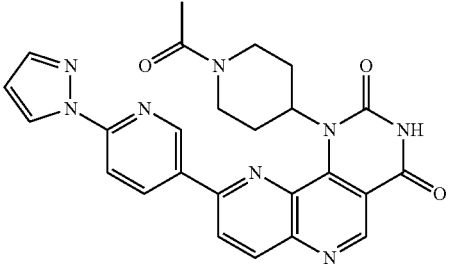 [SMILES: CC(=O)N1CCC(n2c(=O)[nH]c(=O)c3cnc4ccc(-c5ccc(-n6cccn6)nc5)nc4c32)CC1] |
| 192 | 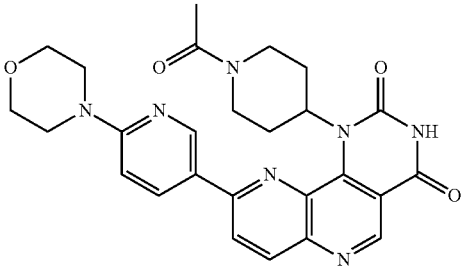 [SMILES: CC(=O)N1CCC(n2c(=O)[nH]c(=O)c3cnc4ccc(-c5ccc(N6CCOCC6)nc5)nc4c32)CC1] |
| 193 | 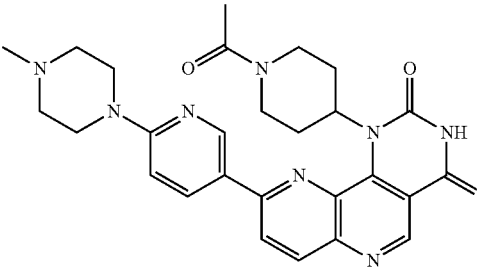 |
| 194 | 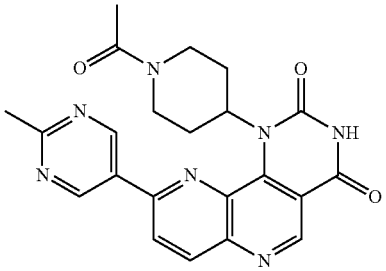 [SMILES: CC(=O)N1CCC(n2c(=O)[nH]c(=O)c3cnc4ccc(-c5cnc(C)nc5)nc4c32)CC1] |
| 195 | 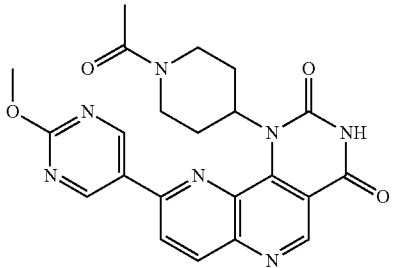 [SMILES: COc1ncc(-c2ccc3ncc4c(=O)[nH]c(=O)n(C5CCN(C(C)=O)CC5)c4c3n2)cn1] |
| 196 | 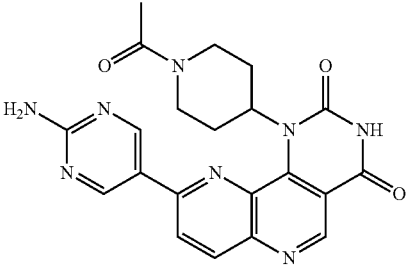 [SMILES: CC(=O)N1CCC(n2c(=O)[nH]c(=O)c3cnc4ccc(-c5cnc(N)nc5)nc4c32)CC1] |
| 197 | 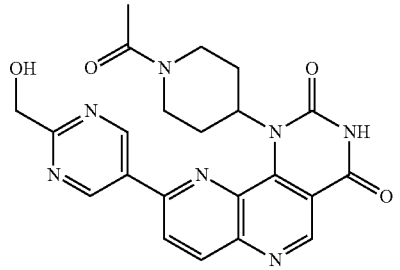 [SMILES: CC(=O)N1CCC(n2c(=O)[nH]c(=O)c3cnc4ccc(-c5cnc(CO)nc5)nc4c32)CC1] |
| 198 | 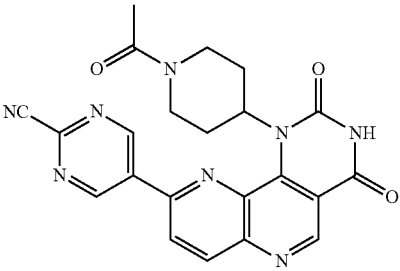 [SMILES: CC(=O)N1CCC(n2c(=O)[nH]c(=O)c3cnc4ccc(-c5cnc(C#N)nc5)nc4c32)CC1] |
| 199 | 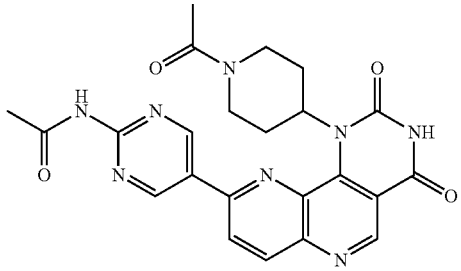 |
| 200 | 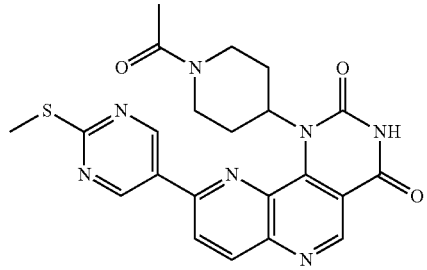 [SMILES: CSc1ncc(-c2ccc3ncc4c(=O)[nH]c(=O)n(C5CCN(C(C)=O)CC5)c4c3n2)cn1] |

TABLE 2-continued
The preferable compound of the present invention
| Nos. | Structure |
|------|-----------|
| 201 | 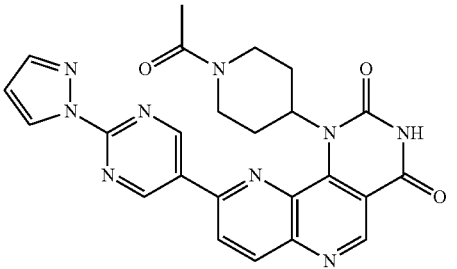 [SMILES: CC(=O)N1CCC(n2c(=O)[nH]c(=O)c3cnc4ccc(-c5cnc(-n6cccn6)nc5)nc4c32)CC1] |
| 202 | 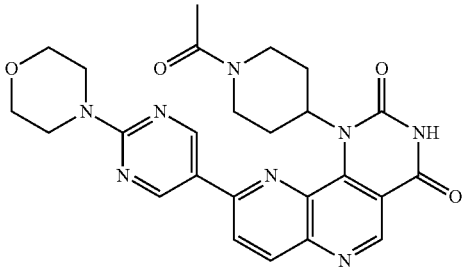 [SMILES: CC(=O)N1CCC(n2c(=O)[nH]c(=O)c3cnc4ccc(-c5cnc(N6CCOCC6)nc5)nc4c32)CC1] |
| 203 | 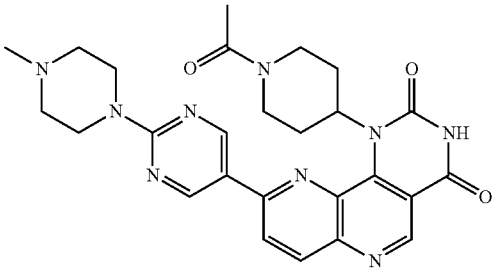 [SMILES: CC(=O)N1CCC(n2c(=O)[nH]c(=O)c3cnc4ccc(-c5cnc(N6CCN(C)CC6)nc5)nc4c32)CC1] |
| 204 | 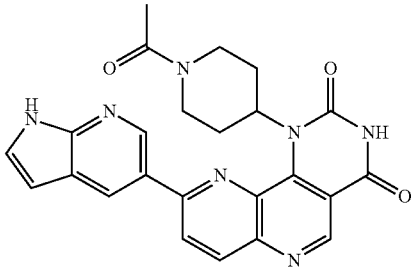 [SMILES: CC(=O)N1CCC(n2c(=O)[nH]c(=O)c3cnc4ccc(-c5cnc6[nH]ccc6c5)nc4c32)CC1] |
| 205 | 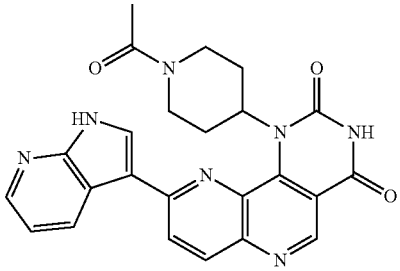 [SMILES: CC(=O)N1CCC(n2c(=O)[nH]c(=O)c3cnc4ccc(-c5c[nH]c6ncccc56)nc4c32)CC1] |
| 206 | 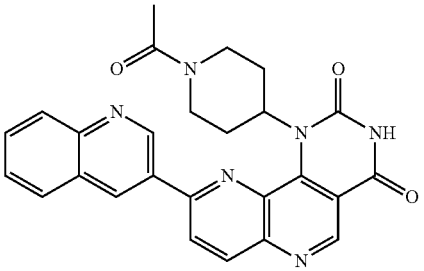 [SMILES: CC(=O)N1CCC(n2c(=O)[nH]c(=O)c3cnc4ccc(-c5cnc6ccccc6c5)nc4c32)CC1] |
| 207 | 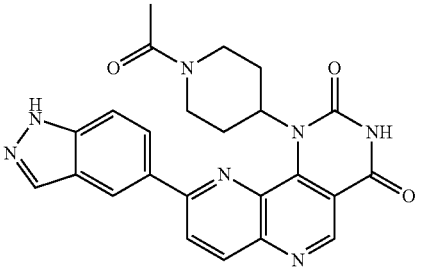 [SMILES: CC(=O)N1CCC(n2c(=O)[nH]c(=O)c3cnc4ccc(-c5ccc6[nH]ncc6c5)nc4c32)CC1] |
| 208 | 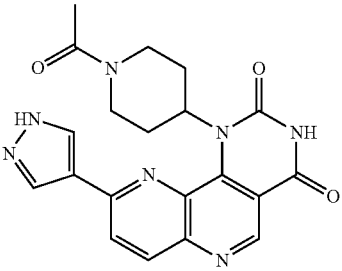 [SMILES: CC(=O)N1CCC(n2c(=O)[nH]c(=O)c3cnc4ccc(-c5cn[nH]c5)nc4c32)CC1] |
| 209 | 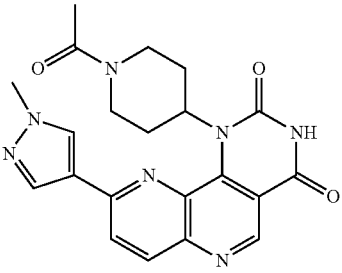 [SMILES: CC(=O)N1CCC(n2c(=O)[nH]c(=O)c3cnc4ccc(-c5cnn(C)c5)nc4c32)CC1] |
| 210 | 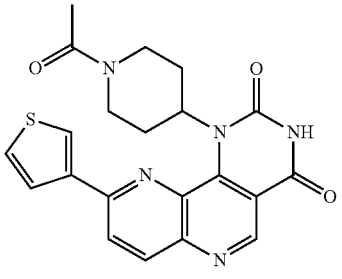 [SMILES: CC(=O)N1CCC(n2c(=O)[nH]c(=O)c3cnc4ccc(-c5ccsc5)nc4c32)CC1] |

TABLE 2-continued

The preferable compound of the present invention

| Nos. | Structure |
|---|---|
| 211 | (structure) |
| 212 | (structure) |
| 213 | (structure) |
| 214 | (structure) |
| 215 | (structure) |
| 216 | (structure) |
| 217 | (structure) |
| 218 | (structure) |
| 219 | (structure) |
| 220 | (structure) |

TABLE 2-continued

The preferable compound of the present invention

| Nos. | Structure |
|---|---|
| 221 | 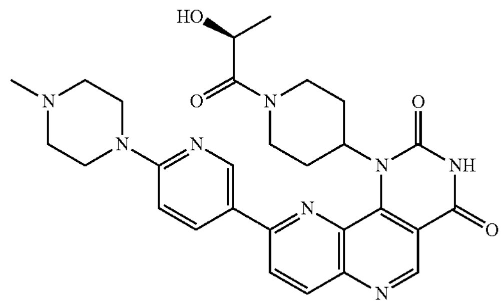 [SMILES: C[C@H](O)C(=O)N1CCC(n2c(=O)[nH]c(=O)c3cnc4ccc(-c5ccc(N6CCN(C)CC6)nc5)nc4c32)CC1] |
| 222 | 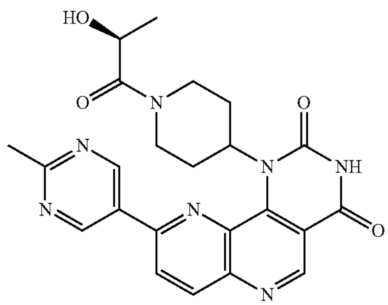 [SMILES: Cc1ncc(-c2ccc3ncc4c(=O)[nH]c(=O)n(C5CCN(C(=O)[C@H](C)O)CC5)c4c3n2)cn1] |
| 223 | 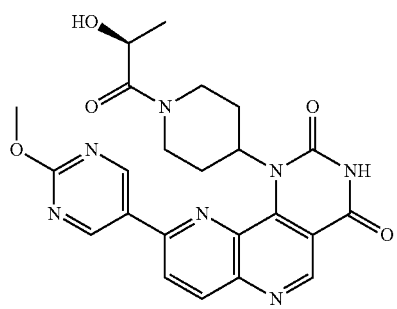 [SMILES: COc1ncc(-c2ccc3ncc4c(=O)[nH]c(=O)n(C5CCN(C(=O)[C@H](C)O)CC5)c4c3n2)cn1] |
| 224 | 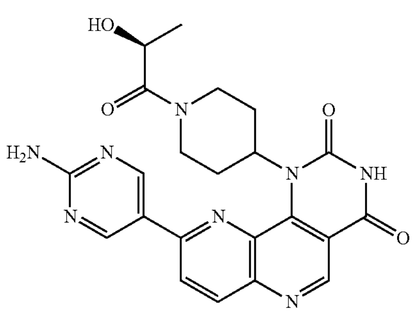 [SMILES: C[C@H](O)C(=O)N1CCC(n2c(=O)[nH]c(=O)c3cnc4ccc(-c5cnc(N)nc5)nc4c32)CC1] |
| 225 | 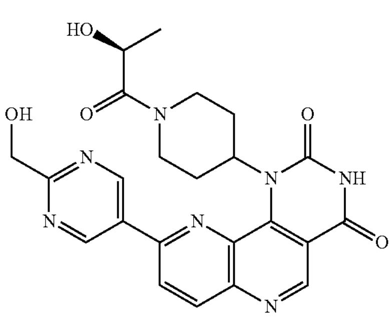 [SMILES: C[C@H](O)C(=O)N1CCC(n2c(=O)[nH]c(=O)c3cnc4ccc(-c5cnc(CO)nc5)nc4c32)CC1] |
| 226 | 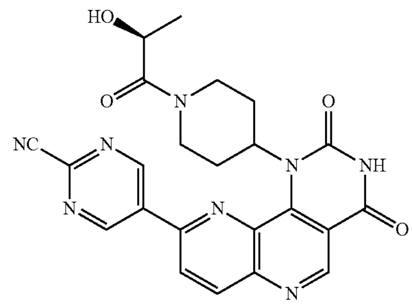 [SMILES: C[C@H](O)C(=O)N1CCC(n2c(=O)[nH]c(=O)c3cnc4ccc(-c5cnc(C#N)nc5)nc4c32)CC1] |
| 227 | 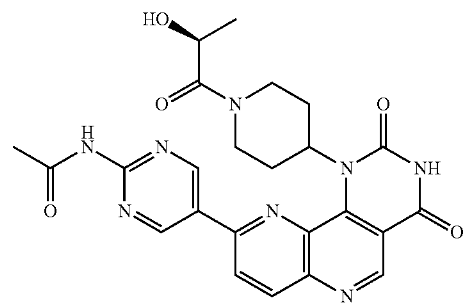 [SMILES: CC(=O)Nc1ncc(-c2ccc3ncc4c(=O)[nH]c(=O)n(C5CCN(C(=O)[C@H](C)O)CC5)c4c3n2)cn1] |
| 228 | 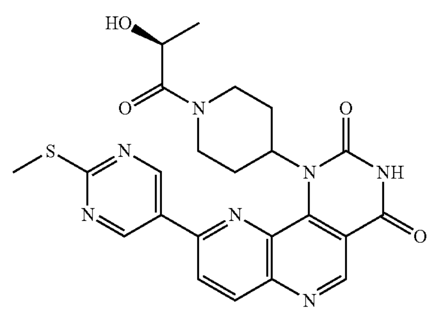 [SMILES: CSc1ncc(-c2ccc3ncc4c(=O)[nH]c(=O)n(C5CCN(C(=O)[C@H](C)O)CC5)c4c3n2)cn1] |
| 229 | 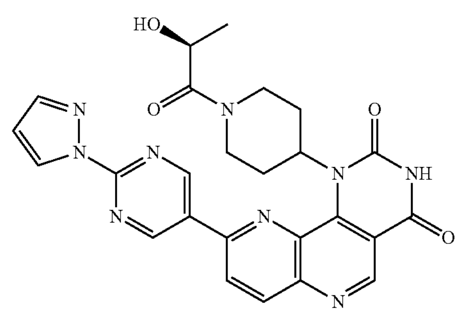 [SMILES: C[C@H](O)C(=O)N1CCC(n2c(=O)[nH]c(=O)c3cnc4ccc(-c5cnc(-n6cccn6)nc5)nc4c32)CC1] |
| 230 | 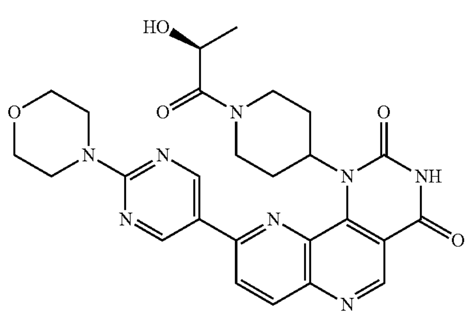 [SMILES: C[C@H](O)C(=O)N1CCC(n2c(=O)[nH]c(=O)c3cnc4ccc(-c5cnc(N6CCOCC6)nc5)nc4c32)CC1] |

TABLE 2-continued

The preferable compound of the present invention

| Nos. | Structure |
|---|---|
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |

TABLE 2-continued

The preferable compound of the present invention

| Nos. | Structure |
|---|---|
| 241 | (structure) |
| 242 | (structure) |
| 243 | (structure) |
| 244 | (structure) |
| 245 | (structure) |
| 246 | (structure) |
| 247 | (structure) |
| 248 | (structure) |
| 249 | (structure) |
| 250 | (structure) |

TABLE 2-continued

The preferable compound of the present invention

| Nos. | Structure |
|---|---|
| 251 | (structure) |
| 252 | (structure) |
| 253 | (structure) |
| 254 | (structure) |
| 255 | (structure) |
| 256 | (structure) |
| 257 | (structure) |
| 258 | (structure) |
| 259 | (structure) |
| 260 | (structure) |

TABLE 2-continued

The preferable compound of the present invention

| Nos. | Structure |
|---|---|
| 261 | 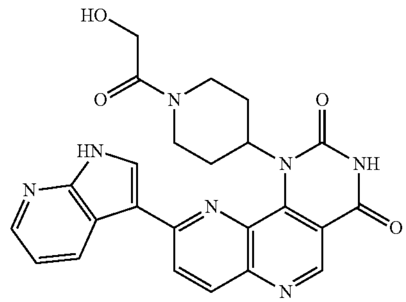 |
| 262 | 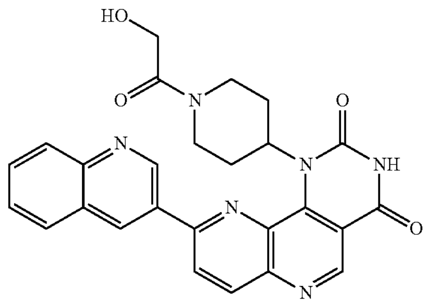 |
| 263 | 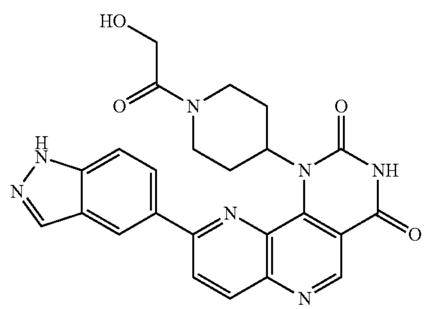 |
| 264 | 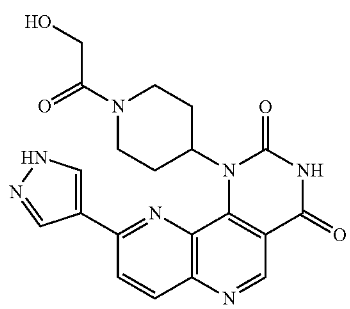 |
| 265 | 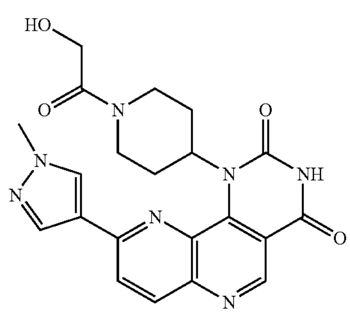 |
| 266 | |
| 267 | |
| 268 | |
| 269 | |
| 270 | |

TABLE 2-continued

The preferable compound of the present invention

| Nos. | Structure |
|---|---|
| 271 | 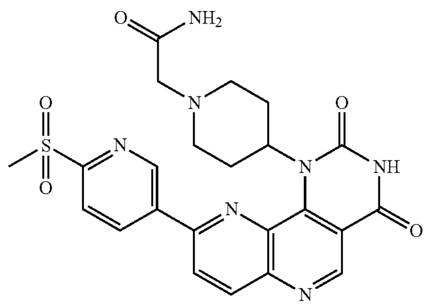 |
| 272 | 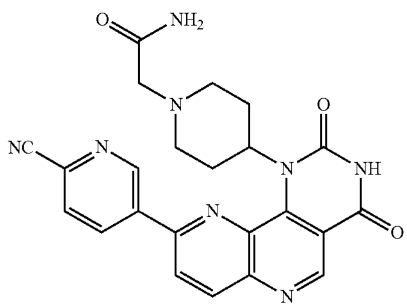 |
| 273 | 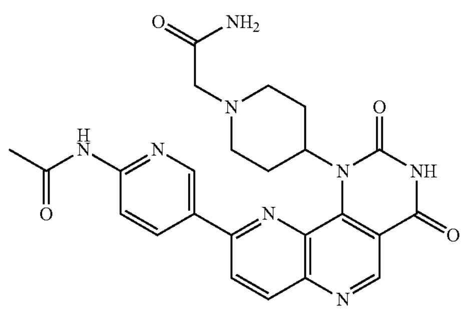 |
| 274 | 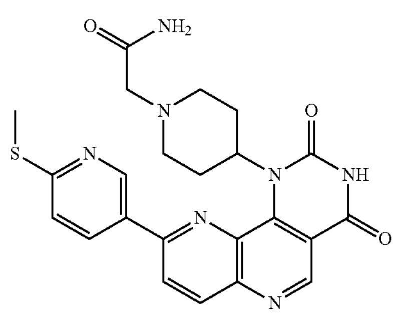 |
| 275 | 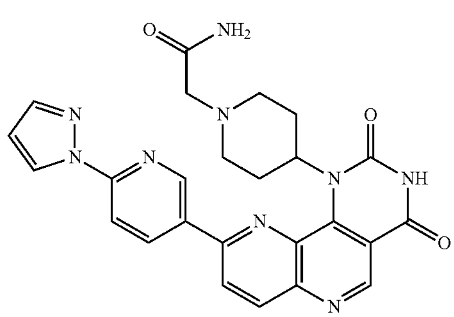 |
| 276 | |
| 277 | |
| 278 | |
| 279 | |
| 280 | |

TABLE 2-continued

The preferable compound of the present invention

| Nos. | Structure |
|---|---|
| 281 | (structure) |
| 282 | (structure) |
| 283 | (structure) |
| 284 | (structure) |
| 285 | (structure) |
| 286 | (structure) |
| 287 | (structure) |
| 288 | (structure) |
| 289 | (structure) |
| 290 | (structure) |

TABLE 2-continued

The preferable compound of the present invention

| Nos. | Structure |
|---|---|
| 291 | (structure) |
| 292 | (structure) |
| 293 | (structure) |
| 294 | (structure) |
| 295 | (structure) |
| 296 | (structure) |
| 297 | (structure) |
| 298 | (structure) |
| 299 | (structure) |

TABLE 2-continued

The preferable compound of the present invention

| Nos. | Structure |
|---|---|
| 300 | (structure) |
| 301 | (structure) |
| 302 | (structure) |
| 303 | (structure) |
| 304 | (structure) |
| 305 | (structure) |
| 306 | (structure) |
| 307 | (structure) |

TABLE 2-continued
The preferable compound of the present invention
| Nos. | Structure |
|---|---|
| 308 | 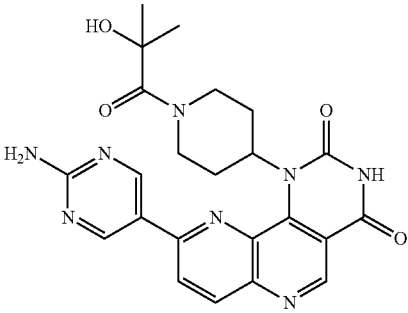 |
| 309 | 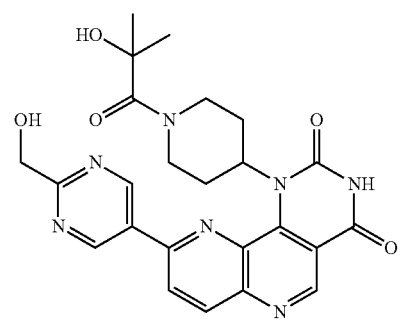 |
| 310 | 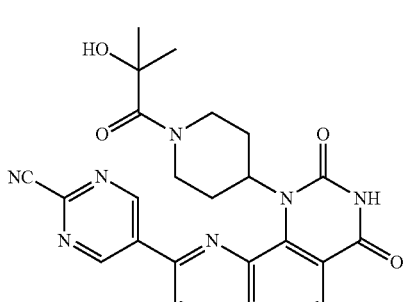 |
| 311 | 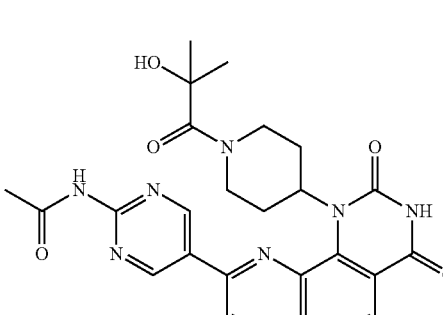 |
| 312 | 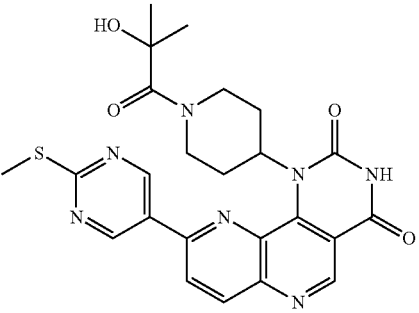 |
| 313 | 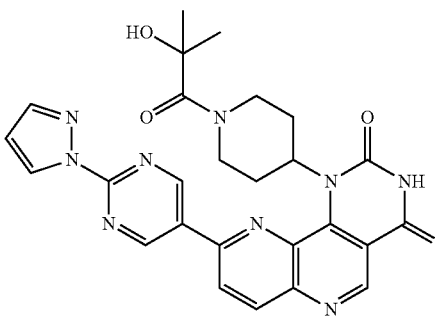 |
| 314 | 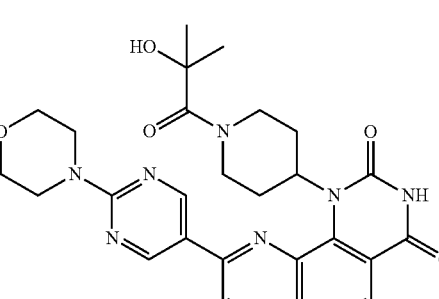 |
| 315 | 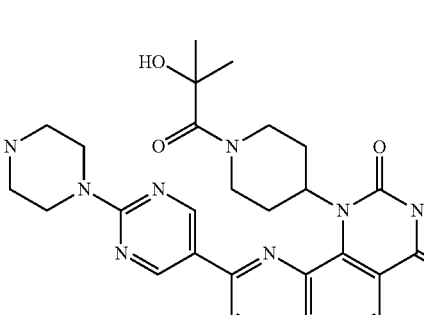 |

TABLE 2-continued

The preferable compound of the present invention

| Nos. | Structure |
|---|---|
| 316 | (structure) |
| 317 | (structure) |
| 318 | (structure) |
| 319 | (structure) |
| 320 | (structure) |
| 321 | (structure) |
| 322 | (structure) |

The term "halogen" as used herein comprises fluorine, chlorine, bromine and iodine.

The term "$C_{1-6}$alkyl" may be linear or branched, and for example comprises "$C_{1-4}$alkyl", "$C_{1-3}$alkyl", and "$C_{1-2}$alkyl". The specific example comprises but is not limited to methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "$C_{3-8}$cycloalkyl" as used herein includes for example "$C_{3-7}$cycloalkyl", "$C_{3-6}$cycloalkyl", "$C_{4-6}$cycloalkyl" and "$C_{5-6}$cycloalkyl". The specific example comprises but is not limited to cyclopropyl, cyclobutyl, cyclopentyl, cyclohexyl, cycloheptyl, cyclooctyl and the like.

The term "$C_{2-8}$alkenyl" as used herein may be linear or branched or cyclic, and for example comprises "$C_{2-5}$alkenyl", "$C_{2-4}$alkenyl", "$C_{2-3}$alkenyl" and "$C_{3-6}$cycloalkenyl". The specific example comprises but is not limited to ethenyl, 1-propenyl, 2-propenyl, 2-butenyl, 3-butenyl, 2-methyl-1-propenyl, 1-methyl-2-propenyl, 1-pentenyl, 2-pentenyl, 3-pentenyl, 2-methyl-1-butenyl, 3-methyl-1-butenyl, 2-methyl-3-butenyl, 1,1-dimethyl-2-propenyl, 1-ethyl-2-propenyl, 2-hexenyl, 3-hexenyl, 2-methyl-1-pentenyl, 3-methyl-1-pentenyl, 1-methyl-2-pentenyl, 3-methyl-2-pentenyl, 2-methyl-3-pentenyl, 1-methyl-4-pentenyl, 3-methyl-4-pentenyl, 1,1-dimethyl-3-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 2-ethyl-1-butenyl, 2-ethyl-3-butenyl, 2-heptenyl, 3-heptenyl, 4-heptenyl, 1-octenyl, 3-octenyl, 4-octenyl, 1,3-butadienyl, 2,4-pentadienyl, 1,4-hexadienyl, 2,4-hexadienyl, 1,5-heptadienyl, 2,5-heptadienyl, 2,6-octadienyl, cyclopentenyl, 1,3-cyclopentadienyl, cyclohexenyl, 1,4-cyclohexadienyl, cycloheptenyl, 1,4-cycloheptadienyl, cyclooctenyl, and the like.

The term "$C_{2-8}$alkynyl" as used herein may be linear or branched, and for example comprises "$C_{2-5}$alkynyl", "$C_{2-4}$alkynyl" and "$C_{2-3}$alkynyl". The specific example comprises but is not limited to ethynyl, 1-propynyl, 2-butynyl, 1-methyl-2-propynyl, 2-pentynyl, 3-pentynyl, 1-methyl-2-butynyl, 2-methyl-3-butynyl, 1,1-dimethyl-2-propynyl, 1-ethyl-2-propynyl, 2-hexynyl, 3-hexynyl, 1-methyl-2-pentynyl, 1-methyl-3-pentynyl, 2-methyl-3-pentynyl, 1,1-dimethyl-3-butynyl, 2-ethyl-3-butynyl, 2-heptynyl, 3-heptynyl, 4-methyl-2-hexynyl, 5-methyl-2-hexynyl, 2-methyl-3-hexynyl, 5-methyl-3-hexynyl, 2-methyl-4-hexynyl, 4-methyl-5-hexynyl, 2-octynyl, 3-octynyl, 4-octynyl, 4-methyl-2-heptynyl, 5-methyl-3-heptynyl, 6-methyl-3-heptynyl, 2-methyl-4-heptynyl, 2-methyl-5-heptynyl, 3-methyl-6-heptynyl, and the like.

The term "$C_{1-6}$alkoxy" as used herein refers to "$C_{1-6}$alkyl-O—", wherein "$C_{1-6}$alkyl" is defined as above.

The term "$C_{1-6}$alkylcarbonyl" as used herein refers to "$C_{1-6}$alkyl-C(O)—", wherein "$C_{1-6}$alkyl" is defined as above.

The term "6- to 14-membered aryl" as used herein includes 6- to 8-membered monocyclic aryl and 8- to 14-membered fused aryl. 6- to 8-membered monocyclic aryl includes for example phenyl cyclooctatetraenyl and the like. 8- to 14-membered fused aryl includes for example naphthyl, phenanthryl, 2,3-dihydro-1H-indenyl, 1H-indenyl, 1,2,3,4-tetrahydronaphthyl, 1,4-dihydronaphthyl and the like.

The term "5- to 14-membered heteroaryl" as used herein includes 5- to 8-membered monocyclic heteroaryl and 6- to 14-membered fused heteroaryl, wherein heteroatoms are nitrogen, oxygen, sulfur and the like. It includes the case that a carbon atom, a nitrogen atom or a sulfur atom is substituted by oxo.

Examples of 5- to 8-membered monocyclic heteroaryl include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azepinyl, 1,3-diazepinyl, azacyclooctatetraenyl and the like. It is preferably 5- to 6-membered monocyclic heteroaryl.

Examples of 6- to 14-membered fused heteroaryl include, but are not limited to, benzofuryl, isobenzofuryl, benzothienyl, indolyl, isoindolyl, benzoxazolyl, benzimidazolyl, indazolyl, benzotriazolyl, quinolyl, 2-quinolinone, 4-quinolinone, 1-isoquinolinone, isoquinolyl, acridinyl, phenanthridinyl, benzopyridazinyl, phthalazinyl, quinazolinyl, quinoxalinyl, phenazinyl, pteridinyl, purinyl, naphthyridinyl, phenazinyl, phenothiazinyl and the like. It is preferably 9- to 10-membered fused heteroaryl.

The term "3- to 14-membered heterocyclic group" as used herein includes 3- to 8-membered monocyclic heterocyclic group and 6- to 14-membered fused heterocyclic group, wherein heteroatoms are nitrogen, oxygen, sulfur and the like. It includes the case that a carbon atom, a nitrogen atom or a sulfur atom is substituted by oxo.

Examples of 3- to 8-membered monocyclic heterocyclic group include, but are not limited to, aziridinyl, 2H-aziridinyl, diaziridinyl, 3H-diazirinyl, azetidinyl, 1,4-dioxanyl, 1,3-dioxanyl, 1,3-dioxolanyl, 1,4-dioxinyl, tetrahydrofuryl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, piperidinyl, piperazinyl, morpholinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-keto, 3,4-dihydro-2H-pyranyl and the like. It is preferably 5- to 6-membered monocyclic heterocyclic group.

Examples of 6- to 14-membered fused heterocyclic group include, but are not limited to, tetrahydroimidazo[4,5-c]pyridyl, 3,4-dihydroquinazolinyl, 1,2-dihydroquinoxalinyl, benzo[d][1,3]dioxolyl, 1,3-dihydroisobenzofuryl, 2H-chromenyl, 2H-chromene-2-keto, 4H-chromenyl, 4H-chromene-4-keto, chromanyl, 4H-1,3-benzoxazinyl, 4,6-dihydro-1H-furo[3,4-d]imidazolyl, 3a,4,6,6a-tetrahydro-H-furo[3,4-d]imidazolyl, 4,6-dihydro-1H-thieno[3,4-d]imidazolyl, 4,6-dihydro-1H-pyrrolo[3,4-d]imidazolyl, 4,5,6,7-tetrahydro-1H-benzo[d]imidazolyl and the like. It is preferably 9- to 10-membered fused heterocyclic group.

The term "7- to 12-membered bridge group" as used herein refers to 7- to 12-membered bridge group in which any two rings share two non-adjacent atoms and all ring atoms are carbon atoms, or 7- to 12-membered bridge heterocyclic group containing at least one hetero atoms such as nitrogen, oxygen and sulfur and the like. The 7- to 12-membered bridge group and 7- to 12-membered bridge heterocyclic group may be saturated or partially saturated.

Saturated bridge group refers to an bridge group in which all rings are saturated, and preferably 7- to 8-membered saturated bridge group. The specific example comprises but is not limited to

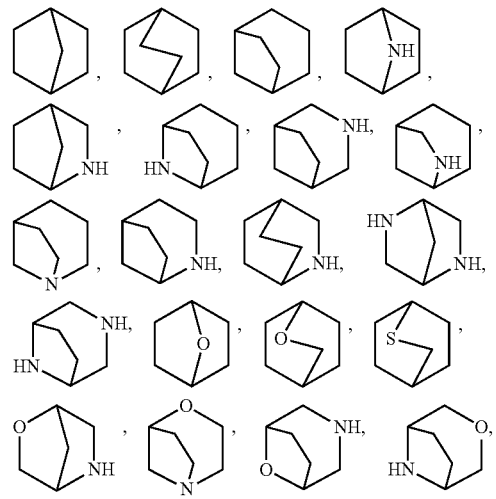

-continued

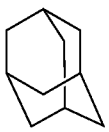

and the like.

Partially saturated bridge group means that at least one ring in the bridge group is an unsaturated cyclic group, preferably a 7- to 8-membered partially saturated bridge group. The specific example comprises but is not limited to

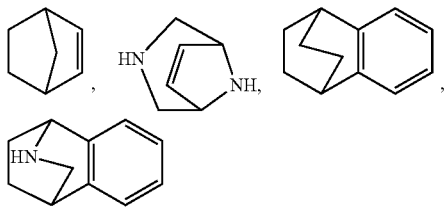

and the like.

The term "7- to 12-membered spirocyclic group" as used herein refers to 7- to 12-membered spirocyclic group wherein at least two rings share one atom and all ring atoms are carbon atoms, or 7- to 12-membered spiro-heterocyclic group containing at least one hetero atom such as nitrogen, oxygen and sulfur and the like. The 7- to 12-membered spirocyclic group and 7- to 12-membered spiro-heterocyclic group may be saturated or partially saturated.

Saturated spirocyclic group ring group means that all rings in the spirocyclic group are saturated cyclic groups. The specific example comprises but is not limited to

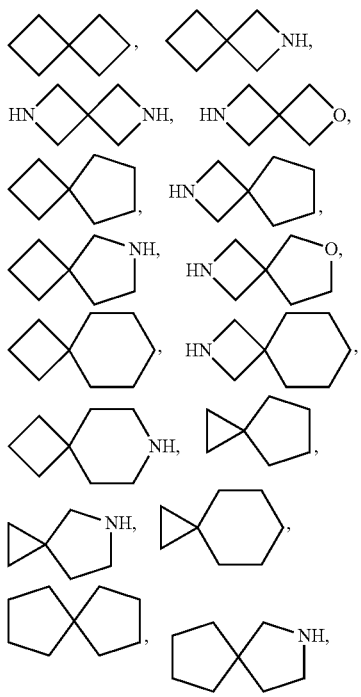

-continued

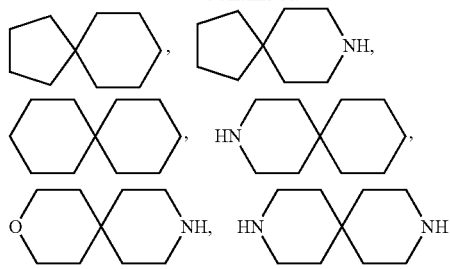

and the like.

Partially saturated spirocyclic group means that at least one ring in the spirocyclic group is an unsaturated cyclic group. The specific example comprises but is not limited to

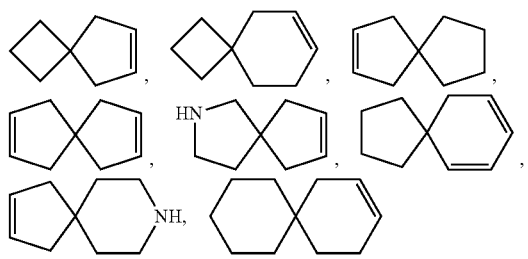

and the like.

The compound of the present invention can be prepared according to the following methods and/or other synthesis technologies known by those skilled in the art, but it should be understood that the preparation method is not limited to these exemplified methods.

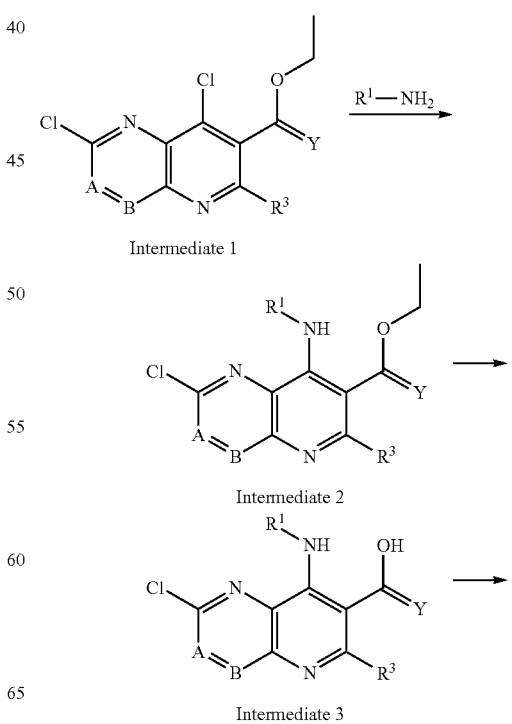

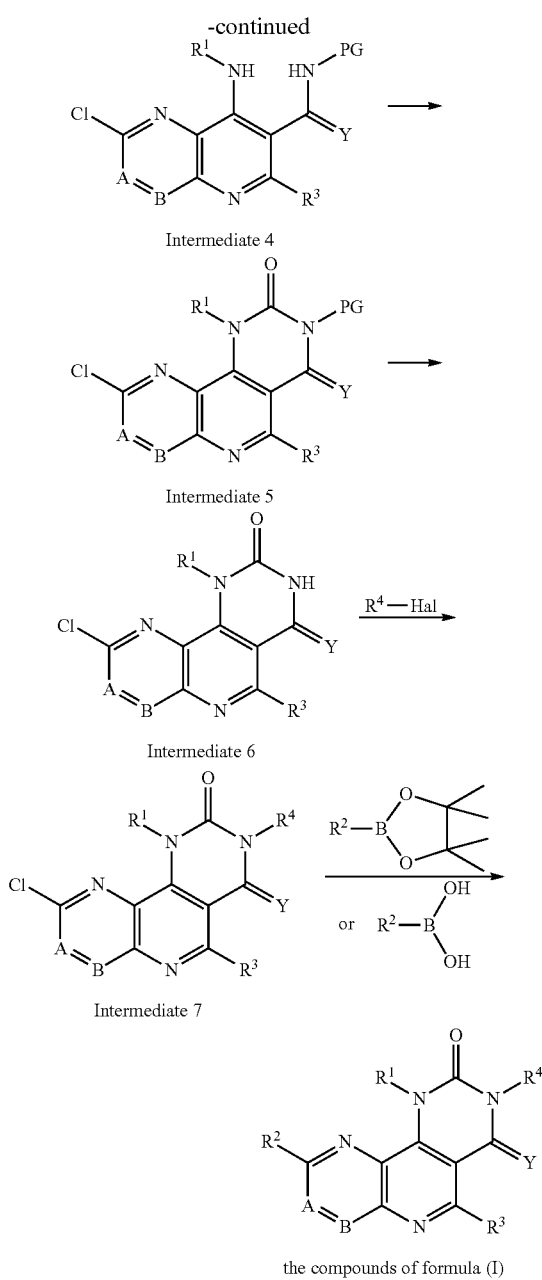

Intermediate 4

Intermediate 5

Intermediate 6

Intermediate 7 the compounds of formula (I)

Reaction Steps:
(1) Preparation of Intermediate 2

Intermediate 1 (made in laboratory) is added to a solution of $R^1$—$NH_2$ (1.5 eq.) and a suitable amount of base (e.g. potassium carbonate, sodium carbonate, sodium bicarbonate, potassium acetate and the like) in an alcoholic solvent (e.g. methanol, ethanol, isopropanol, tert-butanol and the like). The mixture is reacted under heating. The reaction is monitored by TLC. After the completion of the reaction, the reaction mixture is cooled at room temperature, rotary-evaporated to remove the alcoholic solvent, and separated to silicagel column chromatography or recrystallization to produce Intermediate 2.

(2) Preparation of Intermediate 3

Intermediate 2 is dissolved in a water-miscible solvent (e.g. methanol, ethanol, tetrahydrofuran or a mixture thereof). To the resulting mixture is added dropwise a solution of a base (3 eq.) (e.g. lithium hydroxide, potassium hydroxide, sodium hydroxide and the like) in water. After the completion of the dropwise addition, the resulting mixture is reacted at room temperature for 2-6 hours and rotary-evaporated to remove the organic solvent. After adding a suitable amount of water, the resulting mixture is adjusted with hydrochloric acid to a suitable pH until the product is completely separated out. The resulting product is filtered by suction and subjected to separated by silicagel column chromatography or recrystallization to produce Intermediate 3.

(3) Preparation of Intermediate 4

Intermediate 3 is suspended in a suitable amount of an organic solvent (e.g. sulfinyl chloride, toluene, chloroform, carbon tetrachloride and the like) and reacted for several hours. The resulting mixture is concentrated to remove the volatile substance, and then dispersed in a suitable amount of a polar solvent (e.g. tetrahydrofuran, ethyl acetate, methanol, ethanol, isopropanol, pyridine, acetone, triethylamine and the like). The temperature is controlled at about 0° C. To the resulting mixture is added a mixture of a suitable amount of a base solvent (e.g. methylamine, trimethylamine, diethylamine, triethylamine, diisopropylamine, ethylene diamine, triethanolamine and the like) and an amine containing a protection group (PG-$NH_2$). The reaction mixture is stirred at room temperature, and monitored by TLC. After the completion of the reaction, the reaction mixture is rotary-evaporated to remove the solvent, and separated by recrystallization or silicagel column chromatography to produce Intermediate 4.

(4) Preparation of Intermediate 5

Intermediate 4 is dispersed in a suitable amount of an ester solvent (e.g. ethyl chloroformate, methyl acetate, ethyl acetate, propyl acetate and the like). The resulting mixture is stirred under reflux. The reaction is monitored by TLC. After the completion of the reaction, the reaction mixture is rotary-evaporated to remove the volatile substance, and separated by silicagel column chromatography or recrystallization to produce Intermediate 5.

(5) Preparation of Intermediate 6

The amino protection group is removed under a reaction condition selected according to the protection group (PG) to produce Intermediate 6.

(6) Preparation of Intermediate 7

Intermediate 6, $R^4$-Hal (1.5 eq.) and a suitable amount of a base (e.g. potassium carbonate, sodium carbonate, sodium bicarbonate, potassium acetate and the like) are dissolved in a solvent. The mixture is stirred. The reaction is monitored by TLC. After the completion of the reaction, the reaction mixture is rotary-evaporated to remove the solvent, and separated by silicagel column chromatography or recrystallization to produce Intermediate 7.

(7) Preparation of the Present Compounds of Formula (I)

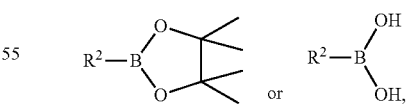

a suitable amount of a base (e.g. potassium carbonate, sodium carbonate, sodium bicarbonate, potassium acetate and the like), and a palladium agent and/or the corresponding phosphine ligand (e.g. tetrakis(triphenylphosphine)palladium and the like) is placed in a mixed solvent of an organic solvent (e.g. toluene, dioxane, dimethyl formamide, ethylene glycol dimethyl ether and the like) and water. The resulting mixture is reacted under heating in the nitrogen protection. The reaction is monitored by TLC. After the completion of the reaction, the reaction mixture is subjected to silicagel column chromatography to produce the present compound.

In the reaction equations, $R^1$, $R^2$, $R^3$, $R^4$, Y, A and B are defined as above, and Hal represents halogen, selected from F, Cl, Br and I.

For the above reactions, an acidic or base condition can be produced with an appropriate acid or base selected according to the specific protection agent. The base includes an organic base and an inorganic base, and the acid includes an organic acid and an inorganic acid.

The inorganic base is for example selected from, but not limited to, lithium hydroxide, potassium hydroxide, sodium hydroxide, magnesium hydroxide, calcium hydroxide, potassium carbonate, potassium bicarbonate, sodium carbonate, sodium bicarbonate and the like.

The organic base is for example selected from, but not limited to, an amine compound, e.g. methylamine, trimethylamine, diethylamine, triethylamine, diisopropylamine, ethylene diamine, triethanolamine, diisopropylethylamine, tributylamine, N,N-dimethylaniline and the like; basic amino acids, e.g. lysine, histidine and the like; quaternary ammonium bases, e.g. betanin, choline and the like; alkaloids, e.g. procaine, caffeine, ephedrine and the like; alkali metal alkoxides, e.g. sodium methoxide, potassium ethoxide, potassium tert-butoxide and the like; lithium compounds, e.g. butyl-lithium, lithium diisopropylamide (LDA), lithium bis(trimethylsilyl)amide (LiHMDS) and the like.

The inorganic acid is for example selected from, but not limited to, hydrobromic acid, hydrochloric acid, sulfuric acid, sulfurous acid, nitric acid, phosphoric acid and the like.

The organic base is for example selected from, but not limited to, methanesulfonic acid, 2-naphthalenesulfonic acid, benzenesulfonic acid, oxalic acid, 2,2-dichloroacetic acid, 2-hydroxyethanesulphonic acid, L-aspartic acid, maleic acid, ethanesulphonic acid, p-toluene sulfonic acid and the like.

The term "pharmaceutically acceptable salt" refers to a salt prepared from a suitable inorganic or organic cation (base) when the compound of formula (I) includes an acidic group (e.g. —COOH, —OH, $SO_3H$ and the like), including a salt formed with alkali metal or alkaline earth metal, an ammonium salt, and a salt formed with an nitrogen-containing organic base; as well as a salt prepared from a suitable inorganic or organic anion (acid) when the compound of formula (I) includes a basic functional group (e.g. —$NH_2$ and the like), including a salt formed with an inorganic acid, a salt formed with an organic carboxylic acid, and the like.

The stereoisomer of the compound of formula (I) of the present invention refers to an enantiomer existing when one or more asymmetric carbon atoms exist in the compound of formula (I) of the present invention; a cis/trans isomer existing when the compound contains a carbon-carbon double bond or a cyclic structure; a tautomer existing when the compound contains a ketone or an oxime, and the like. All of enantiomers, diastereomers, racemic isomers, cis-trans isomers, tautomers, geometric isomers, epimerides and mixture thereof are included within the scope of the present invention.

The term "solvate" of the compound of formula (I) of the present invention refers to a substance formed by associating with a solvent. The solvent may be an organic solvent (e.g. methanol, ethanol, propanol, acetonitrile, and the like), water, and the like. For example, the compound of formula (I) of the present invention can form an ethanolate with ethanol, or form a hydrate with water.

The present compound of formula (I), or a pharmaceutically acceptable salt, solvate or stereoisomer thereof is useful for treating and/or preventing proliferative diseases including cancer and non-cancer diseases, wherein the cancer disease is selected from a brain tumor, lung cancer, non-small cell lung cancer, squamous cell carcinoma, bladder cancer, stomach cancer, ovarian cancer, peritoneal cancer, pancreatic cancer, breast cancer, head and neck cancer, cervical cancer, endometrial cancer, colorectal cancer, liver cancer, kidney cancer, esophageal adenocarcinoma, esophageal squamous cell carcinoma, solid tumors, non-Hodgkin's lymphoma, glioma, glioblastoma multiforme, gliosarcoma, prostate cancer, thyroid carcinoma, genital tract carcinoma, carcinoma in situ, lymphoma, histiocytic lymphoma, neurofibromatosis, bone cancer, skin cancer, brain cancer, colon cancer, testicular cancer, small cell lung cancer, gastrointestinal stromal tumor, prostate tumor, mast cell tumor, multiple myeloma, melanoma, glioma, glioblastoma, astrocytoma, neuroblastoma, sarcomas; and the non-cancer disease is selected from a skin disease or benign prostate hyperplasia.

The present compound of formula (I), or a pharmaceutically acceptable salt, solvate or stereoisomer thereof can be made into pharmaceutical preparations with one or more pharmaceutically acceptable carriers. Said pharmaceutical preparations refer to conventional preparations in the clinical use, and can be orally or parenterally applied to patients in need of such treatment. For oral administration, they can be made into conventional solid preparations such as tablets, capsules, pills, granules, etc., as well as oral liquid preparations, such as oral solutions, oral suspensions, syrups, etc. For parenteral administration, they can be made into injections, including injection solution, a sterile powder for injection, concentrated solution for injection and suspension for injection. For rectal administration, they can be made into suppositories and the like. For transpulmonary administration, they can be made into inhalations or aerosols and the like. For topical or percutaneous administration, they can be made into ointments, pastes, creams, lotions, gels, powders, solutions or transdermal stickers and the like. These preparations can be prepared by a conventional method, adding pharmaceutically acceptable carriers such as excipients, binders, moistening agents, disintegrating agents, thickeners and the like.

The administration amount and frequency of the present compounds can be adjusted according to the judgment of the clinician or pharmacist, for example according to the patient's age, weight, the severity of the symptoms. Generally, the daily dose of the present compounds when administrated in a single dose or divided doses may be 20-500 mg, preferably 50-300 mg.

The present compound of formula (I), or a pharmaceutically acceptable salt, solvate or stereoisomer thereof can be used in combination with one or more anti-cancer agents and immunosuppressants. The anti-tumor agents and immunosuppressants are selected from anti-metabolites, including but not limited to, capecitabine, gemcitabine and pemetrexed disodium; growth factor inhibitors, including but not limited to, pazopanib, imatinib, erlotinib, lapatinib, gefitinib and vandetanib; antibodies, including but not limited to Herceptin and Avastin; mitotic inhibitors, including but not limited to paclitaxel, vinorelbine, docetaxel and doxorubicin; anti-tumor hormones, including but not limited to letrozole, tamoxifen, fulvestrant, flutamide and triptorelin; alkylating agents, including but not limited to cyclophosphamide, nitrogen mustard, melphalan, chlorambucil and carmustine; platinum metals, including but not limited to carboplatin, cisplatin and oxaliplatin; topoisomerase inhibitors, including but not limited to camptothecin, topotecan and irinotecan; immunosuppression categories, including but not limited to everolimus, sirolimus and temsirolimus; purine analogues, including but not limited to, 6-mercaptopurine, 6-thioguanine and azathioprine; antibiotics, including but not limited to rhzomorph D, daunorubicin, doxorubicin, mitoxantrone, bleomycin and plicamycin; adrenal cortex inhibitor, including but not limited to aminoglutethimide.

The beneficial effects of the present compounds will be further elaborated hereinafter. Other compounds of the present invention have the same beneficial effects as the compounds listed in the experiments, but it should not be understood that the present compounds only have the following beneficial effects.

The abbreviations in the following experiments have the following meanings:
HEPES: hydroxyethylpiperazine-ethane sulfonic acid;
Brij-35: Polyethylene glycol monododecyl ether;
EDTA: ethylenediaminetetraacetic acid;
EGTA: Ethylene glycol-bis-(2-aminoethylether)-N,N,N',N'-tetraacetic acid;
CHAPS: 3-((3-Cholamidopropyl)dimethylammonium)-1-propanesulfonate
DTT: dithiothreitol;
PIP2: phosphatidylinositol-4,5-bisphosphate;
ATP: adenosine triphosphate;
DMSO: dimethylsulfoxide;
DMF: dimethyl formamide;
Tween-20: Tween 20;
PEG: polyethylene glycol.

Assay 1-1: Kinase Selectivity of the Present Compound

Object: In this assay, the inhibitory activity of the test substance on the kinases listed in Table 3 was determined, and therefore the selectivity of the present compound was determined.

Test substance: Compound 5 according to the present invention, made in laboratory. Its chemical name and structure formula was shown in Example 1.

Method

Except for the BRAF V600E kinase in Table 3, the Mobility shift assay was used for other kinases.

1. Preparation of Agents:
   1.1 1-fold kinase buffer without $MnCl_2$: 50 mM HEPES, pH 7.5, 0.0015% Brij-35, 10 mM $MgCl_2$, 2 mM DTT.
   1.2 1-fold kinase buffer with $MnCl_2$: 50 mM HEPES, pH 7.5, 0.0015% Brij-35, 10 mM $MgCl_2$, 10 mM $MnCl_2$, 2 mM DTT.
   1.3 Termination solution: 100 mM HEPES, pH 7.5, 0.0015% Brij-35, 0.2% Coating Reagent#3, 50 mM EDTA.
   1.4 2.5-fold kinase solution: The kinase was added to the 1-fold kinase buffer to form a 2.5-fold kinase solution.
   1.5 2.5-fold substrate solution: FAM fluorescence-labelled polypeptide and ATP were added to the 1-fold kinase buffer to form a 2.5-fold substrate solution.

2. Preparation of 5-fold compound

The final test concentration of the compound was 10 µM at maximum. Firstly, a 50-fold concentration (i.e. 500 µM) was prepared with 100% DMSO. The compound was diluted with 100% DMSO by 5 folds at 5 concentrations (successively 500 µM, 100 µM, 20 µM, 4 µM, and 0.8 µM). After diluting with 1-fold kinase buffer by 10 folds, 5 µl of the samples were transferred to a 384-well reaction plate. Two negative control wells and two positive control wells were set at each line respectively. Replication was made in a 96-well plate in five concentrations of 5-fold compound. 10% DMSO was added to the positive control well, and 5 µl of EDTA (250 mM) was added to the negative control well.

3. Procedure
   3.1 To the 384-well reaction plate was added 5-fold compound dissolved in 10% DMSO at 5 µl/well.
   3.2 To the 384-well reaction plate was added 2.5-fold kinase solution at 10 µl/well. The plate was incubated at room temperature for 10 mins.
   3.3 To the 384-well reaction plate was added 2.5-fold substrate solution at 10 µl/well. The plate was incubated at 28° C. for a certain period.
   3.4 25 µl termination solution was added to terminate the reaction. The conversion was read from Caliper.

4. Inhibition rate calculation

Inhibition rate (%)=(maximum−sample value)/(maximum−minimum)×100 wherein:
maximum refers to the conversion at the DMSO control well,
minimum refers to the conversion at the control well without kinase.

Lanthascreen Analysis Method for the BRAF V600E Kinase

1. Preparation of Agents:
   1.1 2-fold kinase solution: using 1-fold kinase buffer to prepare 2-fold kinase solution, with a final concentration of 0.35 nM of BRAFV600E;
   1.2 4-fold substrate solution: using 1-fold kinase buffer to prepare 4-fold substrate solution, with a final substrate solution concentration of 0.2 µM of Fluorescein-MAP2K1 and 1.5 µM of ATP.

2. Preparation of 4-fold compound

The final test concentration of the compound was 10 µM at maximum. Firstly, a 100-fold concentration (i.e. 1000 µM) was prepared with 100% DMSO. The compound was diluted with 100% DMSO by 5 folds at 5 concentrations. The compound series was identical to that in the Mobility Shift Assay. After diluting with 1-fold kinase buffer by 25 folds, the resulting samples were shaked and mixed evenly on a plate-shaker for 10 mins.

3. Procedure
   3.1 To the 384-well reaction plate was added 4-fold compound dissolved in 10% DMSO at 2.5 l/well;
   3.2 To the 384-well reaction plate was added 2-fold kinase solution at 5 µl/well, and to the negative control wells were added 1-fold kinase buffer. The samples were shaked, mixed evenly, and kept standing at room temperature.
   3.3 To the 384-well reaction plate was added 4-fold substrate solution at 2.5 µl/well. The plate was reacted, shaked, mixed evenly and incubated at room temperature for one hour;
   3.4 Reaction result detection: 2-fold detection solution was prepared, with a final concentration of 2 nM of Antibody and 10 mM of EDTA. 10 µl of the detection solution was transferred to the 384-well plate to terminate the reaction. The plate was gently shaked on a plate-shaker for 30 mins.

4. Inhibition rate calculation

Fluorescence values of the sample were read from Victor, excition at 340 nm and adsorption at 520 nm.

Inhibition rate (%)=(maximum−sample value)/(maximum−minimum)×100 wherein:
maximum refers to the reading at the control well without kinase,
minimum refers to the reading at the DMSO control well.
The data was input into MS Excel and subjected to a curve fitting with Graphpad 5.0

Result

TABLE 3

Inhibitory activity of Compound 5 of the present invention on kinases, $IC_{50}$ (nM)

| Kinase | $IC_{50}$ (nM) |
|---|---|
| ABL | >10000 |
| AKT1 | >10000 |
| ALK | 1170 |
| AMPKa1 | >10000 |
| AURA | >10000 |
| AXL | 2138 |
| BRAF V600E | >10000 |
| CAMK2a | >10000 |
| CDK2 | >10000 |
| CKIT | >10000 |
| CK1d | >10000 |
| CMET | >10000 |
| CHK1 | >10000 |
| CSK | >10000 |
| DYRK1b | >10000 |
| EGFR | >10000 |
| EphA1 | 1467 |
| ERK2 | >10000 |
| FES | >10000 |
| FGFR1 | >10000 |
| FLT3 | 6247 |
| GSK3β | >10000 |
| IGF1R | >10000 |
| IKKB | >10000 |
| IRAK4 | >10000 |
| JAK2 | >10000 |
| JAK3 | >10000 |
| JNK2 | >10000 |
| KDR | >10000 |
| LCK | 1126 |
| LYNa | 1370 |
| MAPKAPK2 | >10000 |
| MARK1 | >10000 |
| MSK1 | >10000 |
| MST2 | >10000 |
| NEK2 | >10000 |
| p38a | >10000 |
| P70s6k | >10000 |
| PAK2 | >10000 |
| PDK1 | >10000 |
| PDGFRb | >10000 |
| PIM1 | >10000 |
| PKCa | >10000 |
| PKACa | >10000 |
| PKD1 | 2407 |
| ROCK2 | >10000 |
| RSK2 | >10000 |
| SGK | >10000 |
| SRC | 842 |
| SYK | >10000 |
| TAOK2 | >10000 |
| Tie2 | 2430 |
| ZAP70 | >10000 |

Summary

It can be seen from Table 3 that Compound 5 of the present invention had inferior $IC_{50}$ for the listed kinases, most of which were >10000 nM. This showed that Compound 5 of the present invention had no inhibitory activity for those kinases. In the following assays, it could be demonstrated that Compound 5 of the present invention had good inhibitory activity on PI3k kinase and mTOR kinase. This showed that Compound 5 of the present invention had good selectivity and high inhibitory activity on PI3k kinase and mTOR kinase.

Assay 1-2: In Vitro Enzymatic Inhibitory Activity of the Present Compound

Test substances: the compounds of the present invention, made in laboratory. Their chemical names and structure formulae were shown in Examples.

mTOR Enzymatic Assay
1. Preparation of Agents:
   1.1 1-fold kinase buffer: 50 mM HEPES, pH 7.5, 10 mM $MgCl_2$, 1 mM EGTA, 3 mM $MnCl_2$, 0.01% Tween-20, 2 mM DTT;
   1.2 4-fold kinase solution: mTOR kinase was added to 1-fold kinase buffer to form 4-fold kinase solution with a final concentration of 2.5 nM;
   1.3 2-fold substrate and ATP solution: the substrate 4EBP1 and ATP were added to 1-fold kinase buffer to form 2-fold substrate solution with final concentration of 50 nM of 4EBP1 and 10.8 μM of ATP;
   1.4 4-fold test substance solutions: 100-fold test substance solutions in different gradient concentrations were formulated with 100% DMSO, and diluted by 25 folds with 1-fold kinase buffer to form 4-fold test substance solutions in different gradient concentrations.
   1.5 Preparation of detection solution: a detection solution containing 2-fold final concentrations of EDTA and 4EBP1 phosphorylated antibody was formulated, wherein the final concentration for EDTA was 8 mM, and the final concentration for the 4EBP phosphorylated antibody was 2 nM.
2. Procedure
   2.1 To each well of a 384-well plate was added 2.5 μL of the 4-fold test substance solutions in gradient concentrations. The replication was made.
   2.2 To each well was added 2.5 μL of 4-fold kinase solution, and then the plate was incubated for 10 mins;
   2.3 Then to each well was added 5 μL/of 2-fold substrate and ATP solution, and then the plate was incubated at room temperature for 1 hour;
   2.4 Finally, 10 μL of the detection solution was added to terminate the reaction. After 60 mins, the data Lance signal (665 nM) was read from Envision.
3. Data treatment Inhibition rate (%)=(sample value−minimum)/(maximum−minimum)×100 wherein:
maximum refers to the reading at the DMSO control well.
minimum refers to the reading at the control well without kinase,
The data was input into Graphpad Prism 5.0 to plot and obtain the curve and $IC_{50}$ value.

PI3Kα Enzymatic Assay
1. Preparation of Agents:
   1.1 1-fold kinase buffer: 50 mM HEPES, pH 7.5, 3 mM $MgCl_2$, 1 mM EGTA, 100 mM NaCl, 0.03% CHAPS, 2 mM DTT);
   1.2 4-fold kinase solution: PI3Kα kinase was added to 1-fold kinase buffer to form 4-fold kinase solution with a final concentration of 1.65 nM;
   1.3 2-fold substrate and ATP solution: the substrate PIP2 and ATP were added to 1-fold kinase buffer to form 2-fold substrate solution with final concentration of 50 μM of PIP2 and 25 μM of ATP;
   1.4 4-fold test substance solutions: 100-fold test substance solutions in different gradient concentrations were formulated with 100% DMSO, and diluted by 25 folds with 1-fold kinase buffer to form 4-fold test substance solutions in different gradient concentrations.
   1.5 Kinase-Glo reagent kit, which was placed to warm up to room temperature.

2. Procedure
  2.1 To each well of a 384-well plate was added 2.5 μL of the 4-fold test substance solutions in gradient concentrations;
  2.2 To each well was added 2.5 μL of 4-fold kinase solution, and then the plate was incubated for 10 mins;
  2.3 Then to each well was added 5 μL of 2-fold substrate and ATP solution, and then the plate was incubated at room temperature for 1 hour;
  2.4 Finally, 10 μL of the detection solution was added to terminate the reaction. After 15 mins, the data Lance signal (665 nM) was read from Envision.
3 Data treatment Inhibition rate (%)=100−(sample value−minimum)/(maximum−minimum)×100 wherein:
maximum refers to the reading at the control well without kinase,
minimum refers to the reading at the DMSO control well,
The data was input into Graphpad Prism 5.0 to plot and obtain the curve and $IC_{50}$ value.
Result

TABLE 4

In vitro enzymatic activity of the present compounds ($IC_{50}$)

| Test substance | PI3Kα (nM) | mTOR (nM) |
|---|---|---|
| Compound 2 | 79 | 57 |
| Compound 5 | 7.8 | 2.5 |
| Compound 6 | 65.8 | 5.4 |
| Compound 17 | 40.7 | 39.3 |
| Compound 20 | 15.2 | 2.66 |
| Compound 30 | 15.0 | 1.12 |

Summary

It can be seen from Table 4 that the present compounds had good inhibitory activity on both PI3Kα and mTOR kinases.

Assay 1-3: Drug Target Radioligand Competitive Binding Assay of the Present Compound Object: An investigation was made to determine the competitive binding capability of the test substance on the non-kinase drug target radioligand listed in Table 5 when the test substance was in a concentration of 10 μM (Broad ligand profiling completed Lead Profiling Screen). If the inhibitory rate of the test substance on these targets was more than 50%, it was considered that the test substance had an inhibitory activity on the targets; if the inhibitory rate of the test substance on these targets was less than 50%, it was considered that the test substance had no inhibitory activity on the targets, showing the test substance had no selectivity on these targets, and no potential side-effect was present.

Test substance: Compound 5 according to the present invention, made in laboratory. Its chemical name and structure formula was shown in Example 1.

Method

Radioligand Binding Assay

Refer to the official website of Eurofins Panlabs, an international facilitator providing the drug product testing solutions, for the specific method and conditions.

The test substance concentration was 10 μM, and replication was made. With radio-labeling the ligands, the inhibitory rates of the test substance on the target ligands listed in Table 5 were detected.

Result

TABLE 5

Ligand competitive binding inhibitory rate of Compound 5 of the present invention (%)

| No. | Ligand competitive binding assay | batch | Species genus | Replicates | Test substance concentration (μM) | Inhibitory rate (%) |
|---|---|---|---|---|---|---|
| 200510 | Adenosine $A_1$ | 324458 | Human | 2 | 10 | 20 |
| 200610 | Adenosine $A_{2A}$ | 324459 | Human | 2 | 10 | 0 |
| 200720 | Adenosine $A_3$ | 324460 | Human | 2 | 10 | 11 |
| 203100 | Adrenergic $\alpha_{1A}$ | 324612 | rat | 2 | 10 | 13 |
| 203200 | Adrenergic $\alpha_{1B}$ | 324435 | rat | 2 | 10 | 21 |
| 203400 | Adrenergic $\alpha_{1D}$ | 324436 | Human | 2 | 10 | 9 |
| 203620 | Adrenergic $\alpha_{2A}$ | 324528 | Human | 2 | 10 | 19 |
| 204010 | Adrenergic $\beta_1$ | 324529 | Human | 2 | 10 | 0 |
| 204110 | Adrenergic $\beta_2$ | 324530 | Human | 2 | 10 | 17 |
| 285010 | Androgen (Testosterone) AR | 324661 | rat | 2 | 10 | 30 |
| 212510 | Bradykinin $B_1$ | 324624 | Human | 2 | 10 | 0 |
| 212620 | Bradykinin $B_2$ | 324481 | Human | 2 | 10 | 24 |
| 214510 | Calcium Channel L-Type, Benzothiazepine | 324455 | rat | 2 | 10 | 15 |
| 214600 | Calcium Channel L-Type, Dihydropyridine | 324456 | rat | 2 | 10 | 56 |
| 216000 | Calcium Channel N-Type | 324576 | rat | 2 | 10 | −22 |
| 217030 | Cannabinoid $CB_1$ | 324454 | Human | 2 | 10 | 25 |
| 219500 | Dopamine $D_1$ | 324450 | Human | 2 | 10 | 21 |
| 219700 | Dopamine $D_{2S}$ | 324451 | Human | 2 | 10 | 14 |
| 219800 | Dopamine $D_3$ | 324452 | Human | 2 | 10 | 15 |
| 219900 | Dopamine $D_{4.2}$ | 324453 | Human | 2 | 10 | 12 |
| 224010 | Endothelin $E_{TA}$ | 324526 | Human | 2 | 10 | 3 |
| 224110 | Endothelin $E_{TB}$ | 324527 | Human | 2 | 10 | 7 |
| 225510 | Epidermal Growth Factor (EGF) | 324648 | Human | 2 | 10 | 11 |

TABLE 5-continued

Ligand competitive binding inhibitory rate of Compound 5 of the present invention (%)

| No. | Ligand competitive binding assay | batch | Species genus | Replicates | Test substance concentration (μM) | Inhibitory rate (%) |
|---|---|---|---|---|---|---|
| 226010 | Estrogen ERα | 324629 | Human | 2 | 10 | 17 |
| 226600 | $GABA_A$, Flunitrazepam, Central | 324466 | rat | 2 | 10 | 34 |
| 226500 | $GABA_A$, Muscimol, Central | 324465 | rat | 2 | 10 | 18 |
| 228610 | $GABA_{B1A}$ | 324650 | Human | 2 | 10 | 15 |
| 232030 | Glucocorticoid | 324474 | Human | 2 | 10 | −4 |
| 232700 | Glutamate, Kainate | 324486 | rat | 2 | 10 | 35 |
| 232810 | Glutamate, NMDA, Agonism | 324487 | rat | 2 | 10 | 29 |
| 232910 | Glutamate, NMDA, Glycine | 324488 | rat | 2 | 10 | 29 |
| 233000 | Glutamate, NMDA, Phencyclidine | 324449 | rat | 2 | 10 | 8 |
| 239610 | Histamine $H_1$ | 324532 | Human | 2 | 10 | 10 |
| 239710 | Histamine $H_2$ | 324524 | Human | 2 | 10 | −2 |
| 239820 | Histamine $H_3$ | 324615 | Human | 2 | 10 | 16 |
| 241000 | Imidazoline$_{I2}$, Central | 324467 | rat | 2 | 10 | 0 |
| 243520 | Interleukin IL-1 | 324484 | mouse | 2 | 10 | 11 |
| 250460 | Leukotriene, Cysteinyl $CysLT_1$ | 324574 | Human | 2 | 10 | −1 |
| 251600 | Melatonin $MT_1$ | 324686 | Human | 2 | 10 | 17 |
| 252610 | Muscarinic $M_1$ | 324607 | Human | 2 | 10 | 18 |
| 252710 | Muscarinic $M_2$ | 324448 | Human | 2 | 10 | −4 |
| 252810 | Muscarinic $M_3$ | 324447 | Human | 2 | 10 | 13 |
| 257010 | Neuropeptide Y $Y_1$ | 324522 | Human | 2 | 10 | 3 |
| 257110 | Neuropeptide Y $Y_2$ | 324523 | Human | 2 | 10 | 10 |
| 258590 | Nicotinic Acetylcholine | 324520 | Human | 2 | 10 | 7 |
| 258700 | Nicotinic Acetylcholine α1, Bungarotoxin | 324521 | Human | 2 | 10 | 4 |
| 260130 | Opiate $\delta_1$ (OP1, DOP) | 324663 | Human | 2 | 10 | 4 |
| 260210 | Opiate $_\kappa$(OP2, KOP) | 324533 | Human | 2 | 10 | 10 |
| 260410 | Opiate $_\mu$(OP3, MOP) | 324534 | Human | 2 | 10 | 2 |
| 264500 | Phorbol Ester | 324468 | mouse | 2 | 10 | 27 |
| 265010 | Platelet Activating Factor (PAF) | 324540 | Human | 2 | 10 | 20 |
| 265600 | Potassium Channel [$K_{ATP}$] | 324535 | Human | 2 | 10 | 11 |
| 265900 | Potassium Channel hERG | 324469 | Human | 2 | 10 | 2 |
| 268420 | Prostanoid $EP_4$ | 324463 | Human | 2 | 10 | 19 |
| 268700 | Purinergic $P_{2X}$ | 324656 | rabbit | 2 | 10 | 9 |
| 268810 | Purinergic $P_{2Y}$ | 324657 | rat | 2 | 10 | 9 |
| 270000 | Rolipram | 324470 | rat | 2 | 10 | 20 |
| 271110 | Serotonin (5-Hydroxytryptamine) $5-HT_{1A}$ | 324438 | Human | 2 | 10 | 25 |
| 271700 | Serotonin (5-Hydroxytryptamine) $5-HT_{2B}$ | 324441 | Human | 2 | 10 | 13 |
| 271910 | Serotonin (5-Hydroxytryptamine) $5-HT_3$ | 324620 | Human | 2 | 10 | 8 |
| 278110 | Sigma$_{\sigma 1}$ | 324471 | Human | 2 | 10 | 13 |
| 279510 | Sodium Channel, Site$_2$ | 324464 | rat | 2 | 10 | 7 |
| 255520 | Tachykinin $NK_1$ | 324539 | Human | 2 | 10 | 20 |
| 285900 | Thyroid Hormone | 324689 | rat | 2 | 10 | 9 |
| 220320 | Transporter, Dopamine (DAT) | 324462 | Human | 2 | 10 | 1 |
| 226400 | Transporter, GABA | 324538 | rat | 2 | 10 | 12 |
| 204410 | Transporter, Norepinephrine (NET) | | Human | 2 | 10 | −5 |
| 274030 | Transporter, Serotonin (5-Hydroxytryptamine) (SERT) | 324660 | Human | 2 | 10 | 6 |

Summary

It could be seen from Table 5 that the inhibitory rates of Compound 5 of the present invention on the listed non-kinase drug target ligands were less than 50%, showing no inhibitory action. It demonstrated that Compound 5 of the present invention had very good selectivity and had a good inhibitory action only on the kinase target.

Assay 2: In Vitro Cytological Inhibitory Activity of the Present Compound

Test substances: the compounds of the present invention, made in laboratory. Their chemical names and structure formulae were shown in Examples.

The following cell lines were used in the assay:

A549: Human lung cancer cell line;
U87MG: Human brain astrocytoblast cell line;

PC-3: Human prostatic carcinoma cell line;
SKOV-3: Human ovarian cancer cell line;
Lovo: Human colon carcinoma cell line;
HCT116: Human colon carcinoma cell line;
BT474: Human mammary gland tumor cell line;
786-O: Human suprarenal epithelioma cell line;
MCF-7: Human breast carcinoma cell line;
A498: Human renal carcinoma cell line.

Method

1. Preparation of agents and compounds:
   1.1 Preparation of phosphoric acid buffering solution (PBS): 8 g NaCl, 0.2 g KCl, 1.44 g $Na_2HPO_4$ and 0.24 g $KH_2PO_4$ were weighed and added to 800 mL ultrapure water. The mixture was adjusted to pH=7.4, and ultrapure water was added to the metered volume of IL. Then the autoclaving was conducted for 20 mins.
   1.2 Preparation of XTT detection working solution: 100 mg (2,3-Bis-(2-methoxy-4-nitro-5-sulfophenyl)-2H-tetrazolium-5-carboxanilide); 2,3-bis(2-methoxy-4-nitro-5-sulfophenyl)-5-[(phenylamino)carbonyl]-2H-tetrazolium hydroxide (XTT) powder was weighed, and dissolved under protection from light 300 mL of phenol red-free and serum-free RPMI1640 culture, which had been warmed up to 50° C. The resulting mixture was filtered, packaged and used immediately or in one week. The complete process was conducted under protection from light.
   1.3 Preparation of the test compound
      Preparation of the stock solution of the test compound: The test compound powder was dissolved in DMSO in a concentration of 10 mM.
      Preparation of the gradiently diluted solution of the test compound: 10 mM of the stock solution of the test compound was successively and gradiently diluted with DMSO by 4 folds for 10 concentrations. Then, 2 μL of the DMSO diluted compounds were respectively added to 998 μL of the cultures containing 10% fetal bovine serum (FBS). The maximum concentration of the test substance was 20 μM, and the concentration of DMSO was 0.2%. There were 10 gradient concentrations in total.

2. Cell culturing:
   2.1 Cell resuscitation:
      A cell freezing tube was taken from liquid nitrogen, and placed in a water bath of 37° C. to 39° C. to thaw the cells quickly.
      A frozen stock solution was transferred to a sterile 15 mL centrifuge tube. A culture medium, having a volume 10-fold larger than the frozen stock solution, was added. The mixture was centrifugated at 1000 rpm at 4° C. for 5 mins. The culture medium in the centrifuge tube was discarded, a culture medium containing 10% FBS was added to resuspend the cells, and the resulting mixture was transferred to a culture flask, and the culture medium was changed on the next day.
   2.2 Cell passage
      The cells in the logarithmic growth phase were taken and the culture medium was removed therefrom. An appropriate volume of PBS was added to wash the cells once. Then an appropriate volume of a digestion solution containing 0.25% of pancreozyme and 0.02% of EDTA was added. The culture medium was placed at 37° C. for 2-5 mins. The digestion solution was discarded, and the cells were washed with PBS once. A suitable volume of a culture medium containing 10% FBS was added to terminate the digestion. The digested cells were gently blown with a pipet and prepared into a cell suspension for passage and assay.
   2.3 Cell cryopreserving
      The cells in the logarithmic growth phase were taken and digested with a digestion solution containing 0.25% pancreozyme and 0.02% EDTA. The digested cells were prepared into a cell suspension. The cell suspension was centrifugated at 1000 rpm at 4° C. for 5 mins. The culture medium was discarded, and a freezing stock solution containing 10% DMSO and 90% FBS was added to re-suspend the cells. The cells were sub-packaged in the freezing tubes with $2 \times 10^6$ cells per tube. The freezing tubes were placed in a programmed cell freezing box. After being placed at −80° C. for 24 hrs, the freezing tubes were transferred into liquid nitrogen for cryopreserving.

3. Cell plating
   3.1 Preparation of cell suspension: The culture medium was removed from the culture flask, and the cells were rinsed twice with PBS. The pancreozyme was added to digest the cells. The cells were collected by centrifuge, and resuspended with a culture medium containing 10% FBS (fetal bovine serum). The cells were counted and adjusted to an appropriate concentration (the cell viability should be larger than 90%); and the cell concentration was $5 \times 10^4$/mL;
   3.2 The cell suspension was added to a 96-well plate with 100 μl per cell. The plate was placed at 37° C. in a cell incubator (5% $CO_2$) overnight.

4. Treatment
   To the cell culture plate was added the diluted test compounds in three replications at 100 μl per well. The final volume was 200 μl. The starting concentration was 10 μM with 4-fold dilution. There were 10 gradient concentrations in total. The plate was placed in a CO2 cell incubator for 72 hrs.

5. Cell viability detection with XTT
   The culture medium was removed, and an XTT detection working solution was added at 150 μL per well. The plate was placed at 37° C. in a $CO_2$ cell incubator for 2 hrs. The plate was placed in a microplate reader for the light absorption at 450 nm.

6. Data treatment
   1) Inhibition rate (%)=(reading at the well for solvent control−reading at the well for test substance)/(reading at the well for solvent control−reading at the well for blank control)×100
   2) The data was input into Graphpad Prism 5.0 to plot and obtain the curve and $IC_{50}$ value.

Result

TABLE 6

In vitro cytological activity of the present compound ($IC_{50}$, nM)

| Test substance | U87MG | A549 | PC-3 | SKOV-3 | Lovo |
|---|---|---|---|---|---|
| Compound 5 | 29.48 | 63.16 | 33.73 | 51.17 | 50.15 |

TABLE 7

In vitro cytological activity of the present compound ($IC_{50}$, nM)

| Test substance | HCT116 | BT474 | 786-O | MCF-7 | A498 |
|---|---|---|---|---|---|
| Compound 5 | 100.2 | 33.66 | 65.65 | 28.22 | 83.67 |

TABLE 8

In vitro cytological activity of the present compound ($IC_{50}$, nM)

| Test substance | U87MG | A549 | PC-3 | SKOV-3 |
|---|---|---|---|---|
| Compound 6 | 37.65 | 89.53 | 35.81 | 63.06 |

TABLE 9

In vitro cytological activity of the present compound ($IC_{50}$, nM)

| Test substance | U87MG | A549 | PC-3 | SKOV-3 |
|---|---|---|---|---|
| Compound 30 | 28.30 | 106.6 | 25.65 | 57.16 |

Summary

It could be seen from Tables 6-9 that the present compounds could effectively inhibit the proliferation of the cells U87MG, A549 and the like.

Assay 3: In Vivo Pharmacokinetics Assay of the Present Compound in Rat

Test animals: male SD rats, weighing 190-260 g. Intravenous bolus injection (I.V.) and gavage (P.O.) administrations were each applied to three rats.

Test substances: the compounds of the present invention, made in laboratory. Their chemical names and structure formulae were shown in Examples.

Compound 5, for both I.V and P.O administrations, was solubilized with a solution of 30% DMF+50% PEG400+20% (0.9% sodium chloride injection)(the pH being adjusted with a suitable amount of an aqueous hydrochloric acid solution (2 mol/L)).

Compound 6, for both I.V and P.O administrations, was solubilized with a solution of 30% DMF+30% PEG400+5%0.1 mol/lhydrochloric acid+45% normal saline.

Compound 30 for I.V administration was solubilized with a solution of 30% DMF+50% PEG400+20% normal saline; Compound 30 for P.O administration was solubilized with a solution of 5% DMSO+30% polyoxyethylene castor oil+65% normal saline.

Compound 30 hydrochloride for I.V administration was solubilized with a solution of 30% DMF+50% PEG400+20% sterile water for injection.

Method

1. Administration: The Administration Manner and Dosage for the Test Substances were Shown in Tables 10-1 and 10-2.

TABLE 10-1 administration manner, dosage and volume for the test substances

| | I.V | | P.O | |
|---|---|---|---|---|
| Test substance | Dosage (mg/kg) | Volume (mL/kg) | Dosage (mg/kg) | Volume (mL/kg) |
| Compound 5 | 2 | 2 | 4 | 4 |
| Compound 6 | 2 | 2 | 4 | 4 |
| Compound 30 | 2 | 2 | — | — |
| Compound 30 hydrochloride | 2 | 2 | — | — |

TABLE 10-2

| | P.O | |
|---|---|---|
| Test substance | Dosage (mg/kg) | Volume (mL/kg) |
| Compound 30 | 4 | 10 |

2. Blood sampling:

I.V blood sampling time point: 0.083 h, 0.25 h, 0.5 h, 1 h, 2 h, 4 h, 6 h, 8 h and 24 h after the administration, P.O blood sampling time point: 0.17 h, 0.5 h, 1 h, 2 h, 4 h, 6 h, 8 h and 24 h after the administration.

About 100 µl of whole blood was taken at each time point, anticoagulated with heparin sodium, and centrifugated at 8,000 rpm in a high-speed centrifuge for 6 minutes to separate plasma, and the resulting plasma was frozen at −80° C. in a refrigerator.

3. Plasma sample analysis:

The plasma sample was treated with a liquid-liquid extraction. 20 µL of plasma was taken. A solution of BEZ-235 (Novartis, Phase II) in tertbutylmethylether (600 µL, 10 ng/mL) was added as internal standard. The mixture was rotated vertically at 1500 rpm for 10 mins and then centrifugated at 12000 rpm for 5 mins. 400 µL of the supernate was taken and dried under nitrogen. The dried substance was redissolved in 200 µL methanol:water (7:3, V/V) for LC-MS/MS analysis.

Result

See the following Tables 11, 12-1, 12-2.

Calculation $$\text{Absolute bioavailability } F\% = [AUC]_{last} (P.O)*Dose (I.V)/[AUC]_{last}(I.V)*Dose(P.O)$$

TABLE 11

The evaluation results of pharmacokinetics of the present compounds in rats (I.V)

| Test substance | $AUC_{last}$ (h*ng/mL) | $AUC_{inf}$ (h*ng/mL) | Vss (L/kg) | $T_{1/2}$ (h) | CL (L/kg/h) |
|---|---|---|---|---|---|
| Compound 5 | 9130 | 9361 | 1.26 | 4.72 | 0.21 |
| Compound 30 | 3052 | 3070 | 1.85 | 3.89 | 0.66 |
| Compound 30 hydrochloride | 1679 | 1691 | 2.49 | 3.04 | 1.18 |
| Compound 6 | 4447 | 4468 | 1.95 | 3.15 | 0.46 |

TABLE 12-1

The evaluation results of pharmacokinetics of the present compounds in rats (P.O)

| Test substance | $AUC_{last}$ (h*ng/mL) | $AUC_{inf}$ (h*ng/mL) | Cmax (ng/mL) | Tmax (h) | $T_{1/2}$ (h) | F % |
|---|---|---|---|---|---|---|
| Compound 5 | 2549 | 2592 | 205 | 6 | 5.77 | 14.0 |
| Compound 6 | 10154 | 10301 | 1120 | 2.0 | 3.92 | 115 |

TABLE 12-2

The evaluation results of pharmacokinetics of the present compounds in rats (P.O)

| Test substance | $AUC_{last}$ (h * ng/mL) | $AUC_{inf}$ (h * ng/mL) | Cmax (ng/mL) | Tmax (h) | $T_{1/2}$ (h) | F % |
|---|---|---|---|---|---|---|
| Compound 30 | 654 | 785 | 54.8 | 2.0 | 9.42 | 12.8 |

$AUC_{last}$ represents the area under the plasma concentration-time curve 0→t
$AUC_{inf}$ represents the area under the plasma concentration-time curve 0→∞
CL represents the clearance
Vss represents the apparent volume of distribution
$T_{1/2}$ represents the half-life
$T_{max}$ represents the time for reaching the maximum drug concentration in plasma
$C_{max}$ represents the maximum drug concentration in plasma
F % represents the absolute bioavailability Summary It could be seen from Tables 11, 12-1 and 12-2 that the present compounds had good pharmacokinetics in both P.O and I.V administrations.

EXAMPLES

The above contents of the present invention will be described in further detail by the following Examples, but this should not be construed that the invention is limited to the following Examples.

The abbreviations in the following Examples are defined as follows:

EtOAc: ethyl acetate;
EA: ethyl acetate;
PE: petroleum ether;
HATU: 2-(7-azabenzotriazole)-N,N,N',N'-tetramethyluronium hexafluorophosphate;
DCM: dichloromethane;
DMF: dimethyl formamide.

5-(4,4,5,5-tetramethyl-1,3,2-dioxaborolan-2-yl)pyridin-2-amine, made in laboratory. The preparation method was as follows:

2-amino-5-bromopyridine (5.1 g, 30 mmol), bis(pinacolato)diboron (10.7 g, 45 mmol), potassium carbonate (8.3 g, 60 mmol), and tetrakis(triphenylphosphine)palladium (693 mg, 0.6 mmol) were added to 150 mL dioxane and 2 mL water. The resulting mixture was reacted under reflux in the nitrogen protection for 4 hours, cooled to room temperature, filtered and concentrated. The crude product was dissolved in 300 mL dichloromethane, washed with water, dried over anhydrous sodium sulfate, and concentrated. When only a small amount of solvent retained, petroleum ether was added thereto. A yellow solid was separated out and filtered to obtain a product (1.8 g).

5-(4,4,5,5-tetramethyl-1,3,2-dioxaborolan-2-yl)pyrimidin-2-amine, commercially available from PharmaBlock (Nanjing) R&D Co. Ltd.;

(2-methoxypyrimidin-5-yl)boric acid, commercially available from J&K Scientific Ltd.;

(6-methoxypyridin-3-yl)boric acid, commercially available from J&K Scientific Ltd.;

5-(4,4,5,5-tetramethyl-1,3,2-dioxaborolan-2-yl)-1H-pyrrolo[2,3-b]pyridine, commercially available from PharmaBlock (Nanjing) R&D Co. Ltd.;

Example 1

Preparation of 9-(6-aminopyridin-3-yl)-1-(3-(trifluoromethyl)phenyl)pyrimido[5,4-c][1,5]naphthyridine-2,4(1H,3H)-dione (Compound 5)

1) ethyl 6-chloro-4-((3-(trifluoromethyl)phenyl)amino)-1,5-naphthyridine-3-carboxylate

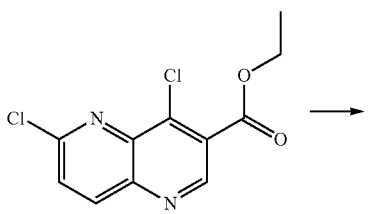

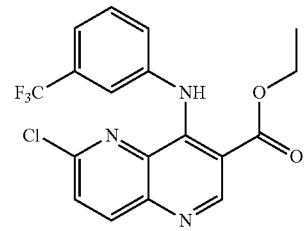

4,6-dichloro-1,5-naphthyridine-3-carboxylate ethyl (5.4 g, 20 mmol)(prepared according to page 38, WO2013/2071698), meta-trifluoromethylaniline (4.5 g, 28 mmol) and potassium carbonate (5.5 g, 40 mmol) were added to 150 mL tert-butanol. The resulting mixture was added to 90° C. and reacted for 18 hrs. The reaction was cooled to room temperature and rotary-evaporated to dryness. 300 mL water was added to the resulting solid, which was filtered, and washed with ethyl acetate and petroleum ether (1/20, 50 mL) to obtain a yellow solid of 6-chloro-4-((3-(trifluoromethyl)phenyl)amino)-1,5-naphthyridine-3-carboxylate ethyl (6.0 g).

2) 6-chloro-4-((3-(trifluoromethyl)phenyl)amino)-1,5-naphthyridine-3-carboxylic acid

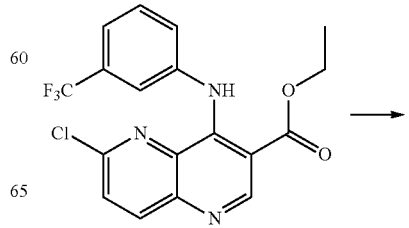

-continued

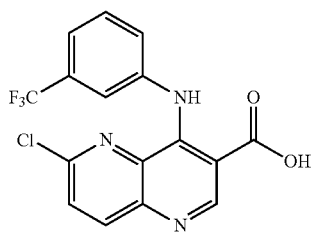

ethyl 6-chloro-4-((3-(trifluoromethyl)phenyl)amino)-1,5-naphthyridine-3-carboxylate (3.95 g, 10 mmol) was dissolved in 50 mL methanol and 50 mL tetrahydrofuran. To the resulting mixture was added dropwise a solution of lithium hydroxide (1.26 g, 30 mmol) in water (50 mL). After the completion of the dropwise addition, the resulting mixture is reacted at room temperature for 4 hrs. The reaction was concentrated, and 200 mL water was added. The resulting mixture was adjusted with hydrochloric acid to pH=3. The solid was separated, and dried in vacuum to obtain a yellow solid (3.6 g).

3) N-(4-methoxybenzyl)-6-chloro-4-((3-(trifluoromethyl)phenyl)amino)-1,5-naphthyridine-3-carboxamide

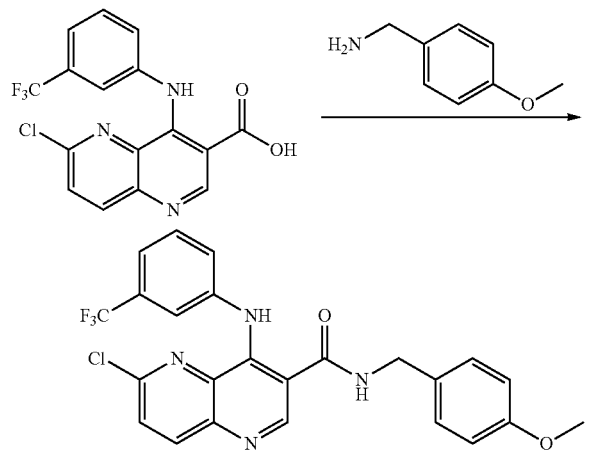

6-chloro-4-(3-(trifluoromethyl)phenylamino)-1,5-naphthyridine-3-carboxylic acid (3.6 g, 9.8 mmol) was suspended in 50 mL sulfinyl chloride. The resulting mixture was heated under stirring to 75° C. and reacted for 4 hrs while keeping at the same temperature. The reaction was naturally cooled to room temperature, and concentrated to obtain a yellow solid. The resulting solid was dispersed in 100 mL tetrahydrofuran. To the resulting mixture was added dropwise a mixture of triethylamine (3.03 g, 30 mmol) and para-methoxybenzylamine (1.6 g, 13 mmol) at 0° C. The reaction mixture was stirred at room temperature for 4 hrs, and rotary-evaporated to remove the solvent. To the residue was added 300 mL water. The resulting mixture was filtered by suction. The filter cake was washed with ethyl acetate and petroleum ether (volume ratio 1/10, 100 mL) and dried to obtain a pale yellow solid of N-(4-methoxybenzyl)-6-chloro-4-(3-(trifluoromethyl)phenylamino)-1,5-naphthyridine-3-carboxamide (4.5 g).

4) Preparation of 9-chloro-3-(4-methoxybenzyl)-1-(3-(trifluoromethyl)phenyl)pyrimido[5,4-c][1,5]naphthyridine-2,4(1H,3H)-dione

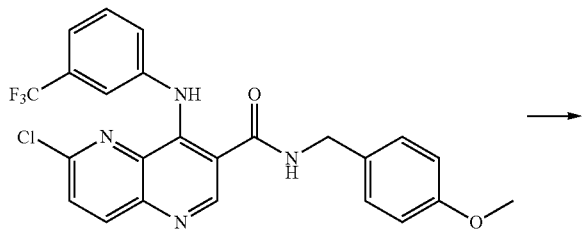

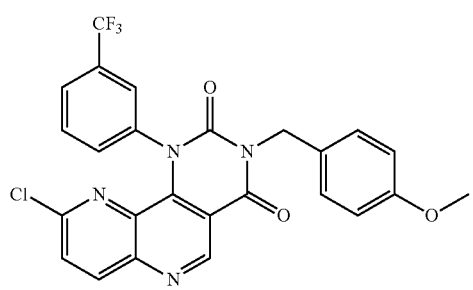

N-(4-methoxybenzyl)-6-chloro-4-(3-(trifluoromethyl)phenylamino)-1,5-naphthyridine-3-carboxamide (4.5 g, 9.2 mmol) is suspended in ethyl chloroformate (50 mL). The resulting mixture was added to 90° C., stirred for 120 hrs, rotary-evaporated to remove the volatile substance, and separated by silicagel column chromatography (EtOAc/PE=0-1/4) to obtain a yellow oil of 9-chloro-3-(4-methoxybenzyl)-1-(3-(trifluoromethyl)phenyl)pyrimido[5,4-c][1,5]naphthyridine-2,4(1H,3H)-dione (700 mg).

5) Preparation of 9-chloro-1-(3-(trifluoromethyl)phenyl)pyrimidino [5,4-c][1,5]naphthyridine-2,4(1H,3H)-dione

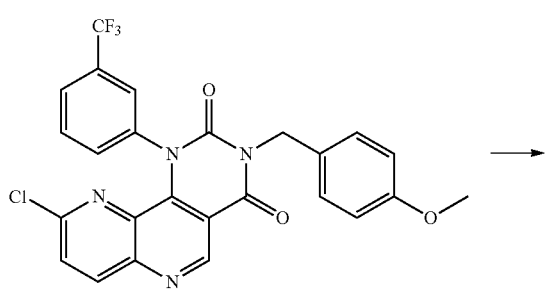

-continued

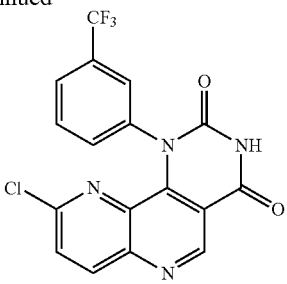

9-chloro-3-(4-methoxybenzyl)-1-(3-(trifluoromethyl) phenyl)pyrimidino[5,4-c][1,5]naphthyridine-2,4(1H,3H)-dione (700 mg, 1.36 mmol) was dissolved in acetonitrile (40 mL) and water (10 mL). Ammonium ceric nitrate (2.9 g, 5.65 mmol) was added in batch at room temperature. The reaction mixture was stirred at room temperature for 18 hrs, and then rotary-evaporated to remove the solvent. The resulting crude product was separated by silicagel column chromatography (EtOAc/PE=0-1/4) to obtain a yellow solid (400 mg).

6) 9-(6-aminopyridin-3-yl)-1-(3-(trifluoromethyl) phenyl)pyrimidino[5,4-c][1,5]naphthyridine-2,4(1H, 3H)-dione

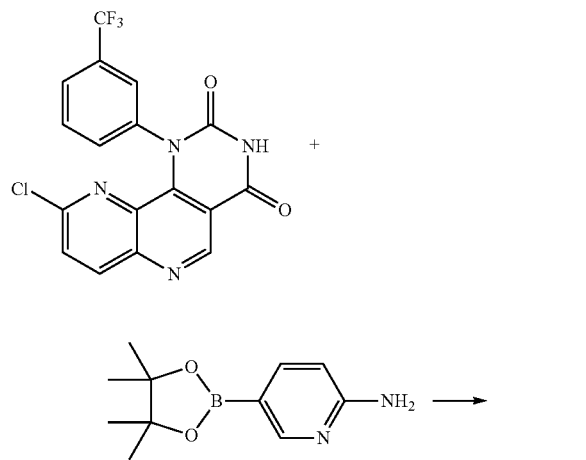

9-chloro-1-(3-(trifluoromethyl)phenyl)pyrimidino[5,4-c] [1,5]naphthyridine-2,4(1H,3H)-dione (400 mg, 1 mmol), 5-(4,4,5,5-tetramethyl-1,3,2-dioxaborolan-2-yl)pyridin-2-amine (440 mg, 2.0 mmol), potassium carbonate (414 mg, 3.0 mmol) and tetrakis(triphenylphosphine)palladium(58 mg, 0.05 mmol) were added to 40 mL dioxane and 2 mL water. The resulting mixture was reacted under reflux in the nitrogen protection for 18 hrs, cooled to room temperature, filtered with Celite, concentrated, and separated by silicagel column chromatography (EtOAc/PE=0-10/1) to obtain a crude product, which was washed with methanol to obtain a yellow solid of 9-(6-aminopyridin-3-yl)-1-(3-(trifluoromethyl)phenyl) pyrimidino[5,4-c][1,5]naphthyridine-2,4(1H,3H)-dione (56 mg).

Formula: $C_{22}H_{13}F_3N_6O_2$ LC-MS (m/e): 451.1 (M+H)
$^1$H-NMR (400 MHz, DMSO-$d_6$) δ: 12.28 (br. s., 1H), 9.26 (s, 1H), 8.33 (m, 1H), 8.21-8.26 (m, 1H), 8.16 (m, 1H), 7.93 (s, 1H), 7.81 (br. s., 1H), 7.70 (m, 2H), 6.76 (m, 1H), 6.46 (s, 2H), 6.24 (m, 1H).

Example 2

Preparation of 9-(6-methoxypyridin-3-yl)-1-(3-(trifluoromethyl)phenyl)pyrimido[5,4-c][1,5]naphthyridine-2,4(1H,3H)-dione (Compound 2)

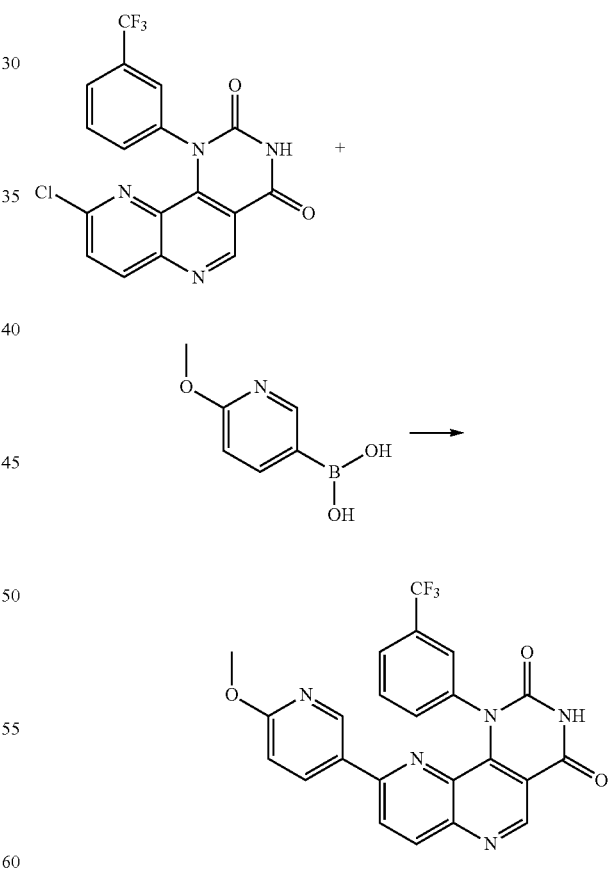

9-chloro-1-(3-(trifluoromethyl)phenyl)pyrimidino[5,4-c] [1,5]naphthyridine-2,4(1H,3H)-dione (300 mg, 0.77 mmol), (6-methoxypyridin-3-yl)boric acid (118 mg, 0.77 mmol), potassium carbonate (317 mg, 2.3 mmol) and tetrakis(triphenylphosphine)palladium(58 mg, 0.05 mmol) were added to 40 mL dioxane and 2 mL water. The resulting mixture was reacted under reflux in the nitrogen protection for 18 hrs, cooled to room temperature, and filtered with Celite. To the resulting filtrate was added sodium chloride, and a solid was separated out and filtered by suction to obtain a crude product, which was washed successively with water, ethyl acetate and methanol to produce 9-(6-methoxypyridin-3-yl)-1-(3-(trifluoromethoxy)phenyl)pyrimidino[5,4-c][1,5]naphthyridine-2,4(1H,3H)-dione (150 mg).

Formula: $C_{23}H_{14}F_3N_5O_3$ LC-MS (m/e): 466.1 (M+H)
$^1$H-NMR (400 Mz, DMSO-d$_6$) δ: 12.32 (br. s., 1H), 9.33 (s, 1H), 8.45 (d, J=9.2, 1H), 8.35 (m, 2H), 7.89 (m, 2H), 7.74 (m, 2H), 7.05 (m, 1H), 6.65 (m, 1H), 3.89 (s, 3H).

Example 3

Preparation of 9-(2-methoxypyrimidin-5-yl)-1-(3-(trifluoromethyl)phenyl)pyrimido[5,4-c][1,5]naphthyridine-2,4(1H,3H)-dione (Compound 17)

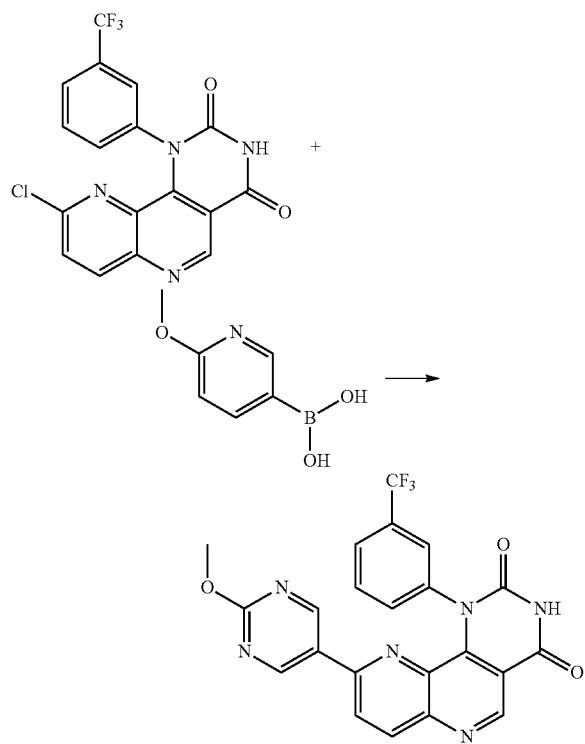

9-chloro-1-(3-(trifluoromethyl)phenyl)pyrimidino[5,4-c][1,5]naphthyridine-2,4(1H,3H)-dione (300 mg, 0.77 mmol), (2-methoxypyrimidin-5-yl)boric acid (119 mg, 0.77 mmol), potassium carbonate (317 mg, 2.3 mmol) and tetrakis(triphenylphosphine)palladium(45 mg, 0.04 mmol) were added to 40 mL dioxane and 2 mL water. The resulting mixture was reacted under reflux in the nitrogen protection for 18 hrs, cooled to room temperature, filtered with Celite, and concentrated. 40 mL water was added. The resulting mixture was filtered to obtain a crude product, which was successively washed with ethyl acetate (30 mL) and methanol (10 mL) to produce 9-(2-methoxypyrimidin-5-yl)-1-(3-(trifluoromethyl)phenyl)pyrimido[5,4-c][1,5]naphthyridine-2,4(1H,3H)-dione (150 mg).

Formula: $C_{22}H_{13}F_3N_6O_3$ LC-MS (m/e): 467.1 (M+H)
$^1$H-NMR (400 MHz, DMSO-d$_6$) δ: 12.35 (br. s., 1H), 9.35 (s, 1H), 8.51 (d, J=8.8 1H), 8.37 (d, J=8.8, 1H), 8.31 (s, 2H), 7.90 (s, 1H), 7.70-7.83 (m, 3H), 3.96 (s, 3H).

Example 4

Preparation of 9-(2-aminopyrimidin-5-yl)-1-(3-(trifluoromethyl)phenyl)pyrimido[5,4-c][1,5]naphthyridine-2,4(1H,3H)-dione (Compound 20)

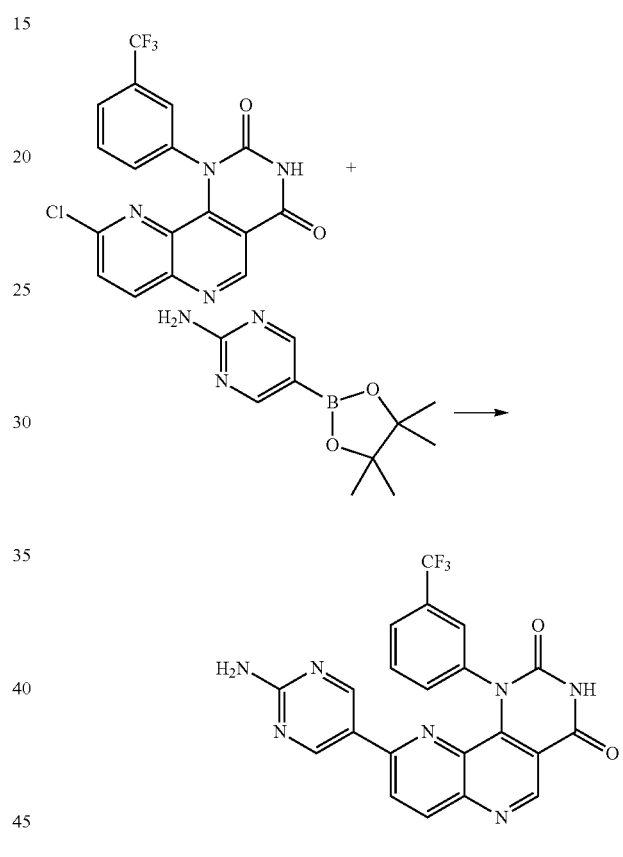

9-chloro-1-(3-(trifluoromethyl)phenyl)pyrimidino[5,4-c][1,5]naphthyridine-2,4(1H,3H)-dione (300 mg, 0.77 mmol), 5-(4,4,5,5-tetramethyl-1,3,2-dioxaborolan-2-yl)pyrimidin-2-amine (170 mg, 0.77 mmol), potassium carbonate (317 mg, 2.3 mmol) and tetrakis(triphenylphosphine)palladium (45 mg, 0.04 mmol) were added to 40 mL dioxane and 2 mL water. The resulting mixture was reacted under reflux in the nitrogen protection for 18 hrs, cooled to room temperature, and concentrated. 400 mL water was added. The resulting mixture was filtered to obtain a crude product, which was dissolved in 20 mL 6M concentrated hydrochloric acid, and washed with dichloromethane (4×50 mL). The aqueous phase was added dropwise to an aqueous sodium carbonate solution, filtered, and washed with water. The resulting crude product was washed with methanol to produce 9-(2-aminopyrimidin-5-yl)-1-(3-(trifluoromethyl)phenyl)pyrimidino[5,4-c][1,5]naphthyridine-2,4(1H,3H)-dione (160 mg).

Formula: $C_{21}H_{12}F_3N_7O_2$ LC-MS (m/e): 452.1 (M+H)

¹H-NMR (400 MHz, DMSO-d6) δ: 12.25 (br. s., 1H), 9.29 (s, 1H), 8.38 (d, 1H), 8.24 (d, J=9.2, 1H), 8.00 (s, 2H), 7.70-7.84 (m, 4H), 7.14 (s, 2H)

Example 5

Preparation of 9-(1H-pyrrolo[2,3-b]pyridin-5-yl)-1-(3-(trifluoromethyl)phenyl)pyrimido[5,4-c][1,5]naphthyridine-2,4(1H,3H)-dione (Compound 30)

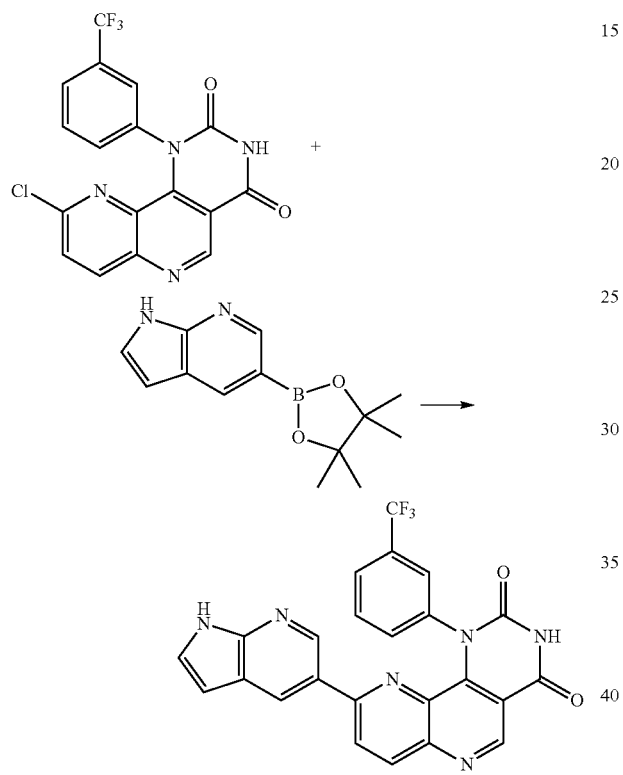

9-chloro-1-(3-(trifluoromethyl)phenyl)pyrimidino[5,4-c][1,5]naphthyridine-2,4(1H,3H)-dione (300 mg, 0.77 mmol), 5-(4,4,5,5-tetramethyl-1,3,2-dioxaborolan-2-yl)-1H-pyrrolo[2,3-b]pyridine (188 mg, 0.77 mmol), potassium carbonate (317 mg, 2.3 mmol) and tetrakis(triphenylphosphine)palladium (45 mg, 0.04 mmol) were added to 40 mL dioxane and 2 mL water. The resulting mixture was reacted under reflux in the nitrogen protection for 18 hrs, cooled to room temperature, and concentrated. 40 mL water was added. The resulting mixture was filtered to obtain a crude product, which was dissolved in 10 mL 6N hydrochloric acid, and washed with DCM (4×50 mL). The aqueous phase was added dropwise to an aqueous sodium carbonate solution, filtered, and washed with water. The resulting crude product was washed with methanol to produce 9-(1H-pyrrolo[2,3-b]pyridin-5-yl)-1-(3-(trifluoromethyl)phenyl)pyrimidino[5,4-c][1,5]naphthyridine-2,4(1H, 3H)-dione (170 mg).

Formula: $C_{24}H_{13}F_3N_6O_3$ LC-MS (m/e): 475.1 (M+H)

¹H-NMR (400 MHz, DMSO-d₆) δ: 11.84 (br. s., 1H), 9.31 (s, 1H), 8.42 (s, 2H), 8.24 (m, 1H), 7.89 (s, 2H), 7.75 (s, 2H), 7.52 (s, 3H), 6.50 (s, 1H).

Preparation of Compound 30 Hydrochloride

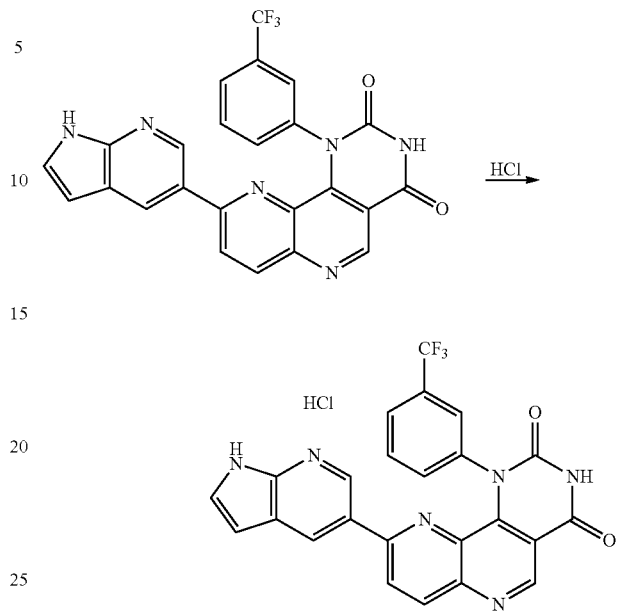

Compound 30 (43 mg, 0.09 mmol) was dispersed in 10 mL methanol. 0.1 mL concentrated hydrochloric acid was added. The resulting mixture was stirred for 1 hour, and concentrated in vacuum to produce the hydrochloride of Compound 30.

Example 6

Preparation of 2-(4-(9-(aminopyridin-3-yl)-2,4-dioxo-3,4-dihydropyrimidino[5,4-c][1,5]naphthyridine-1 (2H)-yl)phenyl)-2-methyl propanenitrile (Compound 41)

1) 2-methyl-2-(4-nitrophenyl)propionitrile

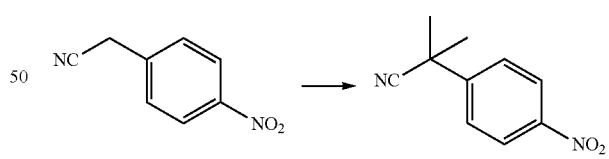

2-(4-nitrophenyl)acetonitrile (4.86 g, 30 mmol) was dissolved in 50 mL dichloromethane. To the resulting mixture was added dropwise 30 mL of an aqueous sodium hydroxide (3.6 g, 90 mmol) solution. Then to the resulting mixture was added dropwise iodomethane (10.65 g, 75 mmol). After the completion of the dropwise addition, the resulting mixture was reacted at room temperature under protection from light for 16 hrs. 50 mL water and 100 mL dichloromethane were added. The phases are separated. The aqueous phase was extracted with 100 mL dichloromethane. The organic phases were combined, dried over anhydrous sodium sulfate, and concentrated. The resulting crude product is separated by silicagel column chromatography (EtOAc/PE=0-1/20) to obtain a pale yellow solid of 2-methyl-2-(4-nitrophenyl) propanenitrile (4.5 g).

2) 2-(4-aminophenyl)-2-methyl propanenitrile

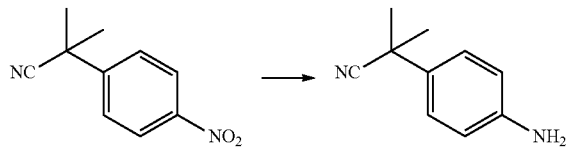

2-methyl-2-(4-nitrophenyl) propanenitrile (4.5 g, 23.6 mmol) was added to a reaction vessel, to which were successively added Pd/C (450 mg) and 50 mL ethyl acetate. The system was vacuumed and hydrogen was introduced. The resulting mixture is reacted at room temperature for 15 hrs. The resulting reaction was filtered with Celite, and washed with ethyl acetate. The resulting filtrate was concentrated to obtain a colorless oil of 2-(4-aminophenyl)-2-methyl propanenitrile (3.5 g).

3) ethyl 6-chloro-4-((4-(2-cyanopropan-2-yl)phenyl) amino)-1,5-naphthyridine-3-carboxylate

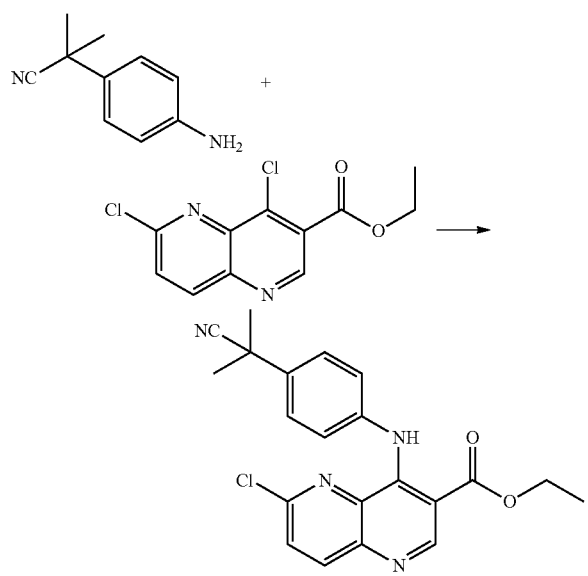

4,6-dichloro-1,5-naphthyridine-3-carboxylate ethyl (5.9 g, 21.9 mmol) and 2-(4-aminophenyl)-2-methyl propanenitrile (3.5 g, 21.9 mmol) were dissolved in 100 mL tert-butanol. To the resulting mixture was added potassium carbonate (6.0 g, 43.8 mmol). The reaction mixture was heated to reflux and reacted for 15 hrs. The reaction was cooled to room temperature, and then concentrated in a reduced pressure. To the residue was added 100 mL water and 100 mL DCM. The phases were separated. The aqueous phase was extracted with 100 mL DCM. The organic phases were combined, dried over anhydrous sodium sulfate, and concentrated. The resulting crude product is separated by silicagel column chromatography (EtOAc/PE=0-1/2) to obtain a pale yellow solid of 6-chloro-4-((4-(2-cyanopropan-2-yl)phenyl)amino)-1,5-naphthyridine-3-carboxylate ethyl (6.9 g).

4) Preparation of 6-chloro-4-((4-(2-cyanopropan-2-yl)phenyl)amino)-N-(4-methoxybenzyl)-1,5-naphthyridine-3-carboxamide

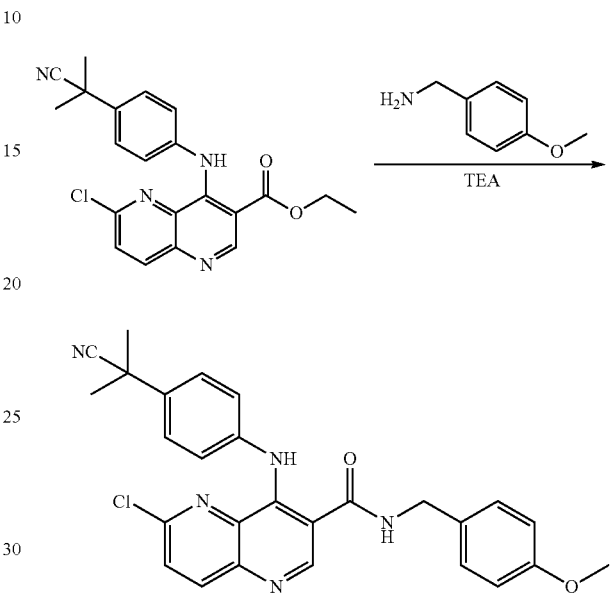

ethyl 6-chloro-4-((4-(2-cyanopropan-2-yl)phenyl)amino)-1,5-naphthyridine-3-carboxylate (6.9 g, 17.5 mmol) was dissolved in 50 mL methanol and 50 mL tetrahydrofuran. To the resulting mixture was added dropwise 50 mL of an aqueous lithium hydroxide (2.2 g, 52.4 mmol) solution at room temperature. After the completion of the dropwise addition, the resulting mixture was reacted at room temperature for 4 hrs. The reaction was concentrated. 200 mL water was added. The resulting mixture was adjusted with hydrochloric acid to pH=2-3. The solid was separated, and dried in vacuum to obtain a yellow solid, which was then dispersed in 100 mL dichloromethane. 0.05 mL DMF was added. To the resulting mixture was added dropwise oxalyl chloride (4.2 g, 33.3 mmol) under an ice bath. After the completion of the dropwise addition, the reaction mixture was warmed up to room temperature and reacted for 4 hrs. The reaction was evaporated under a reduced pressure to remove the solvent, then dissolved in 100 mL dichloromethane. To the resulting mixture was added dropwise a mixture of triethylamine (5.0 g, 49.8 mmol) and para-methoxybenzylamine (2.7 g, 19.9 mmol) under an ice bath. After the completion of the dropwise addition, the reaction mixture was reacted at room temperature for 15 hrs. 50 mL water and 100 mL DCM were added. The phases were separated. The aqueous phase was extracted with 100 mL DCM. The organic phases were combined, dried over anhydrous sodium sulfate, and concentrated. The resulting crude product was separated by silicagel column chromatography (EtOAc/PE=1/10-3/2) to obtain a pale yellow solid (4.0 g).

5) 2-(4-(9-chloro-3-(4-methoxybenzyl)-2,4-dioxo-3,4-dihydropyrimidino[5,4-c][1,5]naphthyridine-1(2H)-yl)phenyl)-2-methylpropanenitrile

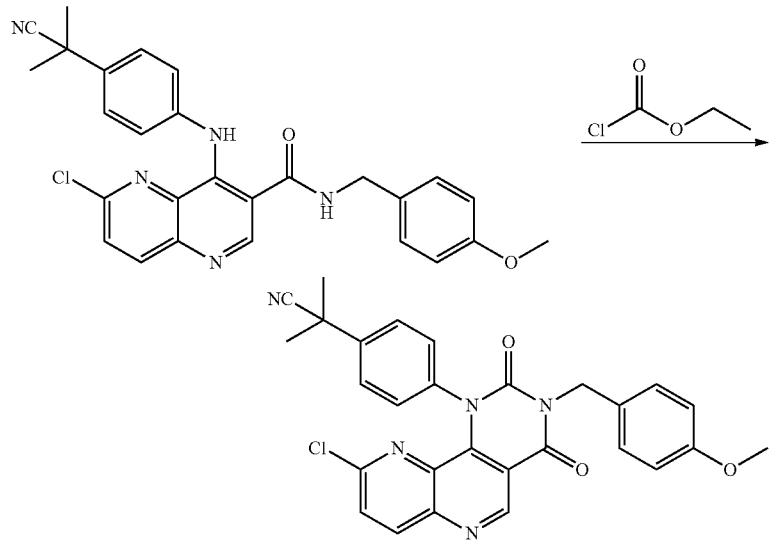

Sodium hydride (1.0 g, 25 mmol) was suspended in 25 mL DMF. To the resulting mixture was slowly added dropwise a solution of 6-chloro-4-((4-(2-cyanoprop-2-yl)phenyl)amino)-N-(4-methoxybenzyl)-1,5-naphthyridine-3-carboxamide (2.43 g, 5 mmol) in DMF (25 mL) at room temperature. After the completion of the dropwise addition, the resulting mixture was warmed up to 60° C. and reacted for 1 hr. To the reaction mixture was slowly added dropwise ethyl chloroformate (1.36 g, 12.5 mmol) under an ice bath. After the completion of the dropwise addition, the resulting mixture was warmed up to 60° C. and reacted for 16 hrs. The reaction was cooled to room temperature, then slowly poured into water, and extracted with ethyl acetate (3×150 mL). The organic phases were combined, washed with a saturated sodium chloride solution, dried over anhydrous sodium sulfate, and concentrated. The resulting crude product was separated by silicagel column chromatography (EtOAc/PE=0-1/5) to produce a pale yellow solid (1.2 g).

6) 2-(4-(9-chloro-2,4-dioxo-3,4-dihydropyrimidino[5,4-c][1,5]naphthyridine-1(2H)-yl)phenyl)-2-methylpropanenitrile

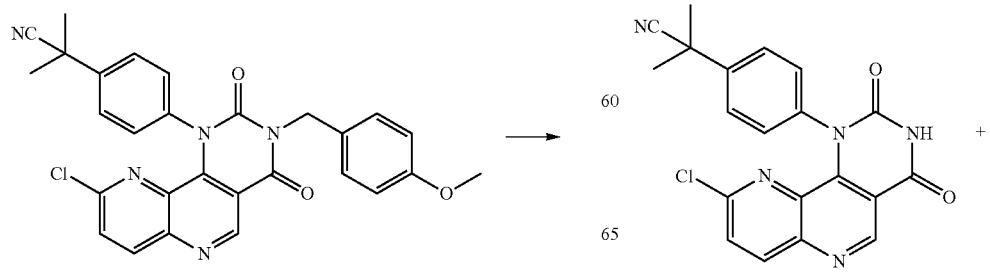

-continued

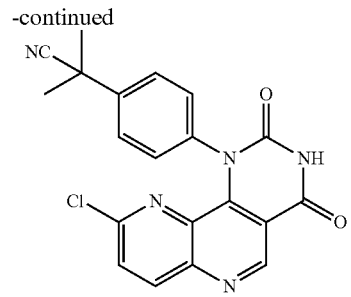

2-(4-(9-chloro-3-(4-methoxybenzyl)-2,4-dioxo-3,4-dihydropyrimidino[5,4-c][1,5]naphthyridine-1(2H)-yl)phenyl)-2-methylpropanenitrile (1.2 g, 2.3 mmol) was dissolved in acetonitrile (80 mL) and water (20 mL). Ammonium ceric nitrate (5.1 g, 9.4 mmol) was added in batch at room temperature. The reaction mixture was reacted at room temperature for 16 hrs, and then concentrated. 100 mL water was added. The mixture was filtered. The resulting solid was washed with EA and PE (1:1), and dried in vacuum to obtain a yellow solid (600 mg).

7) 2-(4-(9-(6-aminopyridin-3-yl)-2,4-dioxo-3,4-dihydropyrimidino[5,4-c][1,5]naphthyridine-1(2H)-yl)phenyl)-2-methylpropanenitrile

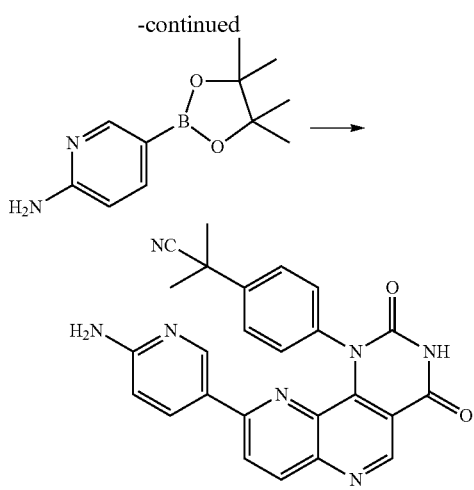

2-(4-(9-chloro-2,4-dioxo-3,4-dihydropyrimidino[5,4-c][1,5]naphthyridine-(2H)-yl)phenyl)-2-methylpropanenitrile (392 mg, 1.0 mmol), 5-(4,4,5,5-tetramethyl-1,3,2-dioxaborolan-2-yl)pyridin-2-amine (440 mg, 1.0 mmol, 50% content) and tetrakis(triphenylphosphine)palladium (46 mg, 0.04 mmol) were dissolved in 40 mL dioxane. To the resulting mixture was added 1 mL of an aqueous potassium carbonate (276 mg, 2 mmol) solution. The reaction mixture was reacted at 100° C. under nitrogen protection for 15-18 hrs, then cooled to room temperature, concentrated, filtered, and washed with water. The resulting crude product was successively washed with ethyl acetate and methanol to produce a pale yellow solid of 2-(4-(9-(6-aminopyridin-3-yl)-2,4-dioxo-3,4-dihydropyrimidino[5,4-c][1,5]naphthyridine-1(2H)-yl)phenyl)-2-methylpropanenitrile (150 mg).

Formula: $C_{25}H_{19}N_7O_2$ LC-MS (m/e): 450.1 (M+H)

$^1$H NMR (400 Mz, DMSO-$d_6$) δ: 12.19 (br. s, 1H), 9.24 (s, 1H), 8.30 (d, J=8.8, 1H), 8.17 (d, J=8.8, 1H), 7.97 (m, 1H), 7.59 (m, 2H), 7.42 (m, 2H), 7.20 (m, 1H), 6.32-6.40 (m, 3H), 1.73 (s, 6H).

Example 7

Preparation of 9-(6-aminopyridin-3-yl)-3-methyl-1-(3-(trifluoromethyl)phenyl)pyrido[5,4-c][1,5]naphthyridine-2,4(1H,3H)-dione (Compound 6)

1) 6-chloro-N-methyl-4-((3-(trifluoromethyl)phenyl)amino)-1,5-naphthyridine-3-carboxamide

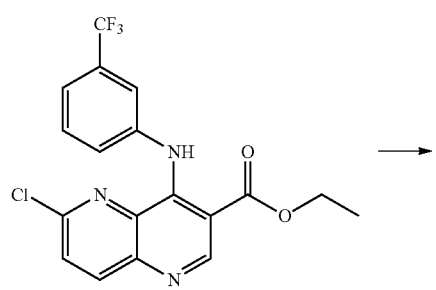

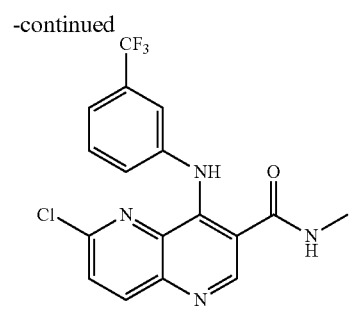

6-chloro-4-((3-(trifluoromethyl)phenyl)amino)-1,5-naphthyridine-3-carboxylate ethyl (3.95 g, 10 mmol) was dissolved in 50 mL methanol and 50 mL tetrahydrofuran. To the resulting mixture was added dropwise 50 mL of an aqueous lithium hydroxide (1.26 g, 30 mmol) solution. After the completion of the dropwise addition, the mixture was stirred at room temperature for 4 hours. The reaction was concentrated. 200 mL water was added. The resulting mixture was adjusted with hydrochloric acid to pH=2-3, filtered by suction, and dried.

The resulting solid and methylamine hydrochloride (924 mg, 13.7 mmol) were placed in 40 mL DMF. To the mixture were added triethylamine (5.99 g, 58.8 mmol), and then HATU (5.6 g, 14.7 mmol). The reaction mixture was stirred at room temperature for 4 hrs. 300 mL water was added. The resulting mixture was filtered by suction. The filter cake was washed with water, and separated by silicagel column chromatography (ethyl acetate/petroleum ether=0-1/1) to produce a pale yellow solid of 6-chloro-N-methyl-4-((3-(trifluoromethyl)phenyl)amino-1,5-naphthyridine-3-carboxamide (2.5 g).

2) 9-chloro-3-methyl-1-(3-(trifluoromethyl)phenyl)pyrimidino[5,4-c][1,5]naphthyridine)-2,4(1H,3H)-dione

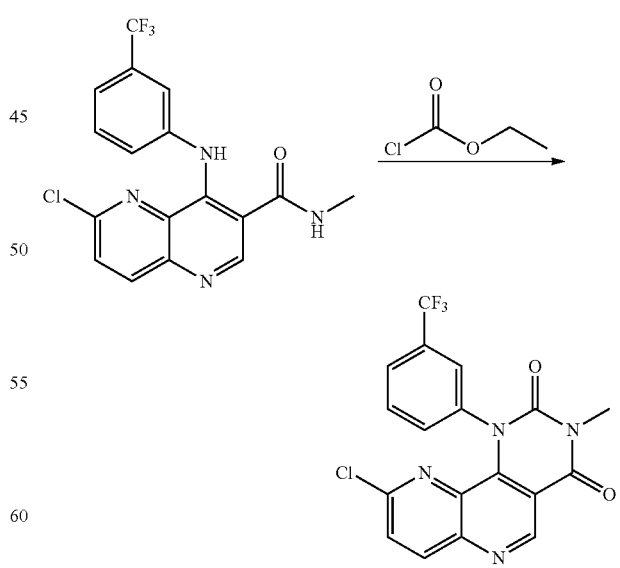

Sodium hydride (1.3 g, 33 mmol) was suspended in 40 mL DMF. At 0° C., to the resulting mixture was slowly added dropwise a solution of 6-chloro-N-methyl-4-((3-(trifluoromethyl)phenyl)amino-1,5-naphthyridine-3-carboxamide (2.5 g, 6.6 mmol) in DMF (60 mL). After the completion of the dropwise addition, the mixture was warmed up to room temperature and stirred for 1 hr. Under an ice bath, ethyl chloroformate (1.8 g, 16.5 mmol) was slowly added dropwise to the reaction. After the completion of the dropwise addition, the reaction mixture was warmed up to 60° C. and stirred for 16 hrs. Then the reaction was cooled to room temperature and water was added. The reaction was extracted with ethyl acetate. The organic phases were combined, washed with a saturated sodium chloride solution, dried over anhydrous sodium sulfate, and separated by silicagel column chromatography (ethyl acetate/petroleum ether=0-1/5) to obtain a yellow oil (1.2 g).

3) 9-(6-aminopyridin-3-yl)-3-methyl-1-(3-(trifluoromethyl)phenyl)pyrido[5,4-c][1,5]naphthyridine-2,4(1H,3H)-dione

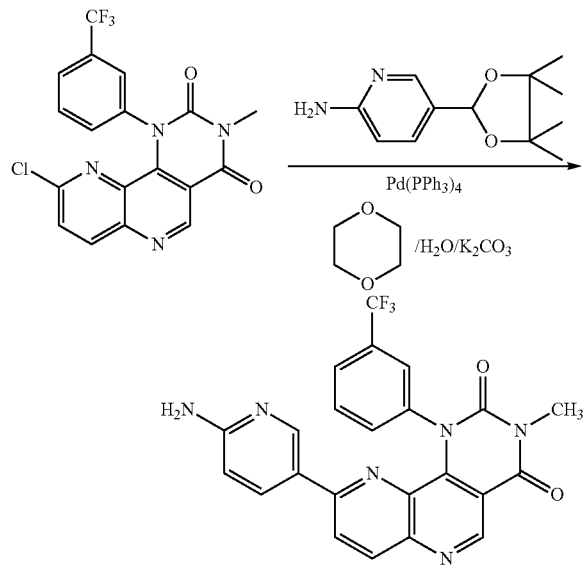

9-chloro-3-methyl-1-(3-(trifluoromethyl)phenyl)-pyrimidino[5,4-c][1,5]naphthyridine-2,4(1H,3H)-dione (609 mg, 1.5 mmol), 5-(4,4,5,5-tetramethyl-1,3,2-dioxaborolan-2-yl)pyridin-2-amine (660 mg, 1.5 mmol, 50% content) and tetrakis(triphenylphosphine)palladium(70 mg, 0.06 mmol) were added to 40 mL dioxane. To the resulting mixture was added 20 mL of an aqueous potassium carbonate (621 mg, 4.5 mmol) solution. The reaction mixture was reacted at 105° C. for 18 hrs under nitrogen protection, then cooled, filtered with Celite, concentrated, and separated by silicagel column chromatography (ethyl acetate/petroleum ether=0-10/1) to produce a crude product, which was dissolved in 50 mL 6M hydrochloric acid. The resulting mixture was washed with dichloromethane. The aqueous phase was added dropwise to an aqueous sodium carbonate solution, filtered by suction, successively washed with water and methanol, and dried to produce 9-(6-aminopyridin-3-yl)-3-methyl-1-(3-(trifluoromethyl)phenyl)pyrido[5,4-c][,5]naphthyridine-2,4(1H,3H)-dione (500 mg).

$^1$H NMR (400 Mz, DMSO-$d_6$) δ: 9.33 (s, 1H), 8.34 (m, 1H), 8.25 (m, 1H), 8.16 (m, 1H), 7.91 (s, 1H), 7.82 (m, 1H), 7.71 (m, 2H), 6.78 (m, 1H), 6.47 (s, 2H), 6.25 (m, 1H), 3.37 (s, 3H)

We claim:
1. A compound of formula (I), or a pharmaceutically acceptable salt or a stereoisomer thereof:

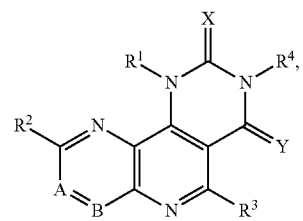

wherein
X and Y are each O;
A and B are each CH;
$R^1$ is 6- to 10-membered aryl, 5- to 6-membered monocyclic heteroaryl, 9- to 10-membered fused heteroaryl, 5- to 6-membered monocyclic heterocyclic group, or 9- to 10-membered fused heterocyclic group, all of which may be optionally substituted with 1-3 $R^{7a}$(s);
$R^2$ is 6- to 10-membered aryl, 5- to 6-membered monocyclic heteroaryl, 9- to 10-membered fused heteroaryl, 5- to 6-membered monocyclic heterocyclic group, or 9- to 10-membered fused heterocyclic group, all of which may be optionally substituted with 1-3 $R^{7b}$(s);
$R^3$ is hydrogen;
$R^4$ is hydrogen or $C_{1-6}$alkyl, wherein $C_{1-6}$alkyl may be optionally substituted with 1-3 substituents selected from halogen, hydroxy and carboxyl;
$R^{7a}$ and $R^{7b}$ are each independently
(1) halogen, cyano, hydroxy, —$(CH_2)_n NR^{8a}R^{8b}$, —$(CH_2)_n C(O)R^9$, —$(CH_2)_n S(O)_m R^9$, —$(CH_2)_n S(O)_m NR^{8a}R^{8b}$, —$(CH_2)_n N(R^{8a})S(O)_m R^9$, —$(CH_2)_n C(O)NR^{8a}R^{8b}$, —$(CH_2)_n OC(O)R^9$, —$(CH_2)_n C(O)(CH_2)_n OR^9$, or —$(CH_2)_n N(R^{8a})C(O)R^9$,
(2) $C_{1-6}$alkyl or $C_{1-6}$alkoxy, both of which may be optionally substituted with 1-3 substituents selected from halogen, hydroxy and cyano, or;
(3) 5- to 10-membered heteroaryl or 5- to 10-membered heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_n NR^{8a}R^{8b}$, —$(CH_2)_n C(O)R^9$, —$(CH_2)_n C(O)NR^{8a}R^{8b}$, —$(CH_2)_n S(O)_m R^9$, —$(CH_2)_n S(O)_m NR^{8a}R^{8b}$, —$(CH_2)_n N(R^{8a})S(O)_m R^9$, —$(CH_2)_n OC(O)R^9$, and —$(CH_2)_n N(R^{8a})C(O)R^9$;
$R^{8a}$ and $R^{8b}$ are each independently hydrogen or $C_{1-6}$alkyl;
$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;
m is 0, 1 or 2; and
n is 0-3.
2. The compound of claim 1, or a pharmaceutically acceptable salt or a stereoisomer thereof:
X and Y are each O;
A and B are each CH;
$R^1$ is 6- to 10-membered aryl or 5- to 6-membered monocyclic heteroaryl, both of which may be optionally substituted with 1-3 $R^{7a}$(s);
$R^2$ is 6- to 10-membered aryl, 5- to 6-membered monocyclic heteroaryl, or 9- to 10-membered fused heteroaryl, all of which may be optionally substituted with 1-3 $R^{7b}$(s);

R³ is hydrogen;
R⁴ is hydrogen or $C_{1-6}$alkyl, wherein $C_{1-6}$alkyl may be optionally substituted with hydroxy;
$R^{7a}$ and $R^{8a}$ are each independently
(1) halogen, cyano, hydroxy, —$(CH_2)_nNR^{8a}R^{8b}$, —$(CH_2)_nC(O)R^9$, —$(CH_2)_nS(O)_mR^9$, —$(CH_2)_nC(O)NR^{8a}R^{8b}$, —$C(O)(CH_2)_nOR^9$, or —$(CH_2)_nN(R^{8a})C(O)R^9$,
(2) $C_{1-6}$alkyl or $C_{1-6}$alkoxy, both of which may be optionally substituted with 1-3 substituents selected from halogen, hydroxy and cyano, or
(3) 5- to 6-membered monocyclic heteroaryl or 5- to 6-membered monocyclic heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_nC(O)R^9$, —$(CH_2)_nC(O)NR^{8a}R^{8b}$, —$(CH_2)_nOC(O)R^9$, and —$(CH_2)_nN(R^{8a})C(O)R^9$;
$R^{8a}$ and $R^{8b}$ are each independently hydrogen or $C_{1-6}$alkyl;
$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;
m is 0, 1 or 2; and
n is 0-3.

3. The compound of claim 1, or a pharmaceutically acceptable salt or a stereoisomer thereof:
X and Y are each O;
A and B are each CH;
R¹ is phenyl, pyridyl, or pyrimidyl, all of which may be optionally substituted with 1-3 $R^{7a}$(s);
R² is phenyl, pyridyl, pyrimidyl, thienyl, pyrazolyl, indazolyl, indolyl, pyridopyrrolyl, pyrazolylpyridyl, or quinolyl, all of which may be optionally substituted with 1-3 $R^{7b}$(s);
R³ is hydrogen;
R⁴ is hydrogen, methyl, ethyl or hydroxymethyl;
$R^{7a}$ and $R^{8a}$ are each independently
(1) cyano, hydroxy, trifluoromethyl, —$NR^{8a}R^{8b}$, —$C(O)R^9$, —$S(O)_mR^9$, —$C(O)NR^{7a}R^{7b}$, —$C(O)(CH_2)_nOR^9$, or —$N(R^{8a})C(O)R^9$,
(2) $C_{1-6}$alkyl or $C_{1-6}$alkoxy, both of which may be optionally substituted with 1-3 substituents selected from halogen, hydroxy and cyano, or
(3) pyrrolyl, pyrazolyl, imidazolyl, piperidyl, piperazinyl, or morpholinyl, all of which may be optionally substituted with 1-3 substituents selected from halogen, hydroxy, cyano, trifluoromethyl, $C_{1-6}$alkyl, $C_{1-6}$alkoxy, —$NR^{8a}R^{8b}$, —$C(O)R^9$, —$C(O)NR^{8a}R^{8b}$, —$OC(O)R^9$, and —$N(R^{8a})C(O)R^9$;
$R^{8a}$ and $R^{8b}$ are each independently hydrogen or $C_{1-6}$alkyl;
$R^9$ is hydrogen or $C_{1-6}$alkyl, wherein $C_{1-6}$alkyl may be optionally substituted with 1-3 substituents selected from halogen, cyano, and hydroxy;
m is 0, 1 or 2.

4. The compound of claim 1, or a pharmaceutically acceptable salt or a stereoisomer thereof:
X and Y are each O;
A and B are each CH;
R¹ is 5- to 6-membered monocyclic heterocyclic group, which may be optionally substituted with 1-3 $R^{7a}$(s);
R² is 6- to 10-membered aryl, 5- to 6-membered monocyclic heteroaryl, or 9- to 10-membered fused heteroaryl, all of which may be optionally substituted with 1-3 $R^{7b}$(s);
R³ is hydrogen;
R⁴ is hydrogen, methyl, or hydroxymethyl;
$R^{7a}$ and $R^{7b}$ are each independently (1) cyano, hydroxy, —$(CH_2)_nNR^{8a}R^{8b}$, —$(CH_2)_nC(O)R^9$, —$(CH_2)_nS(O)_mR^9$, —$(CH_2)_nC(O)NR^{7a}R^{7b}$, —$C(O)(CH_2)_nOR^9$, or —$(CH_2)_nN(R^{8a})C(O)R^9$,
(2) $C_{1-6}$alkyl or $C_{1-6}$alkoxy, both of which may be optionally substituted with 1-3 substituents selected from halogen, hydroxy and cyano, or
(3) 5- to 6-membered monocyclic heteroaryl or 5- to 6-membered monocyclic heterocyclic group, both of which may be optionally substituted with 1-3 substituents selected from halogen, hydroxy, cyano, trifluoromethyl, $C_{1-6}$alkyl, $C_{1-6}$alkoxy, —$(CH_2)_nNR^{8a}R^{8b}$, —$(CH_2)_mC(O)R^9$, —$(CH_2)_nC(O)NR^{8a}R^{8b}$, —$(CH_2)_nOC(O)R^9$, and —$(CH_2)_nN(R^{8a})C(O)R^9$;
$R^{8a}$ and $R^{8b}$ are each independently hydrogen or $C_{1-6}$alkyl;
$R^9$ is hydrogen or $C_{1-6}$alkyl, wherein $C_{1-6}$alkyl may be optionally substituted with 1-3 substituents selected from halogen, cyano, hydroxy, and —$NR^{8a}R^{8b}$;
m is 0, 1 or 2; and
n is 0-3.

5. A compound selected from the group consisting of the following compounds, or a pharmaceutically acceptable salt or a stereoisomer thereof:

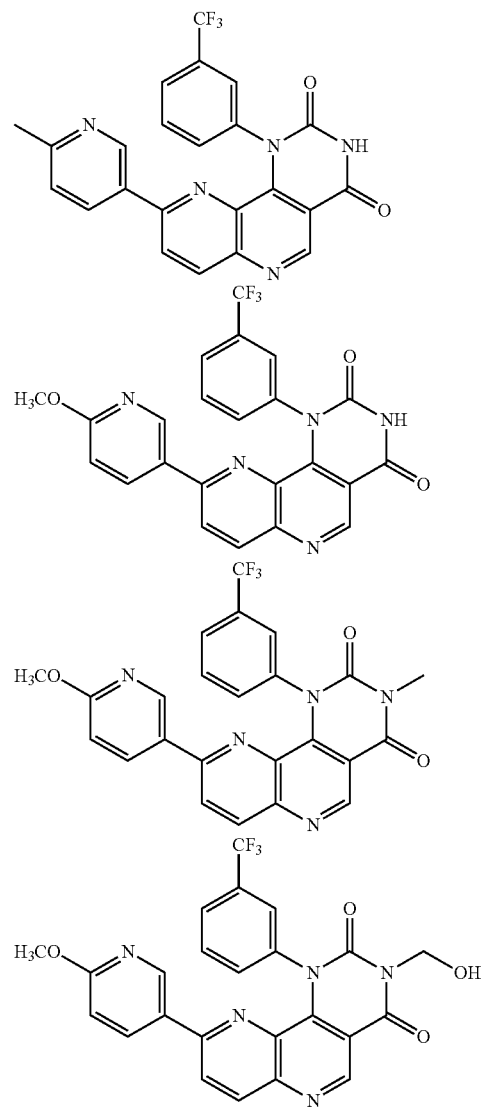

113
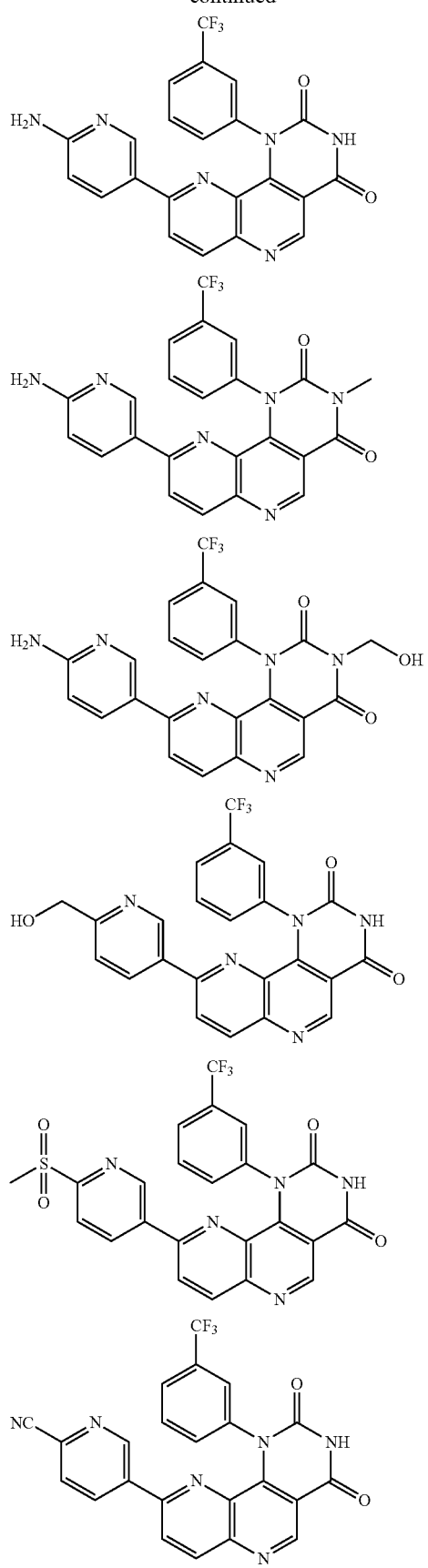
114
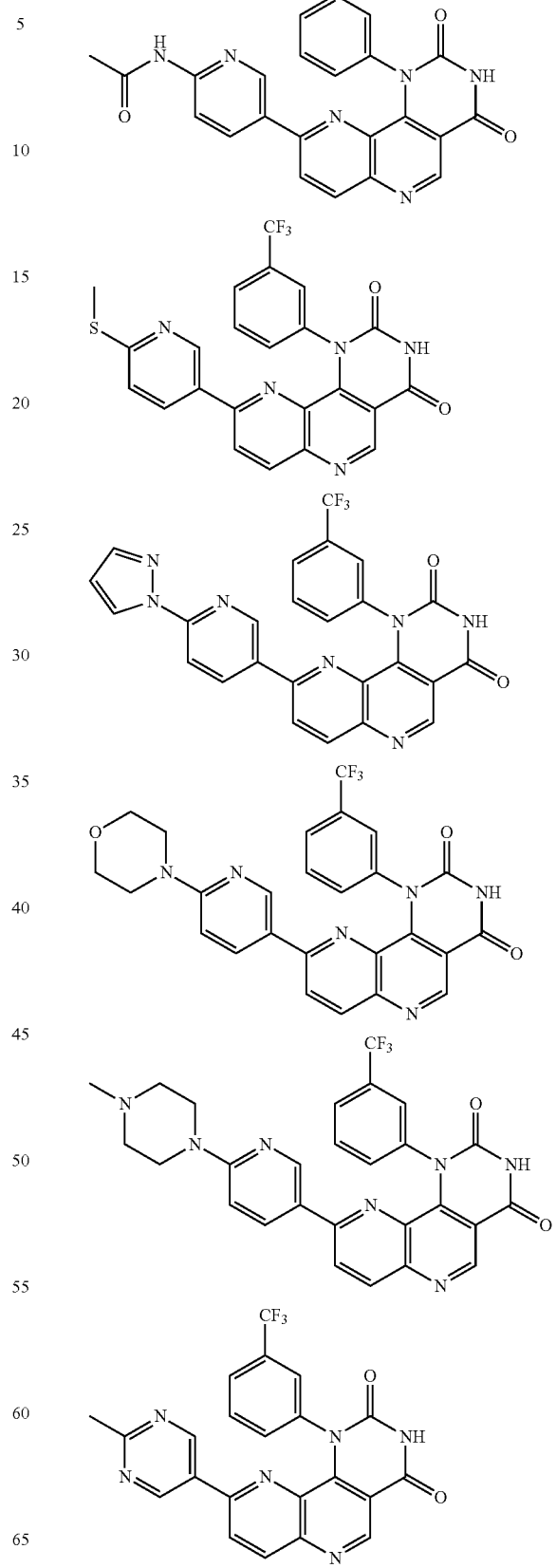

115
-continued
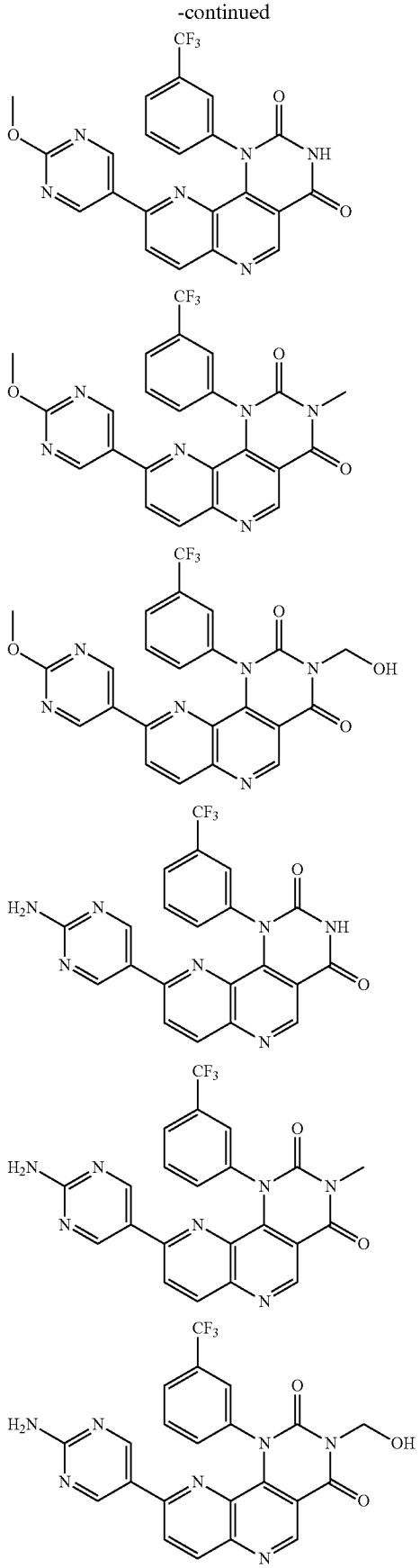
116
-continued
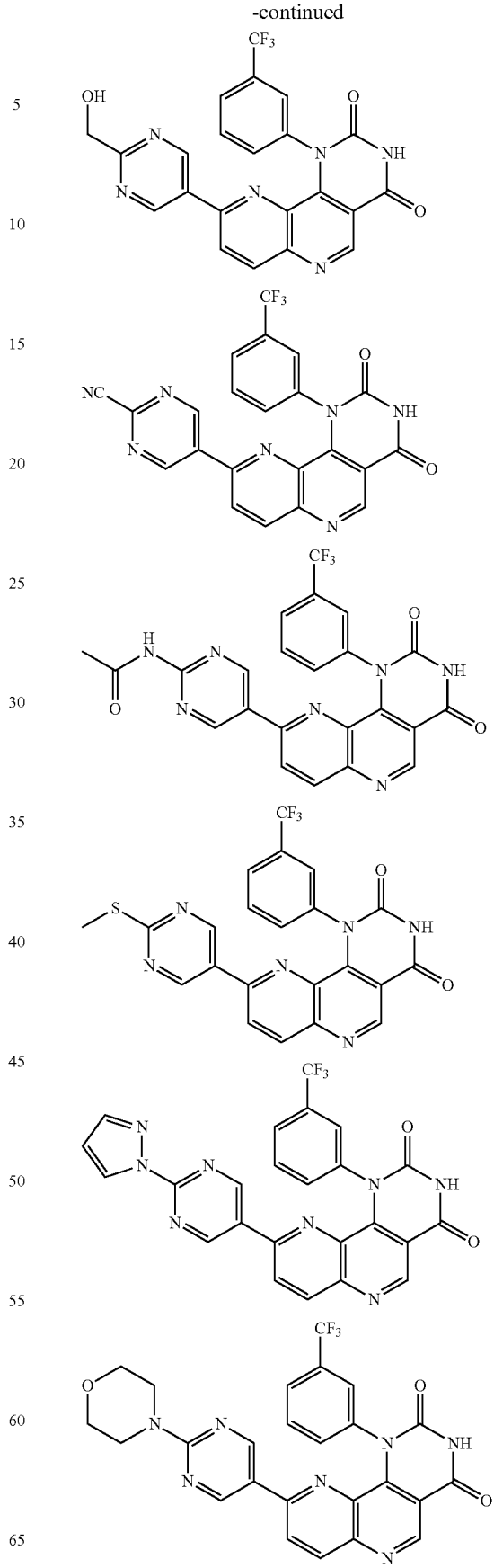

117
-continued
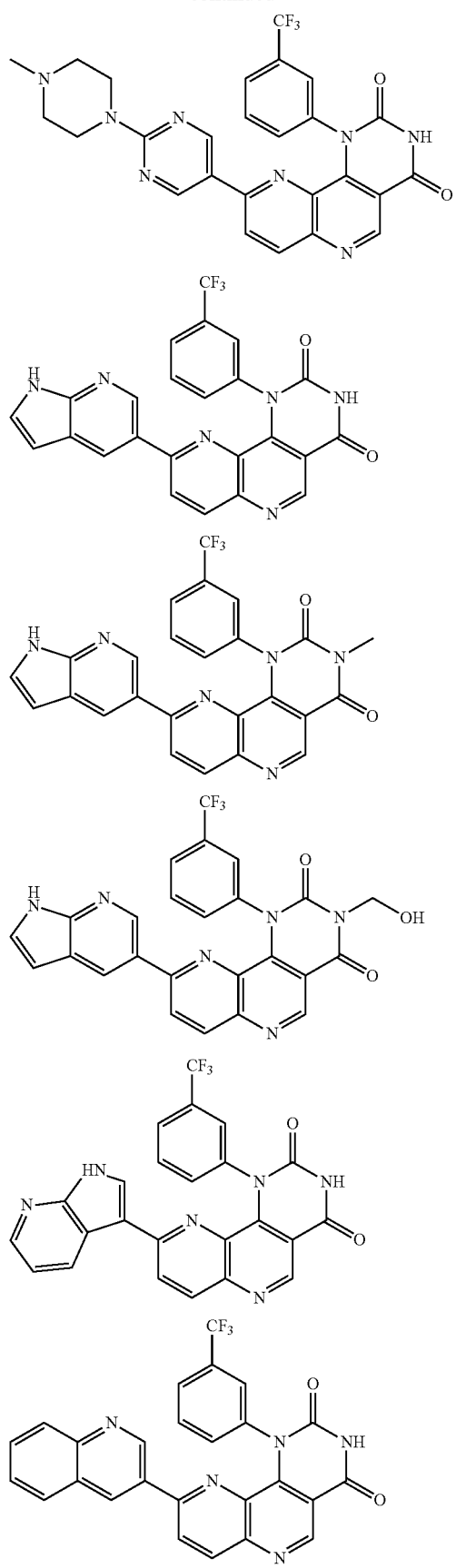
118
-continued
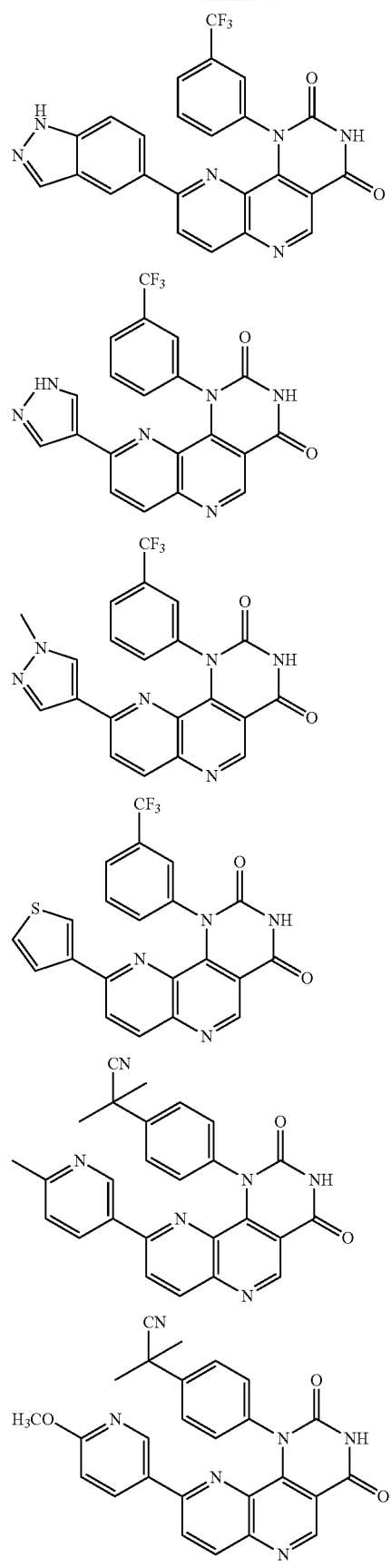

119
-continued
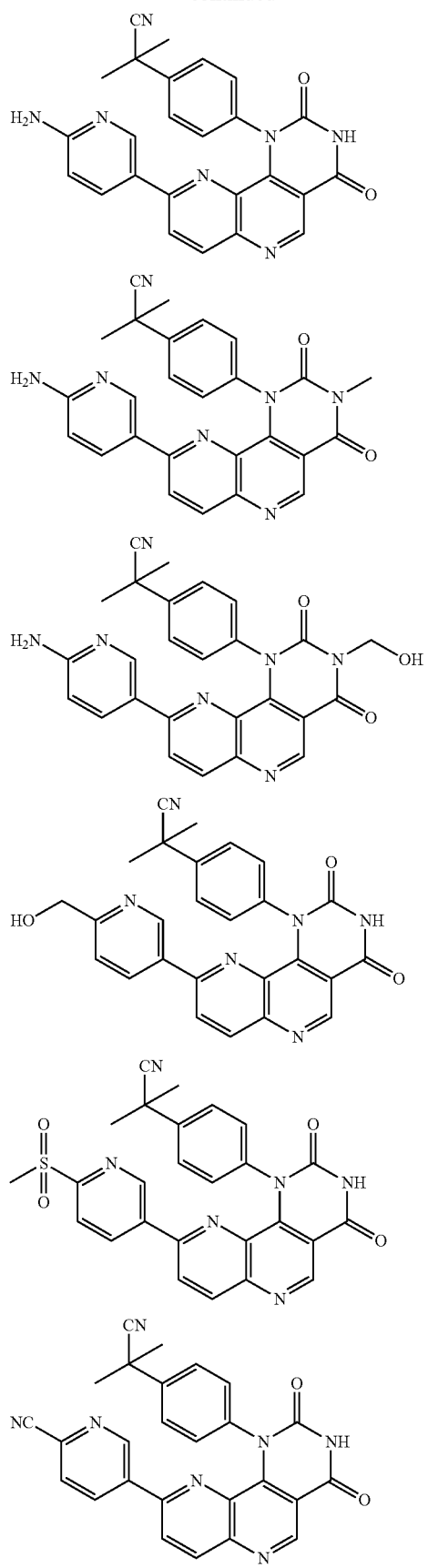
120
-continued
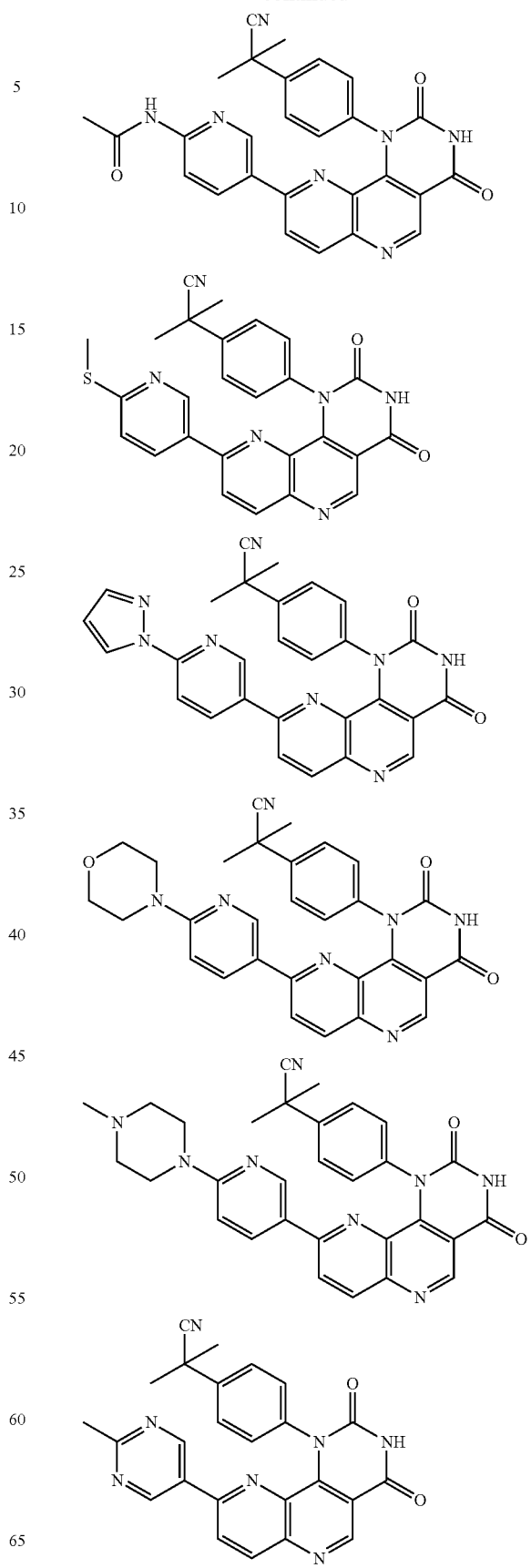

-continued
| 121 | 122 |
|---|---|
| 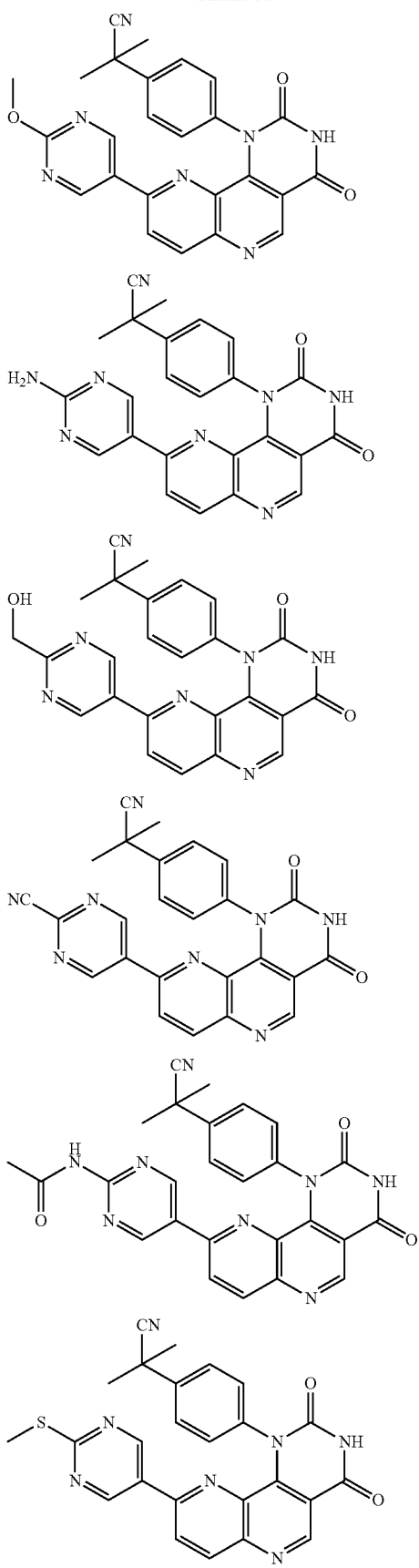 | 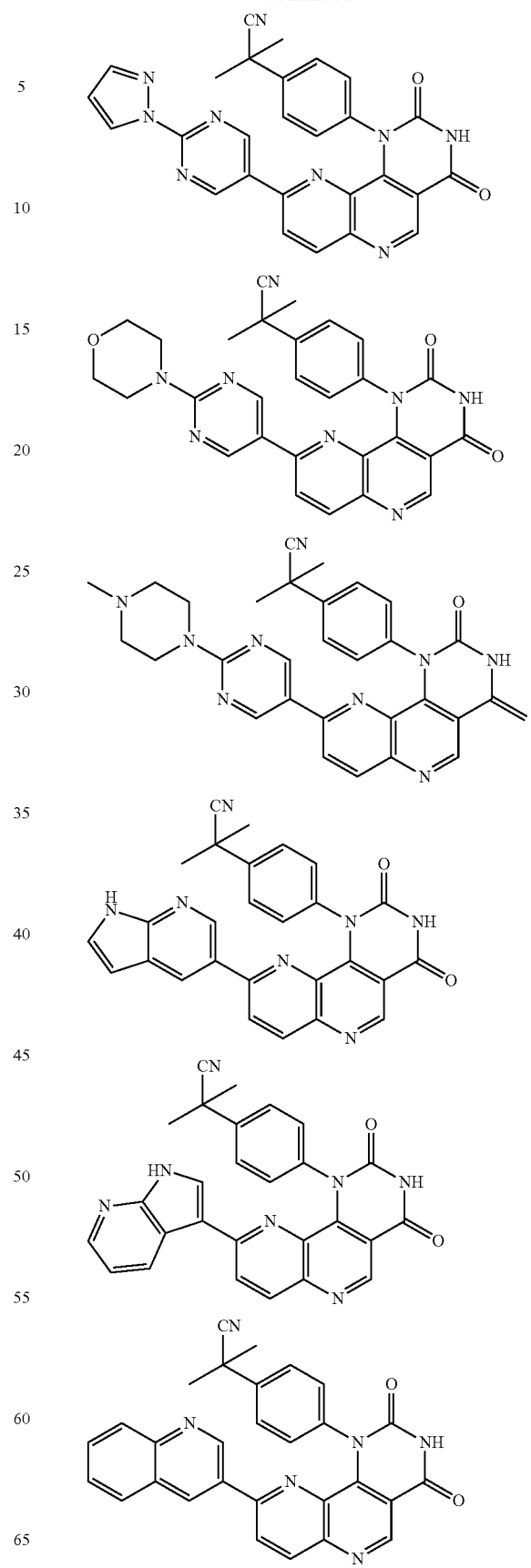 |

123
-continued
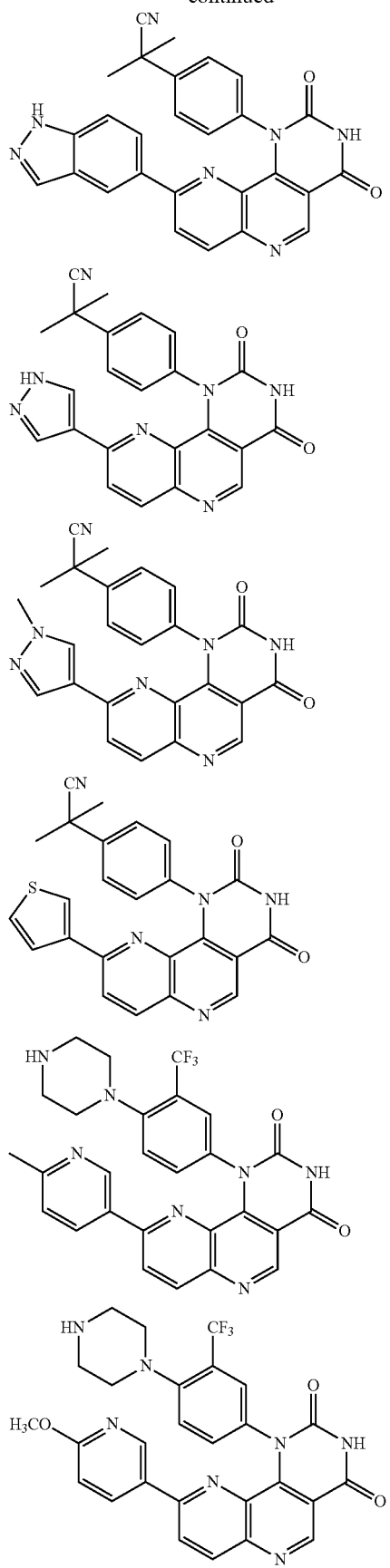
124
-continued
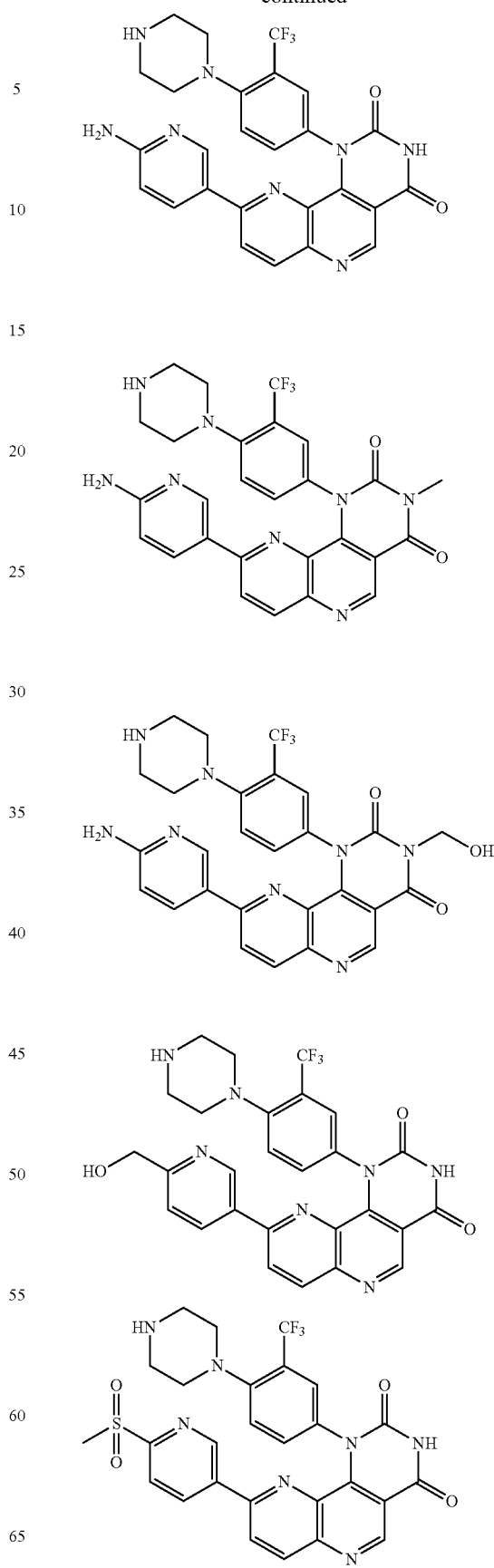

125
-continued
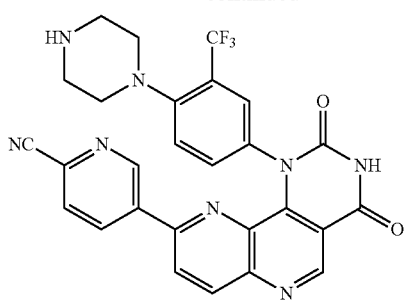
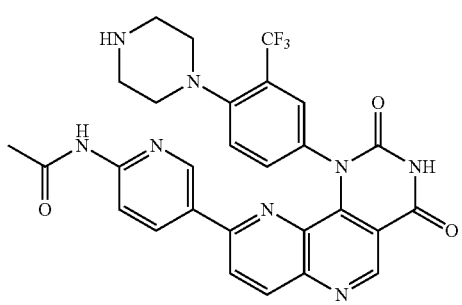
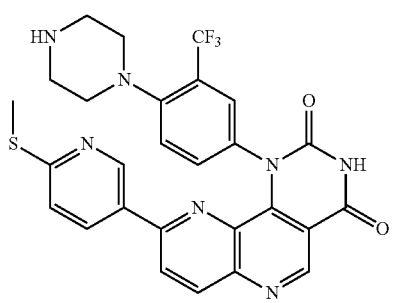
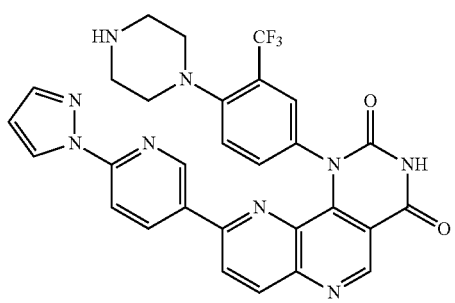
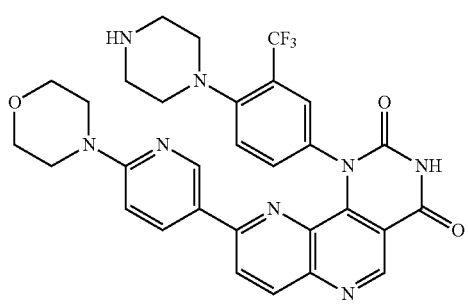
126
-continued
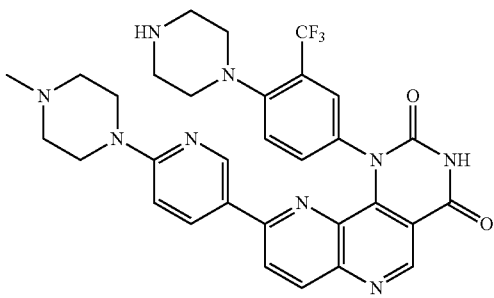
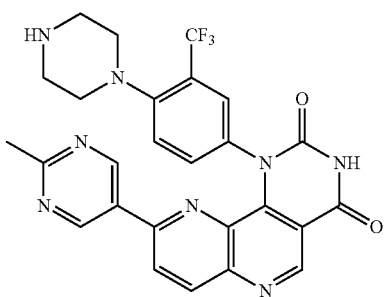
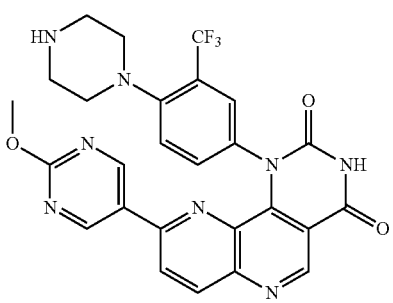
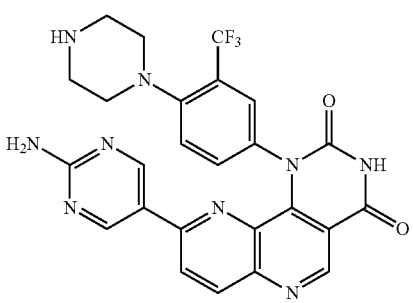

127
-continued
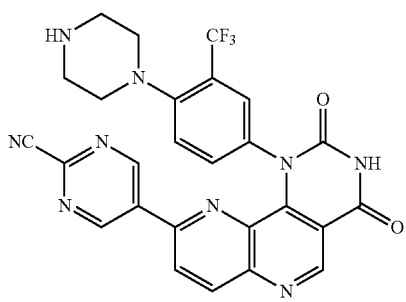
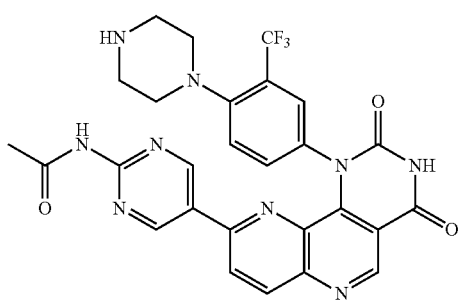
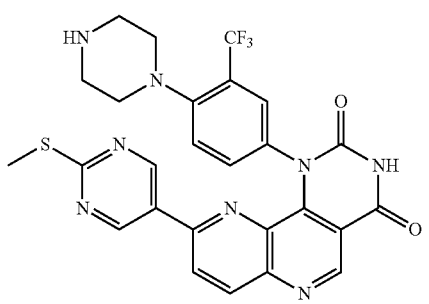
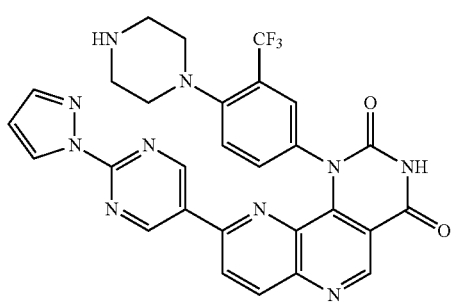
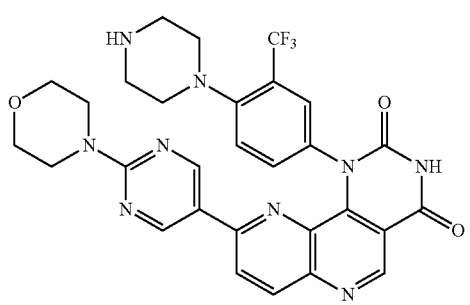
128
-continued
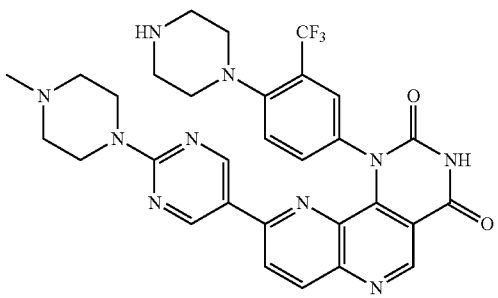
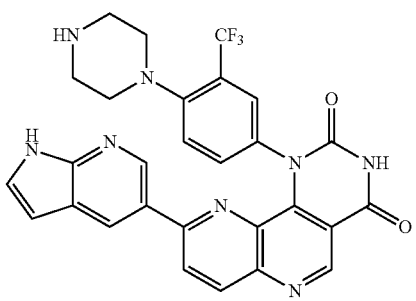
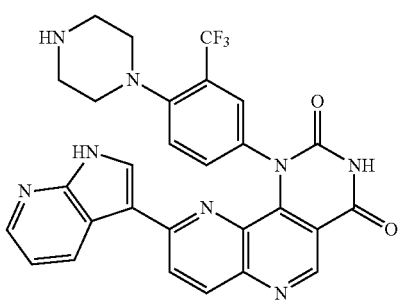
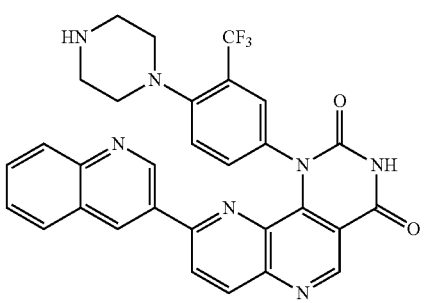
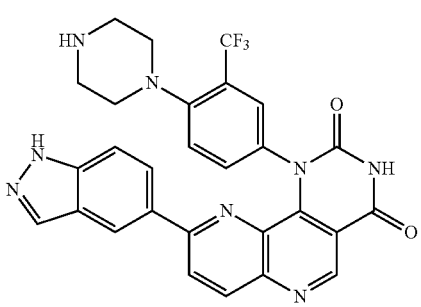

129
-continued
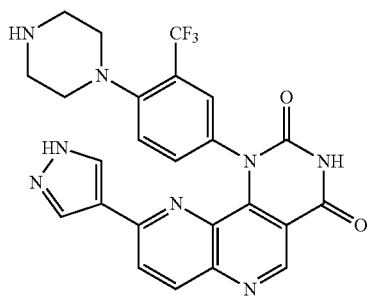
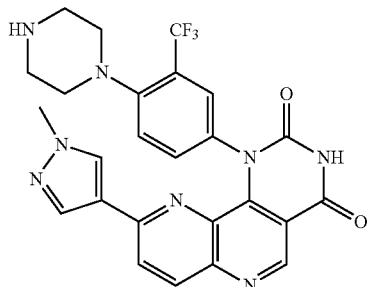
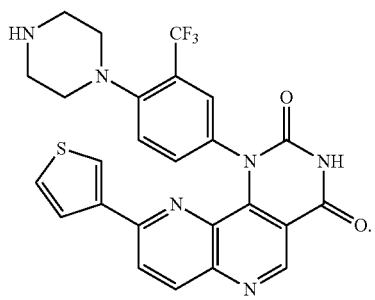
6. A compound selected from the group consisting of the following compounds, or a pharmaceutically acceptable salt or a stereoisomer thereof:
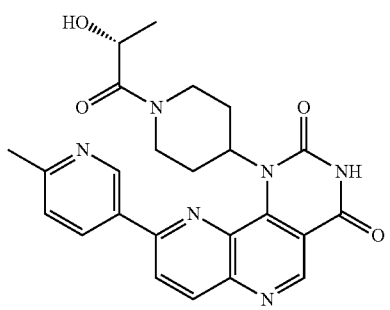
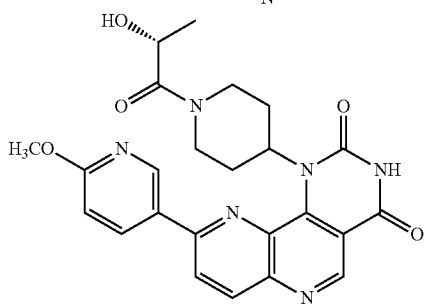
130
-continued
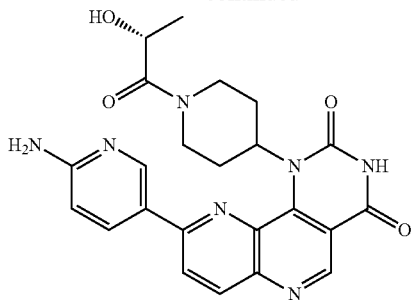
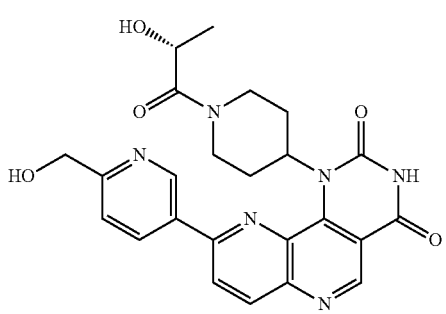
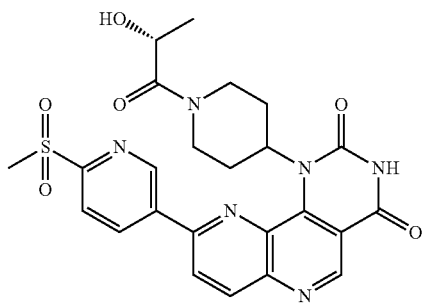
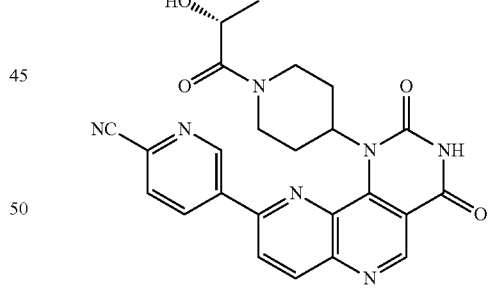
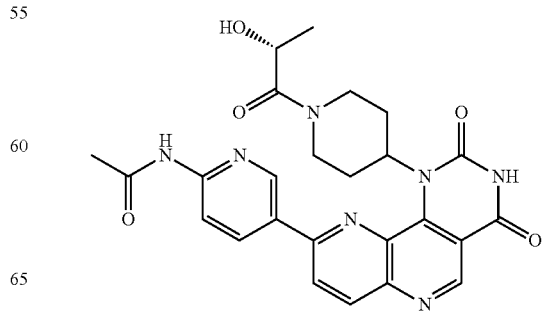

| 131 | 132 |
|---|---|
| -continued | -continued |
| 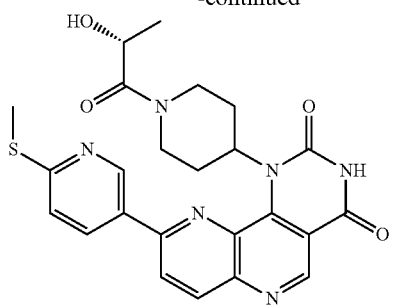 | 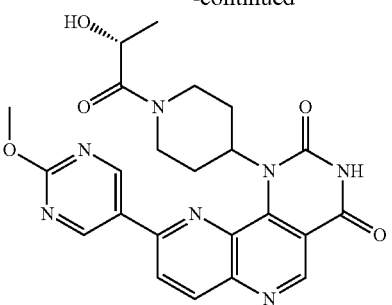 |
| 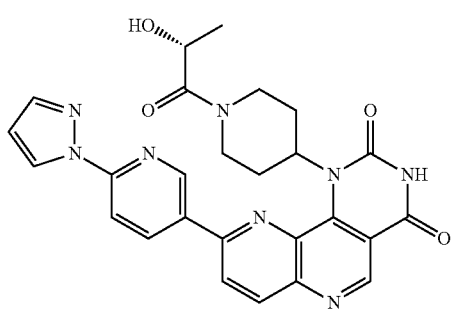 | 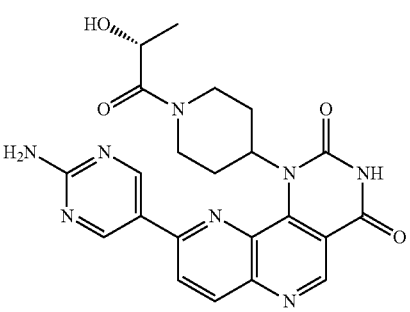 |
| 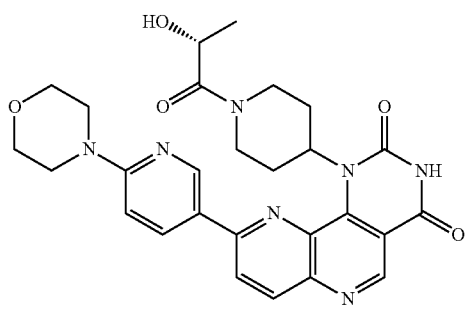 | 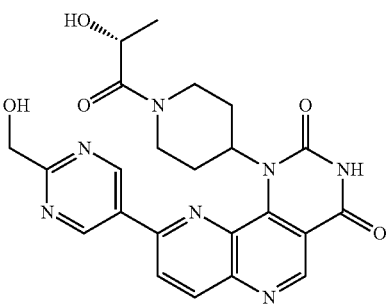 |
| 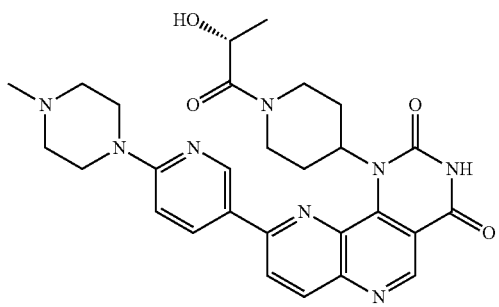 | 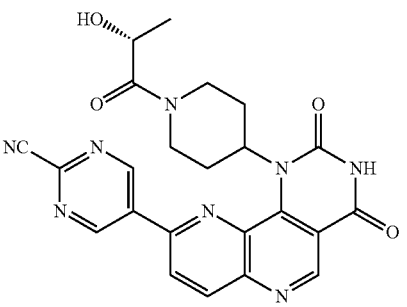 |
| 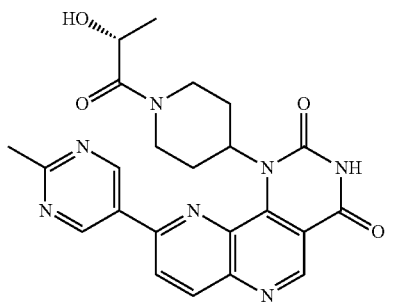 | 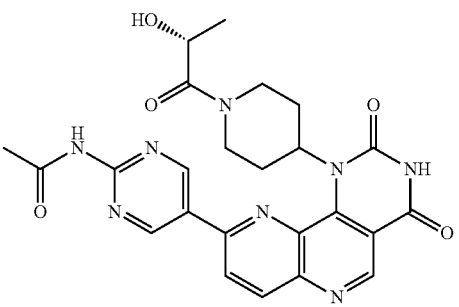 |

133
-continued
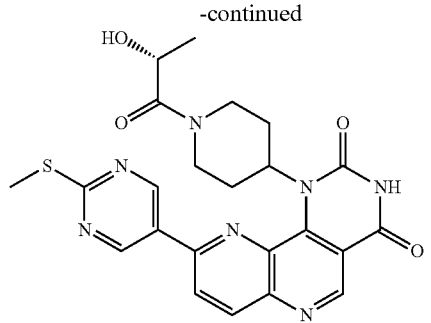
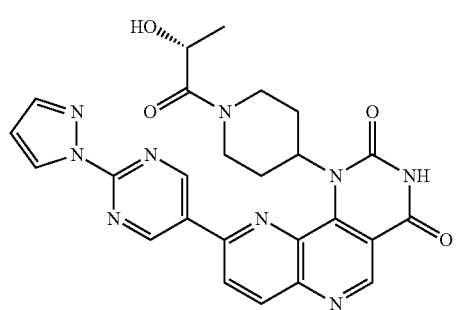
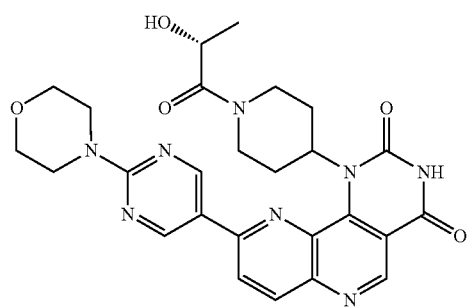
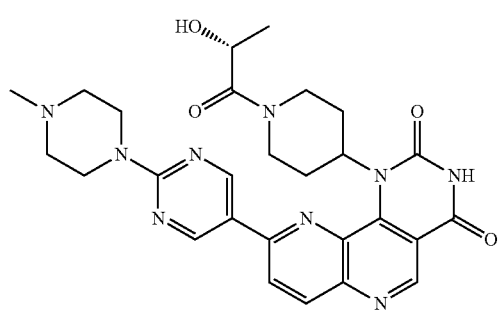
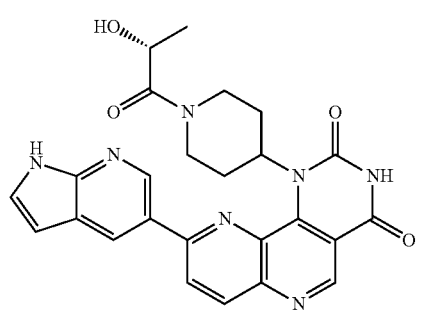
134
-continued
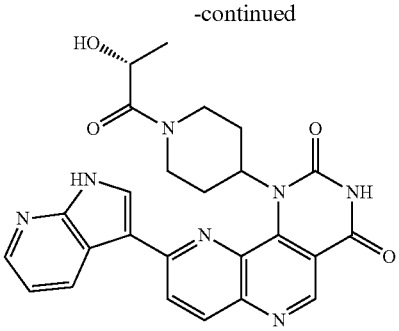
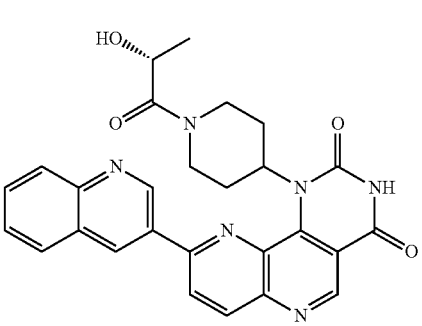
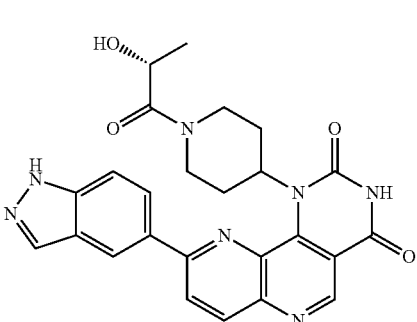
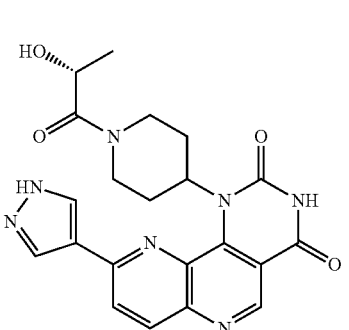
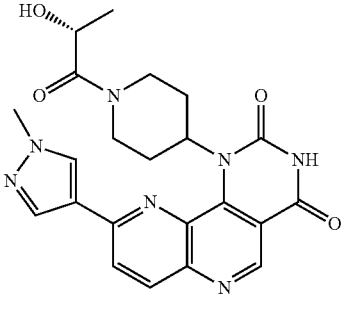

135
-continued
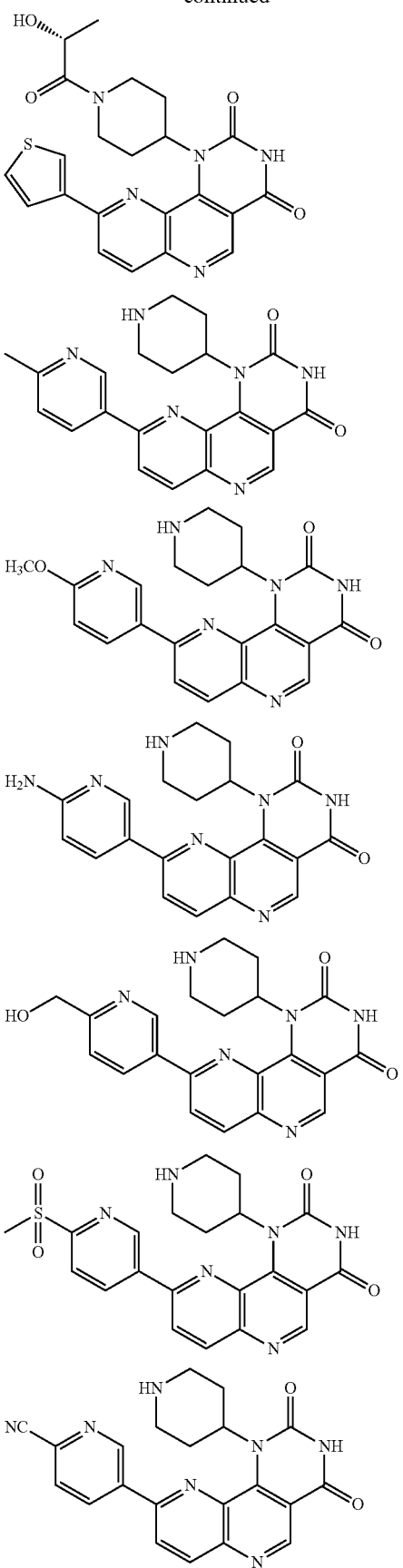
136
-continued
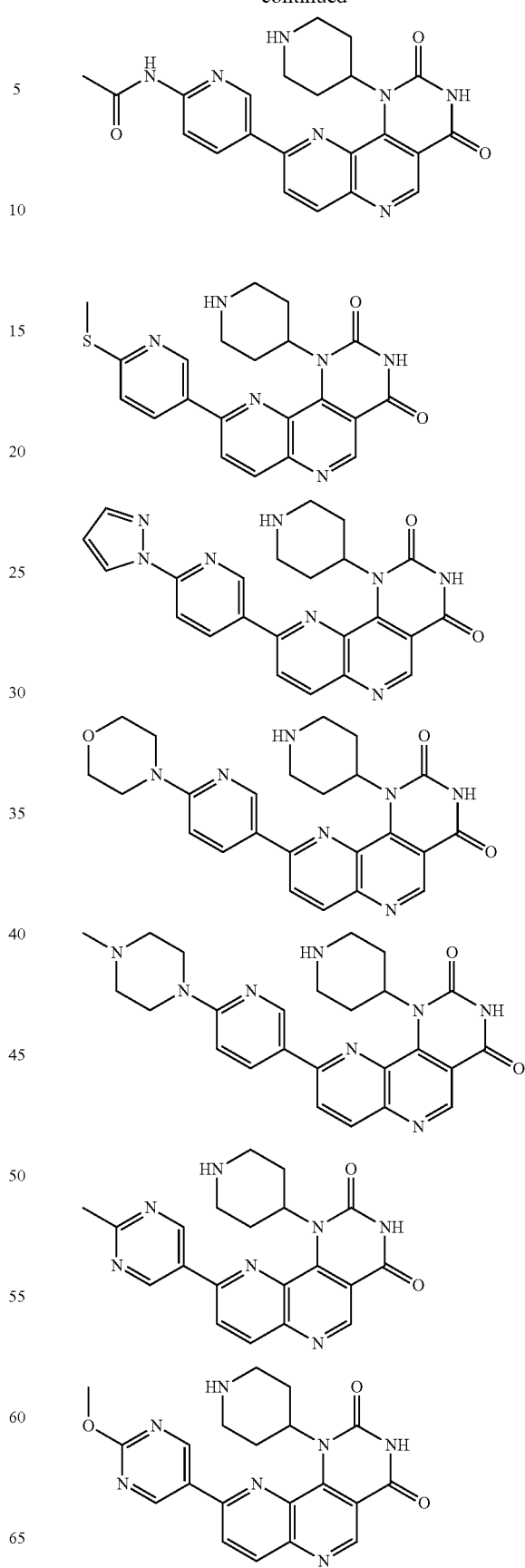

137
-continued
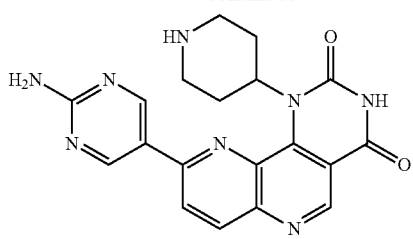
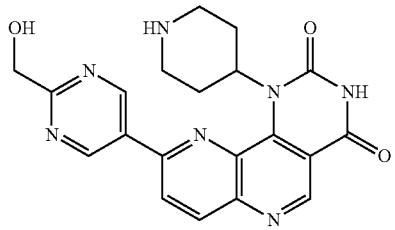
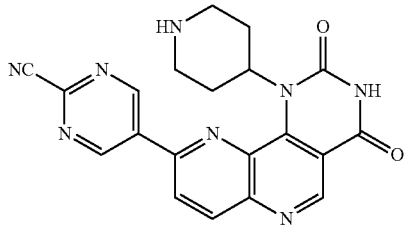
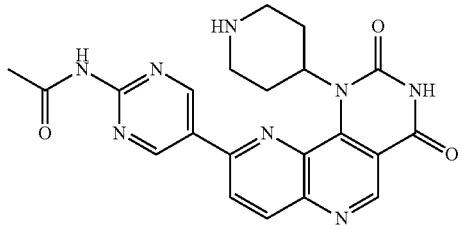
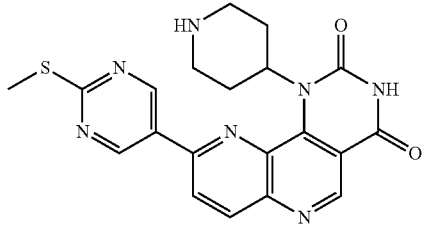
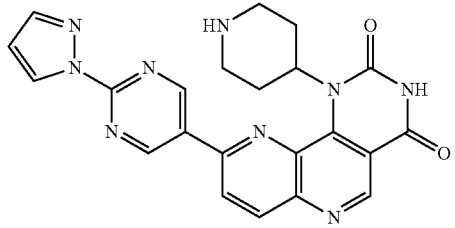
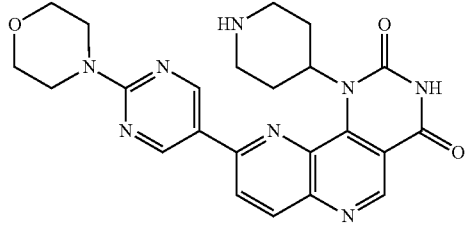
138
-continued
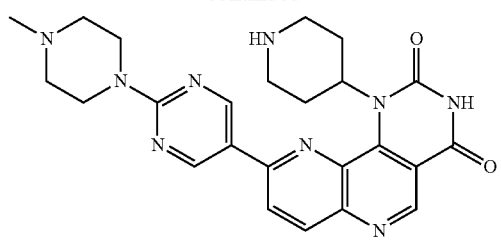
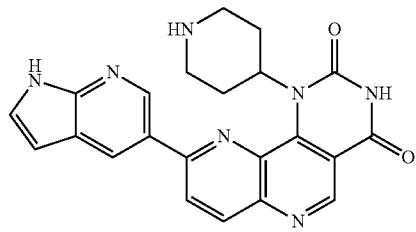
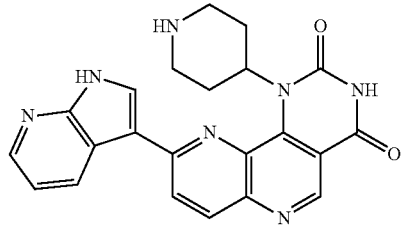
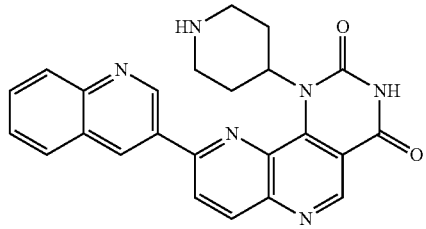
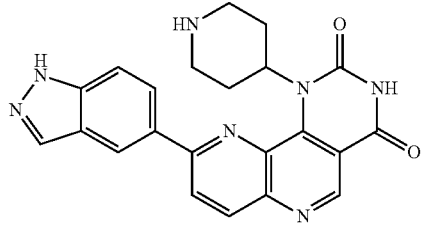
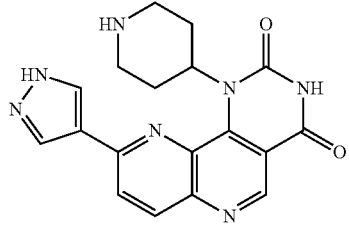
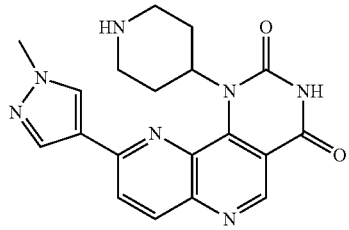

139
-continued
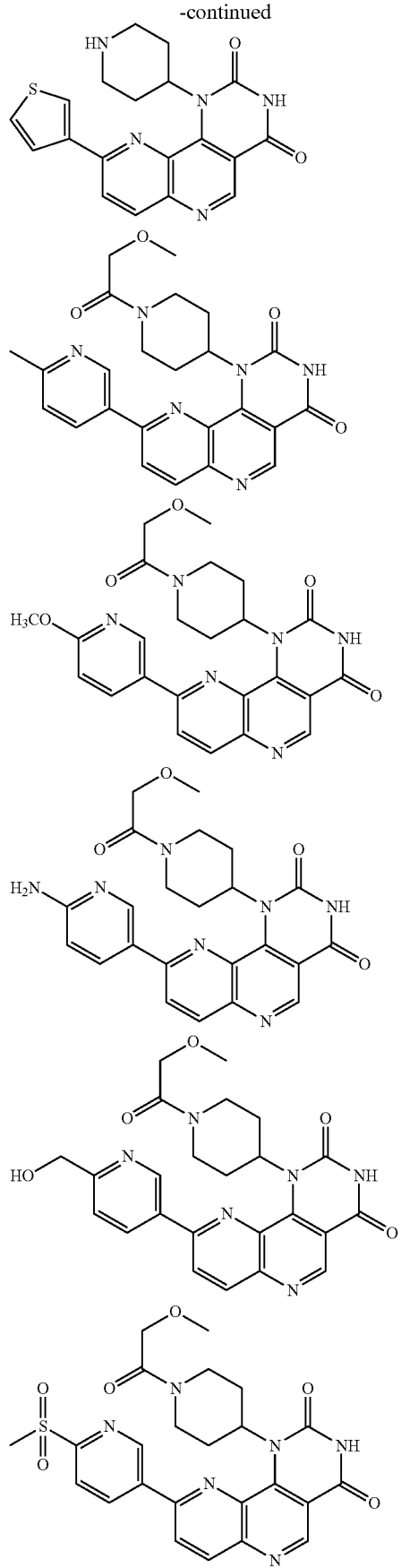
140
-continued
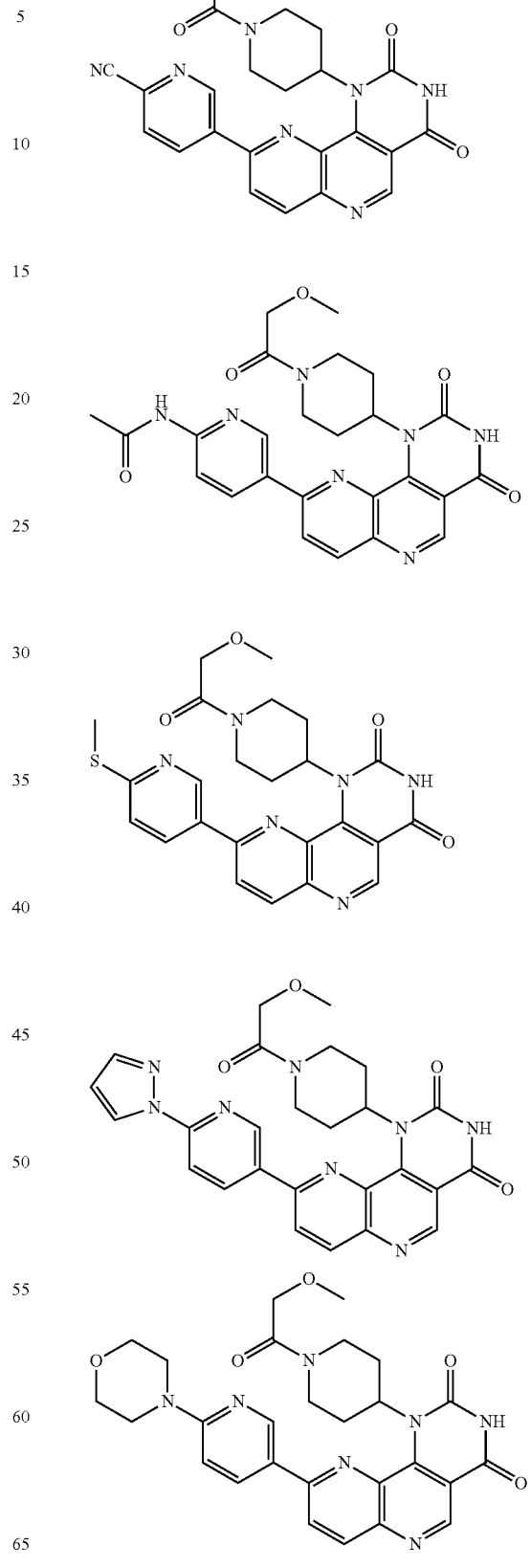

141
-continued
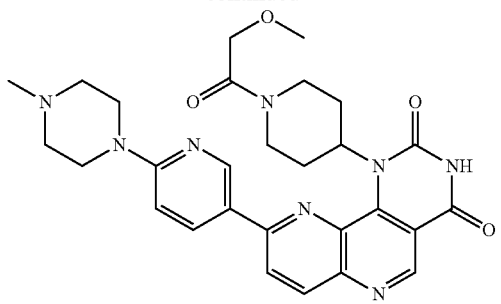
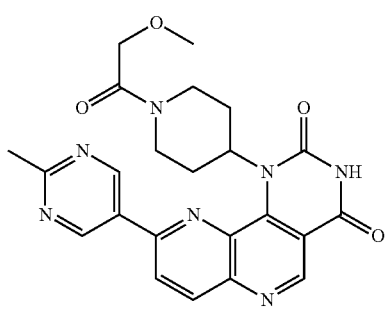
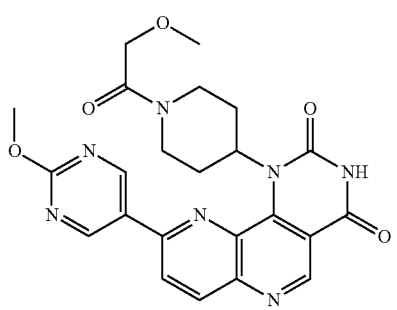
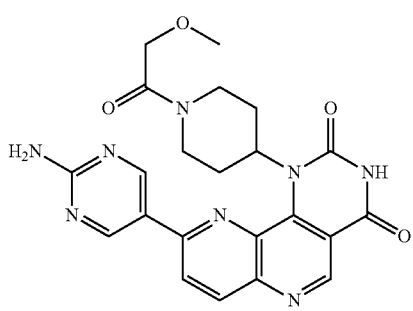
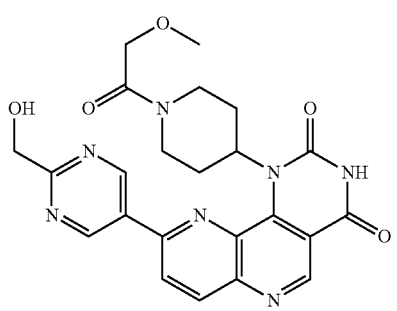
142
-continued
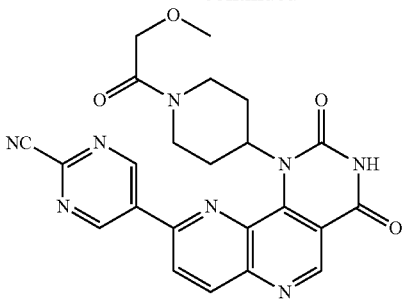
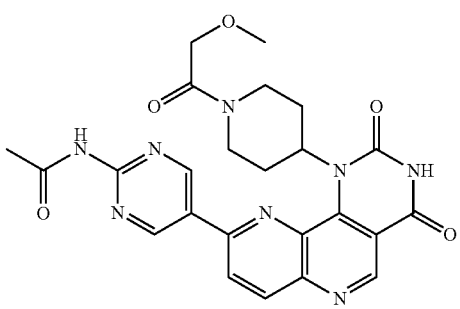
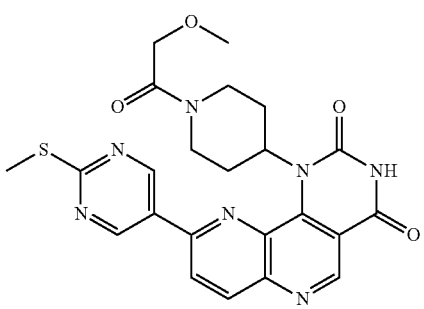
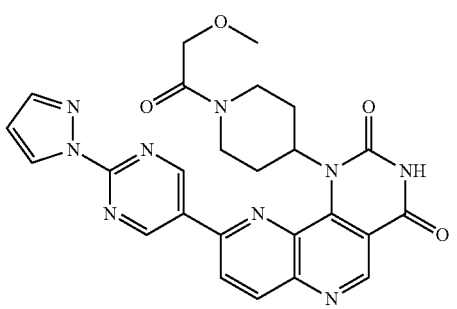
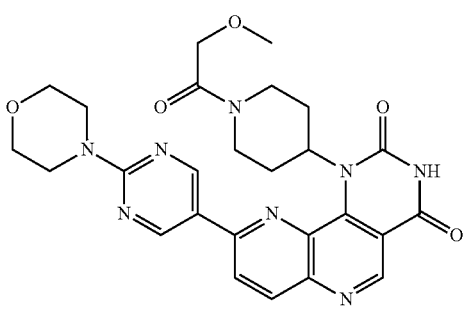

143
-continued
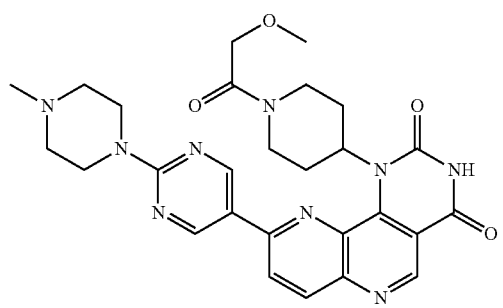
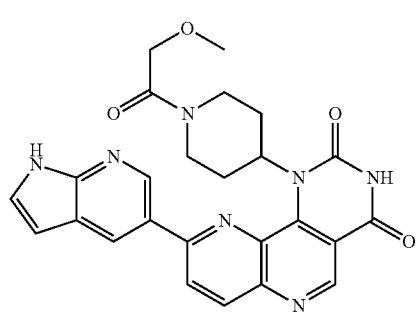
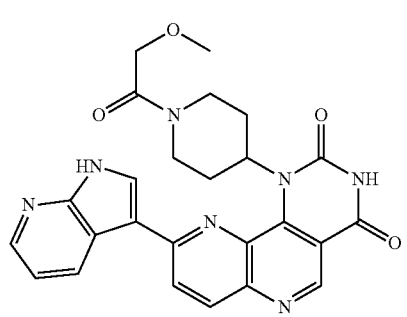
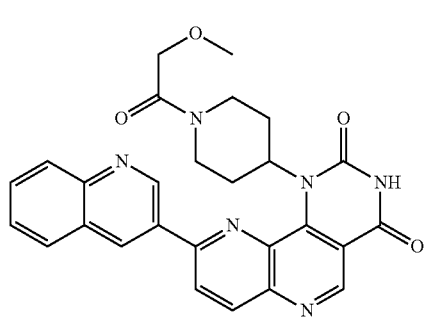
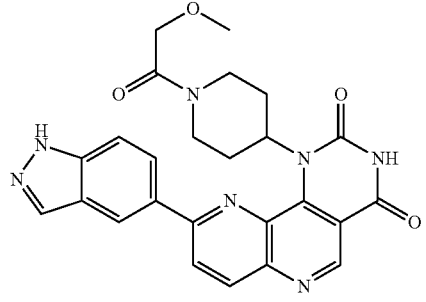
144
-continued
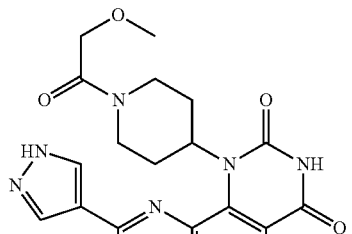
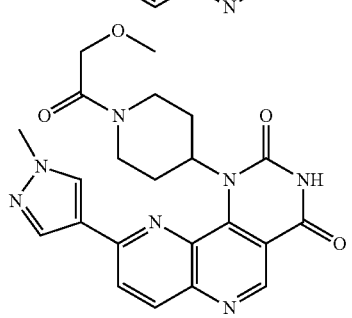
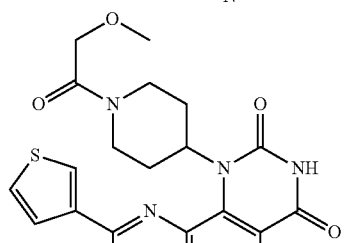
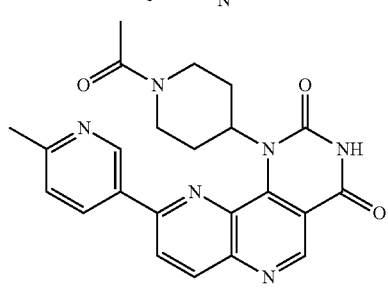
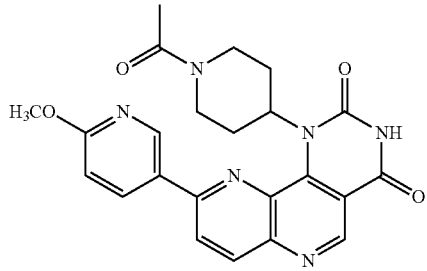
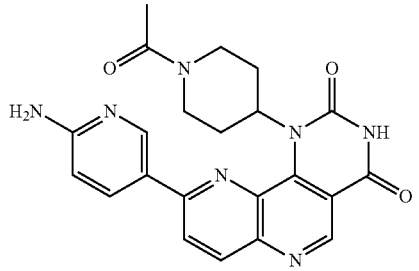

145
-continued
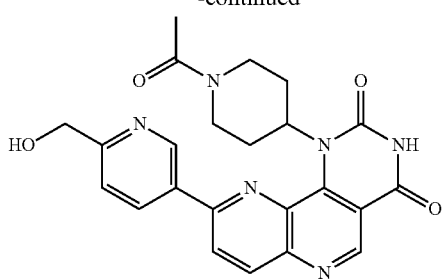
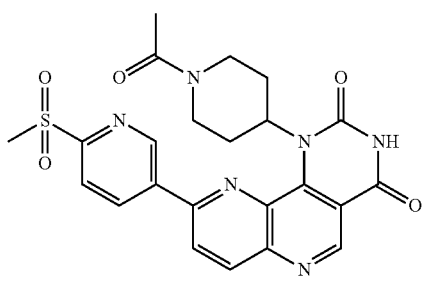
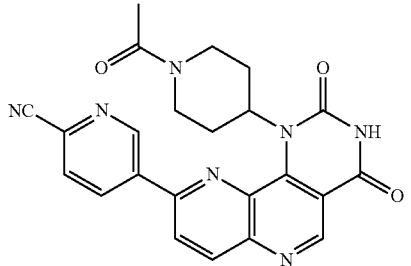
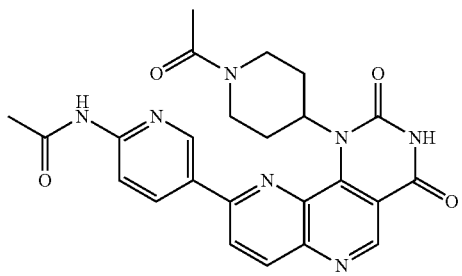
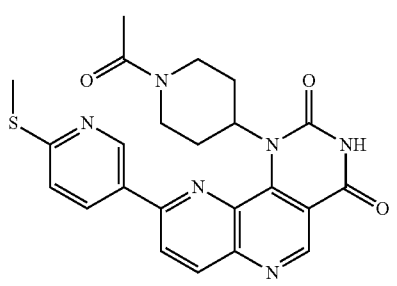
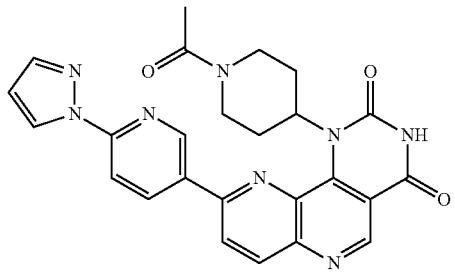
146
-continued
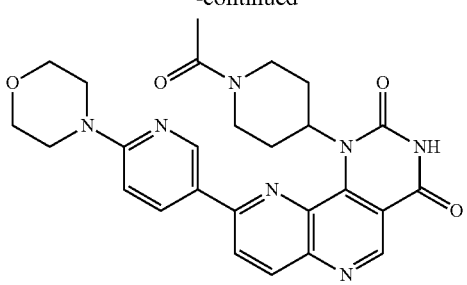
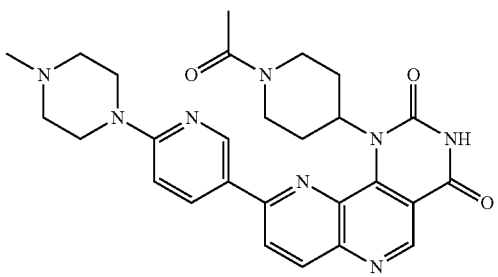
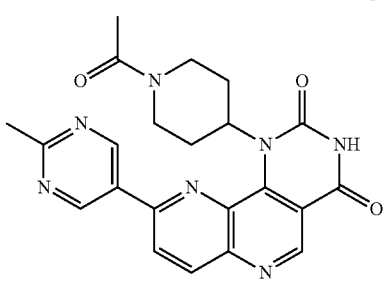
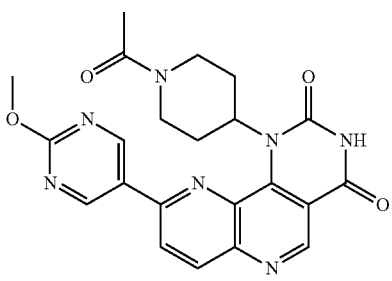
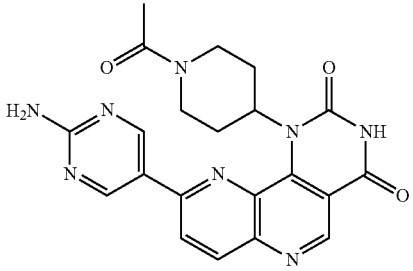
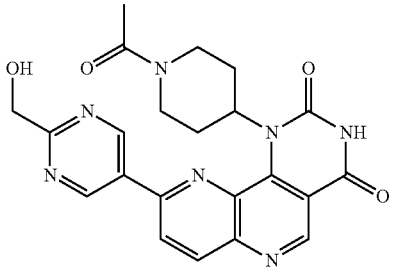

147
-continued
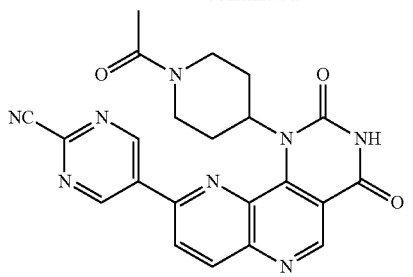
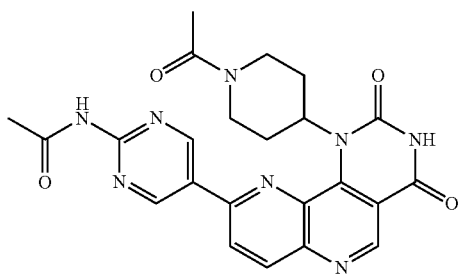
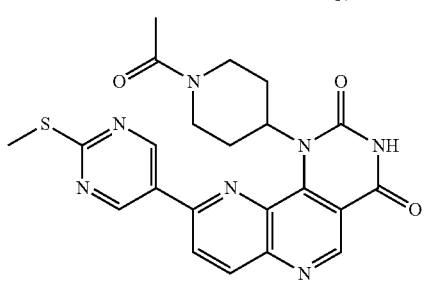
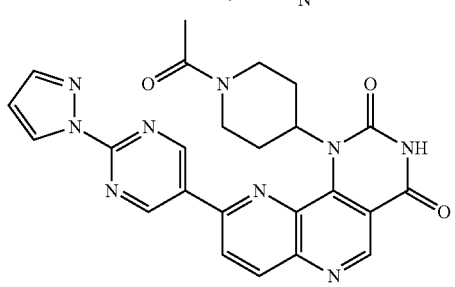
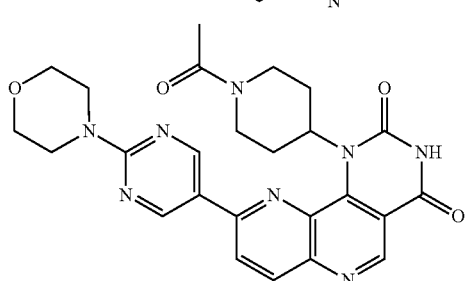
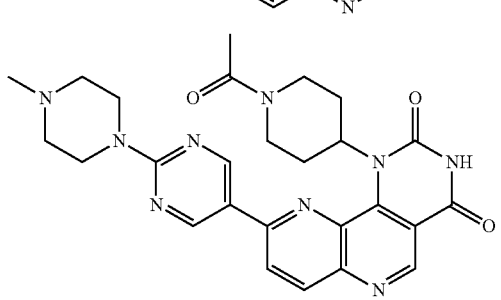
148
-continued
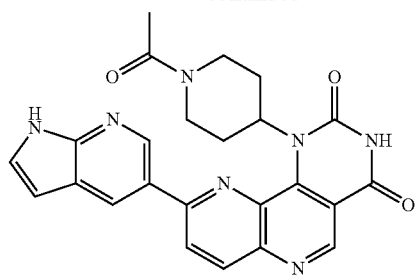
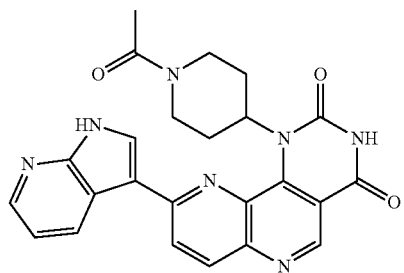
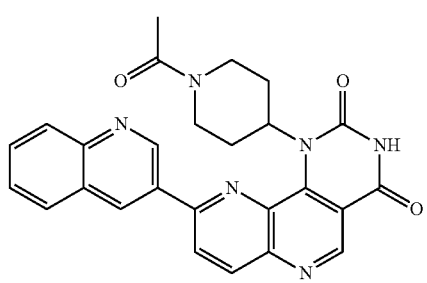
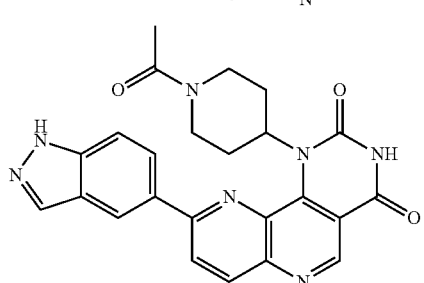
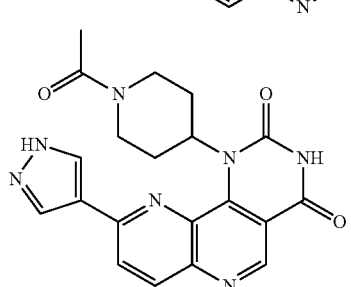
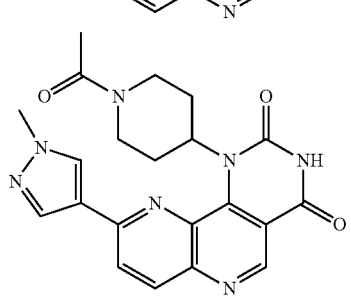

149
-continued
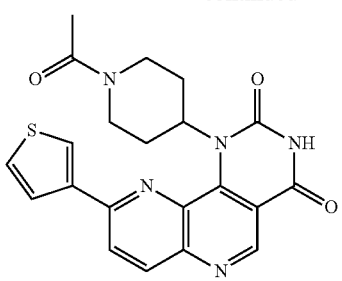
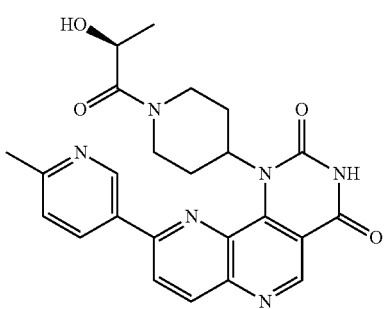
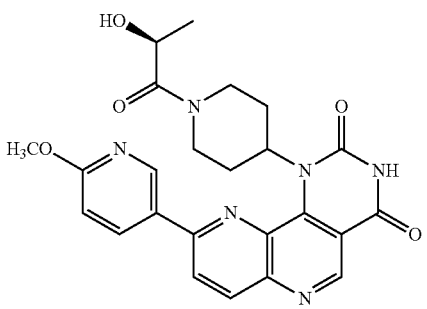
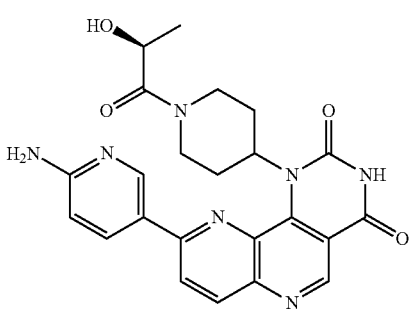
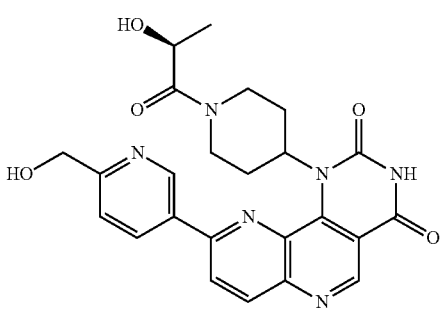
150
-continued
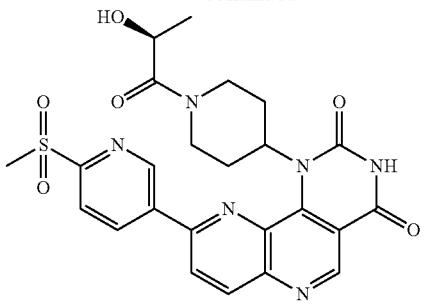
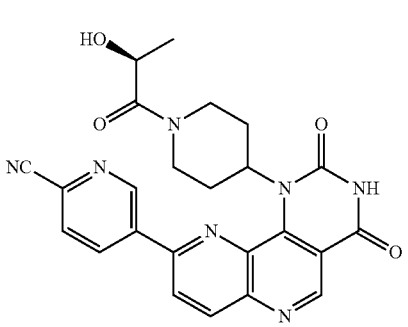
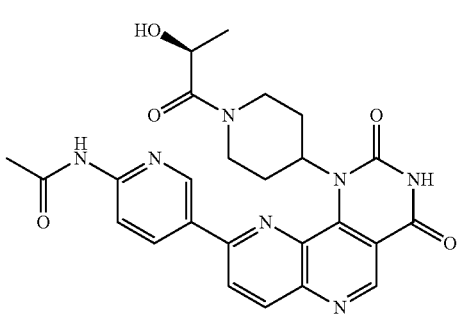
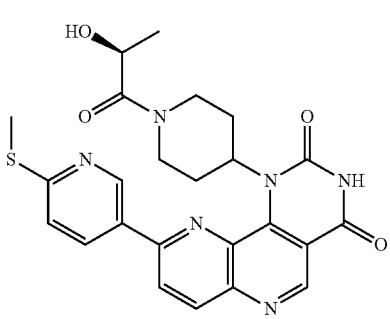
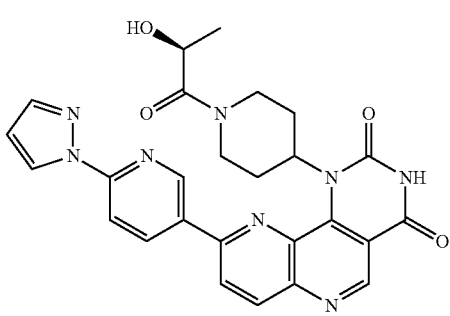

151
-continued
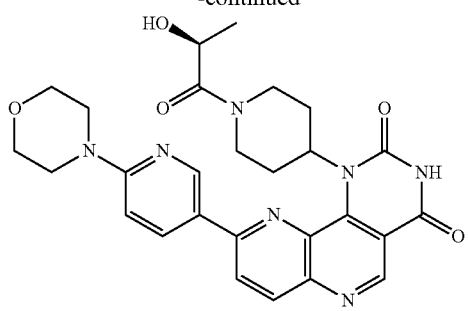
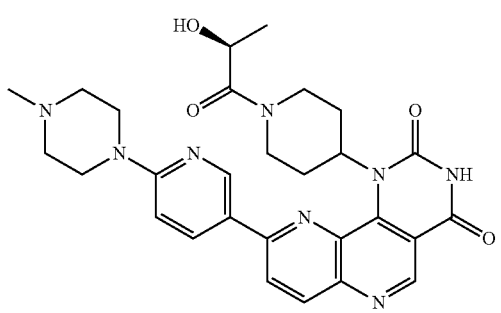
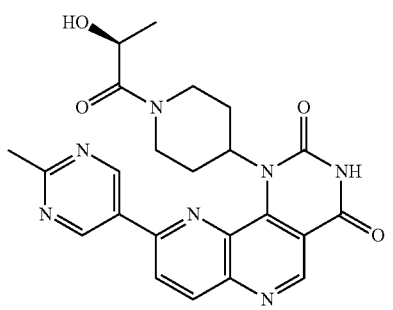
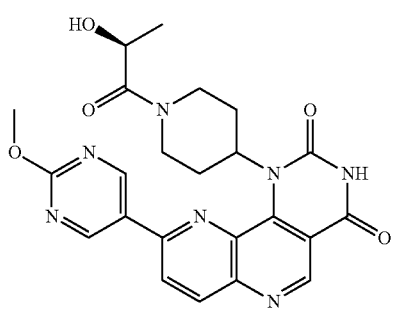
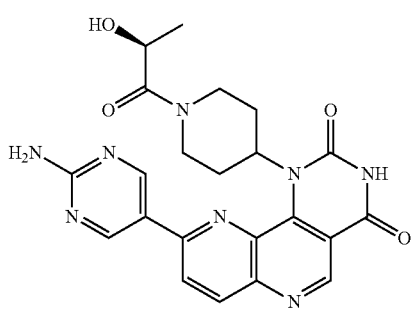
152
-continued
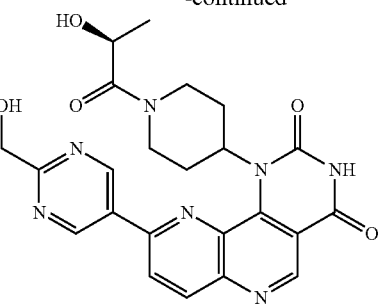
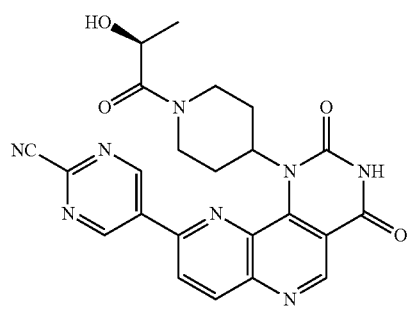
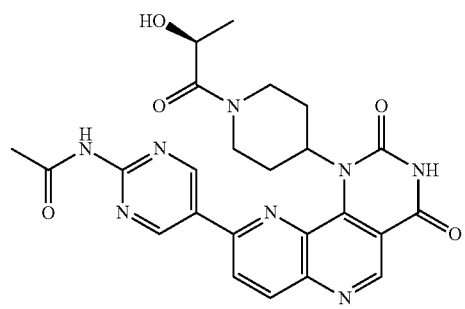
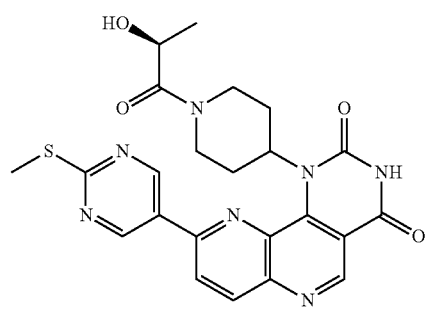
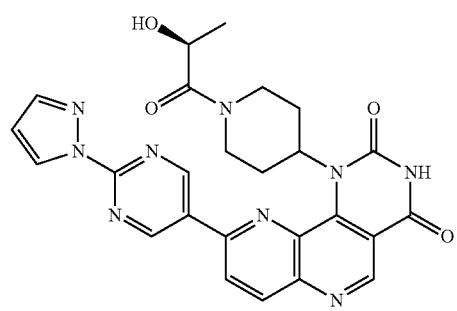

153
-continued
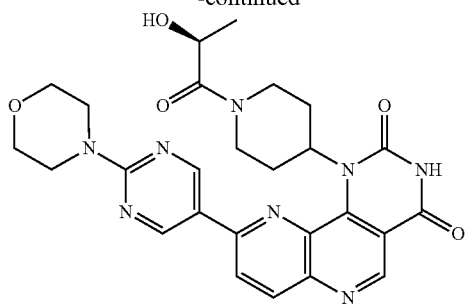
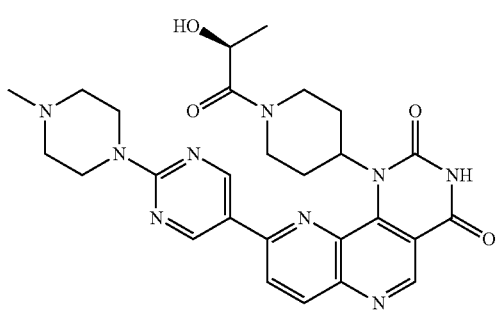
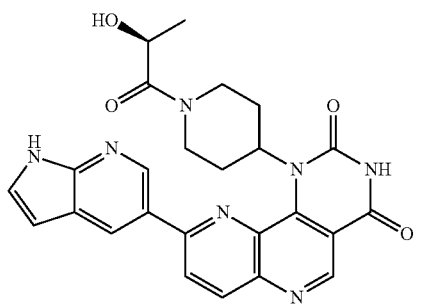 [SMILES: C[C@H](O)C(=O)N1CCC(n2c(=O)[nH]c(=O)c3cnc4ccc(-c5cnc6[nH]ccc6c5)nc4c32)CC1]
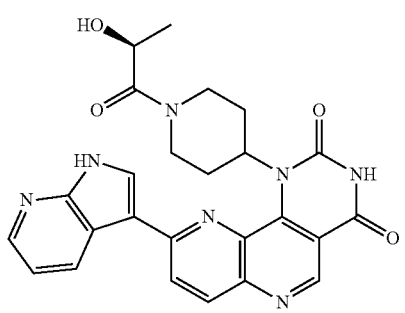 [SMILES: C[C@H](O)C(=O)N1CCC(n2c(=O)[nH]c(=O)c3cnc4ccc(-c5c[nH]c6ncccc56)nc4c32)CC1]
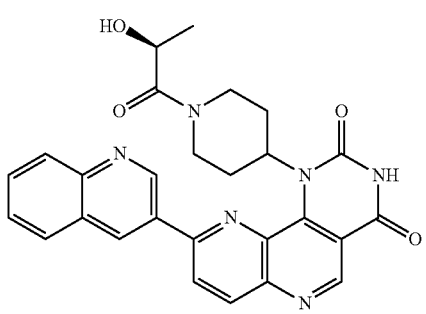 [SMILES: C[C@H](O)C(=O)N1CCC(n2c(=O)[nH]c(=O)c3cnc4ccc(-c5cnc6ccccc6c5)nc4c32)CC1]
154
-continued
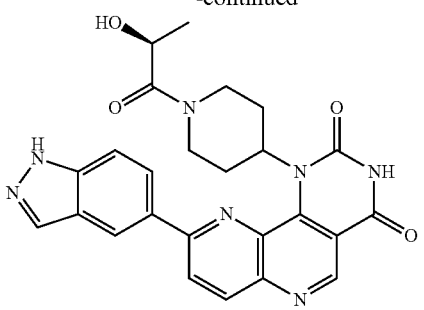
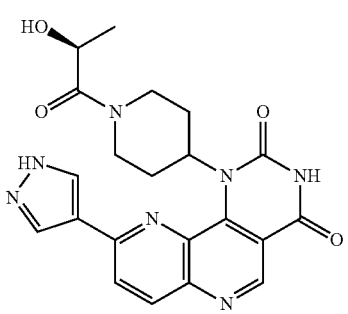 [SMILES: C[C@H](O)C(=O)N1CCC(n2c(=O)[nH]c(=O)c3cnc4ccc(-c5cn[nH]c5)nc4c32)CC1]
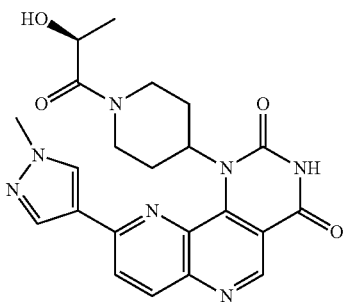
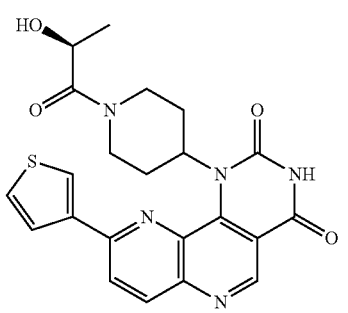 [SMILES: C[C@H](O)C(=O)N1CCC(n2c(=O)[nH]c(=O)c3cnc4ccc(-c5ccsc5)nc4c32)CC1]
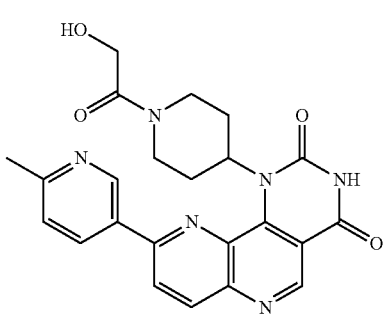 [SMILES: Cc1ccc(-c2ccc3ncc4c(=O)[nH]c(=O)n(C5CCN(C(=O)CO)CC5)c4c3n2)cn1]

155
-continued
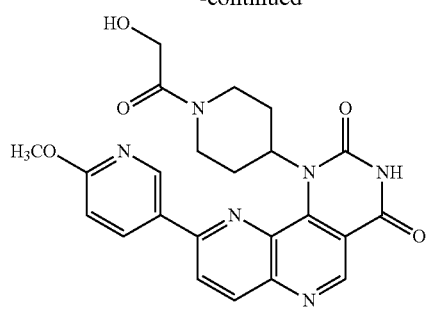
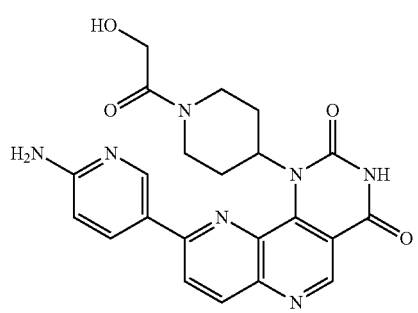
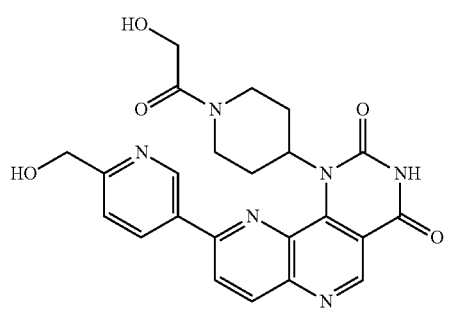 [SMILES: O=C(CO)N1CCC(n2c(=O)[nH]c(=O)c3cnc4ccc(-c5ccc(CO)nc5)nc4c32)CC1]
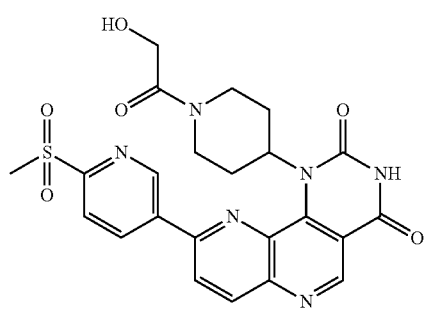 [SMILES: CS(=O)(=O)c1ccc(-c2ccc3ncc4c(=O)[nH]c(=O)n(C5CCN(C(=O)CO)CC5)c4c3n2)cn1]
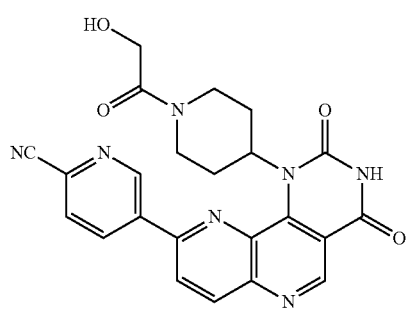
156
-continued
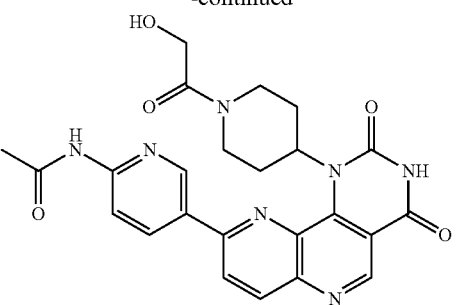
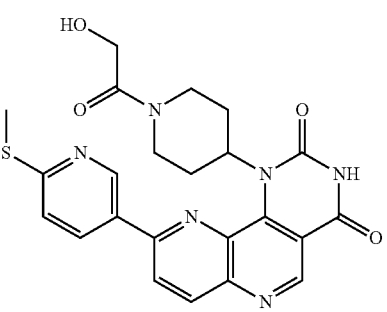 [SMILES: CSc1ccc(-c2ccc3ncc4c(=O)[nH]c(=O)n(C5CCN(C(=O)CO)CC5)c4c3n2)cn1]
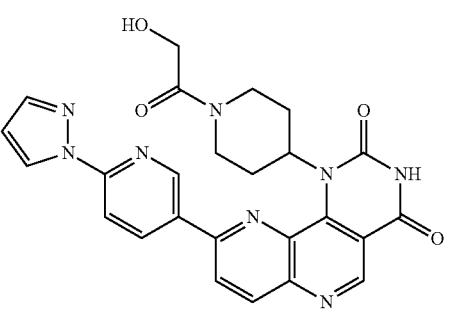
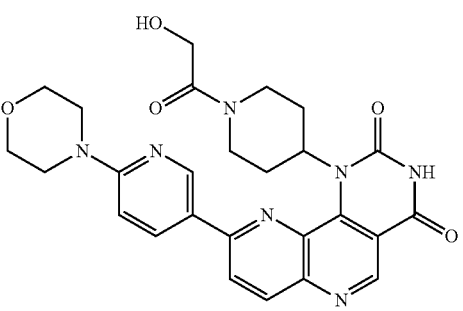
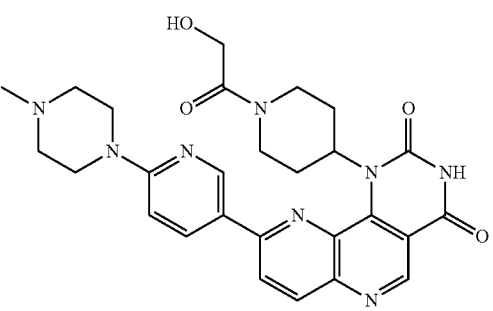

157
-continued
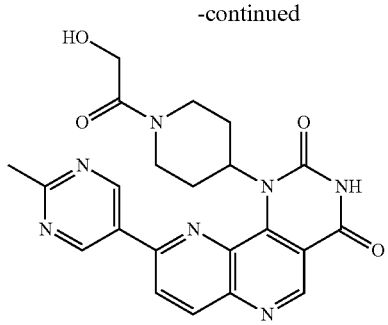
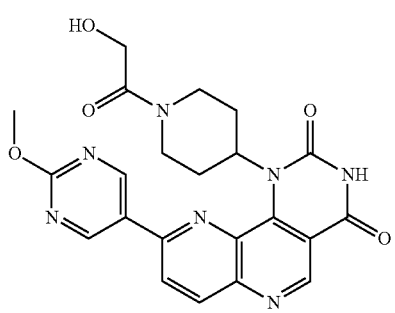
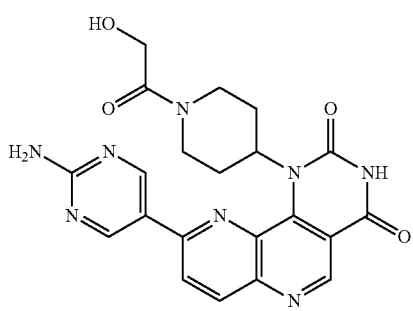
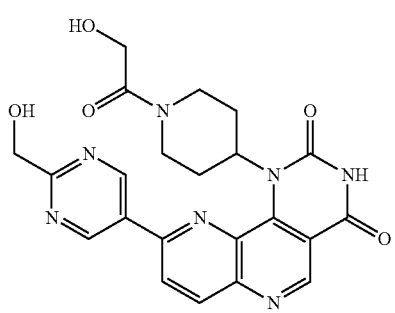 [SMILES: O=C(CO)N1CCC(n2c(=O)[nH]c(=O)c3cnc4ccc(-c5cnc(CO)nc5)nc4c32)CC1]
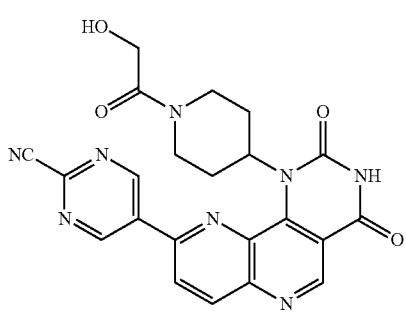 [SMILES: N#Cc1ncc(-c2ccc3ncc4c(=O)[nH]c(=O)n(C5CCN(C(=O)CO)CC5)c4c3n2)cn1]
158
-continued
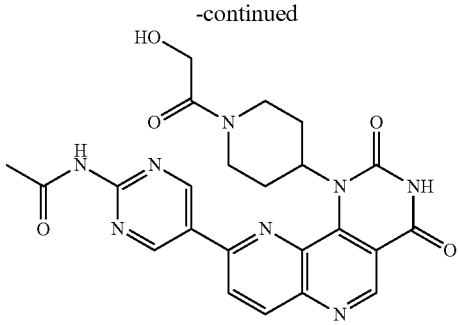
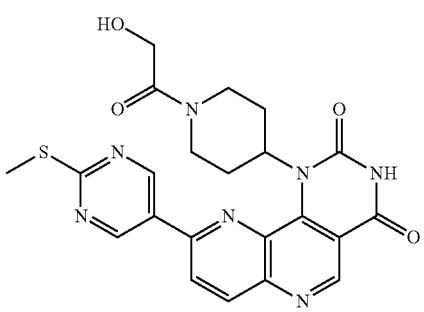
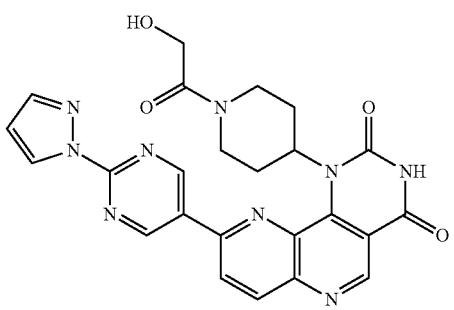 [SMILES: O=C(CO)N1CCC(n2c(=O)[nH]c(=O)c3cnc4ccc(-c5cnc(-n6cccn6)nc5)nc4c32)CC1]
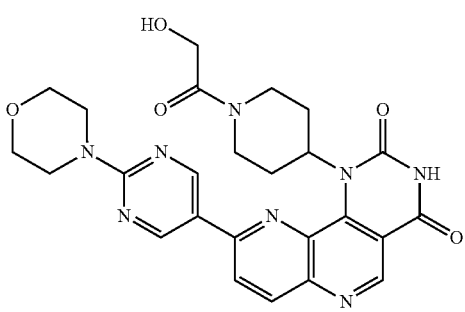
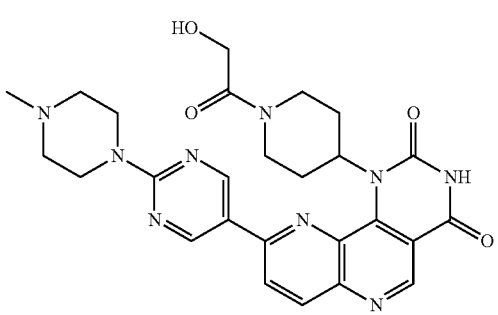

-continued
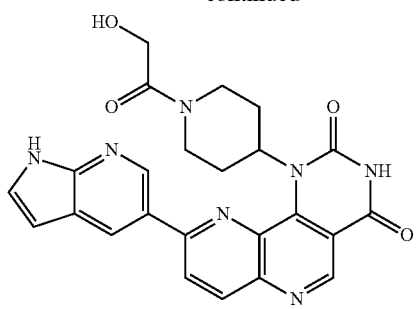
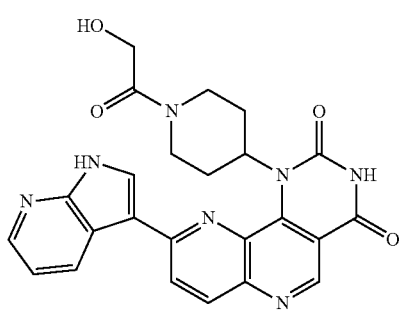 [SMILES: O=C(CO)N1CCC(n2c(=O)[nH]c(=O)c3cnc4ccc(-c5c[nH]c6ncccc56)nc4c32)CC1]
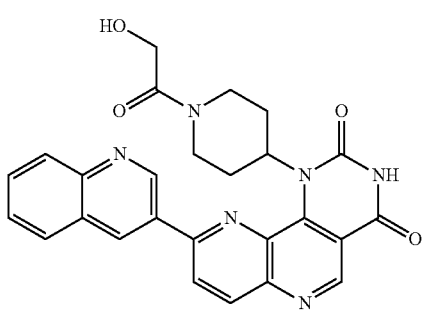 [SMILES: O=C(CO)N1CCC(n2c(=O)[nH]c(=O)c3cnc4ccc(-c5cnc6ccccc6c5)nc4c32)CC1]
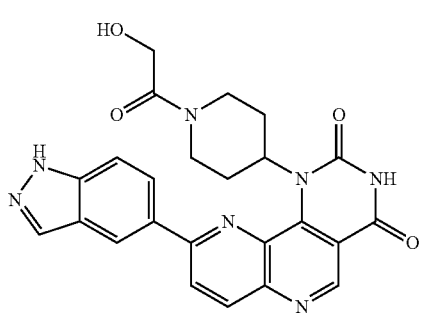 [SMILES: O=C(CO)N1CCC(n2c(=O)[nH]c(=O)c3cnc4ccc(-c5ccc6[nH]ncc6c5)nc4c32)CC1]
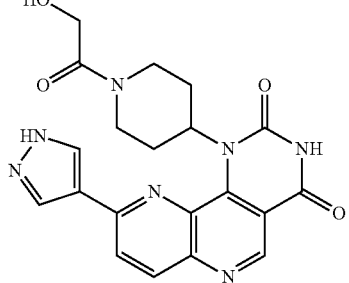
-continued
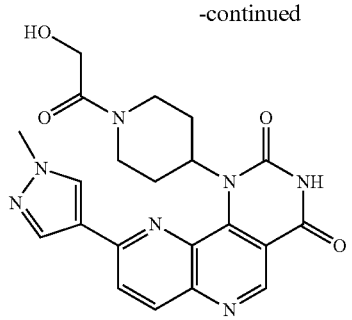
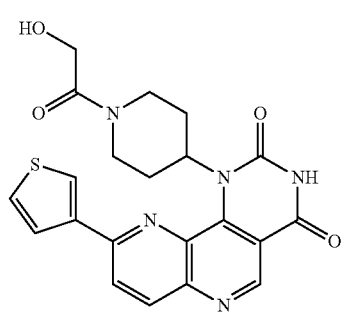 [SMILES: O=C(CO)N1CCC(n2c(=O)[nH]c(=O)c3cnc4ccc(-c5ccsc5)nc4c32)CC1]
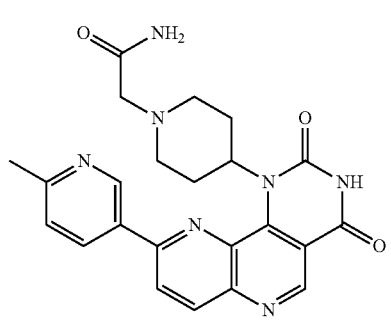 [SMILES: Cc1ccc(-c2ccc3ncc4c(=O)[nH]c(=O)n(C5CCN(CC(N)=O)CC5)c4c3n2)cn1]
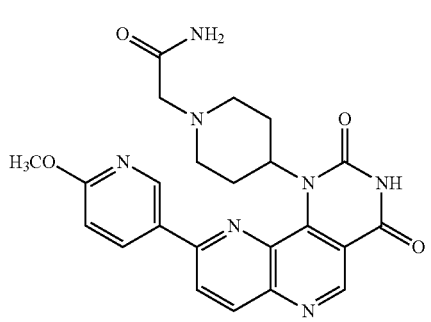
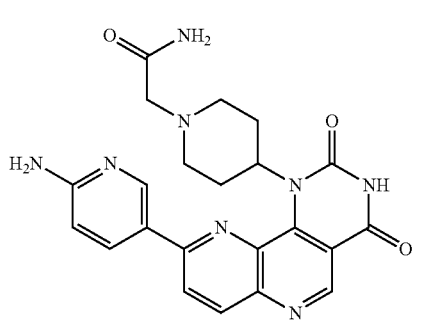 [SMILES: NC(=O)CN1CCC(n2c(=O)[nH]c(=O)c3cnc4ccc(-c5ccc(N)nc5)nc4c32)CC1]

161
-continued
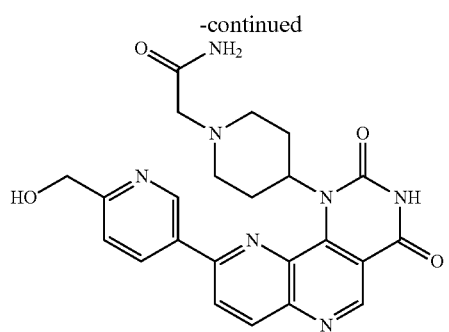
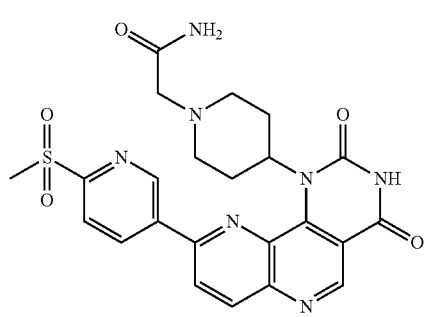 [SMILES: CS(=O)(=O)c1ccc(-c2ccc3ncc4c(=O)[nH]c(=O)n(C5CCN(CC(N)=O)CC5)c4c3n2)cn1]
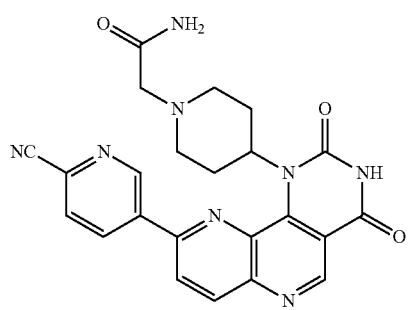 [SMILES: N#Cc1ccc(-c2ccc3ncc4c(=O)[nH]c(=O)n(C5CCN(CC(N)=O)CC5)c4c3n2)cn1]
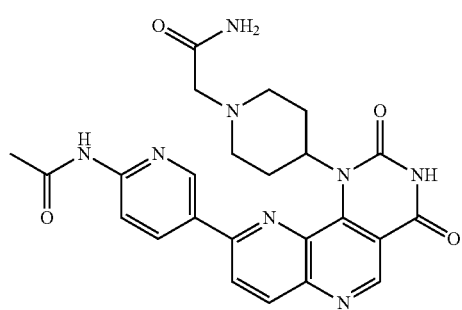 [SMILES: CC(=O)Nc1ccc(-c2ccc3ncc4c(=O)[nH]c(=O)n(C5CCN(CC(N)=O)CC5)c4c3n2)cn1]
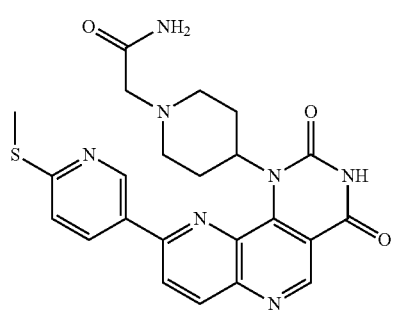 [SMILES: CSc1ccc(-c2ccc3ncc4c(=O)[nH]c(=O)n(C5CCN(CC(N)=O)CC5)c4c3n2)cn1]
162
-continued
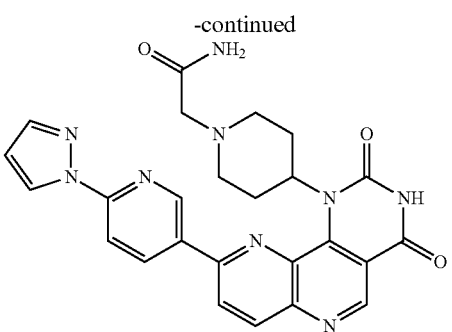
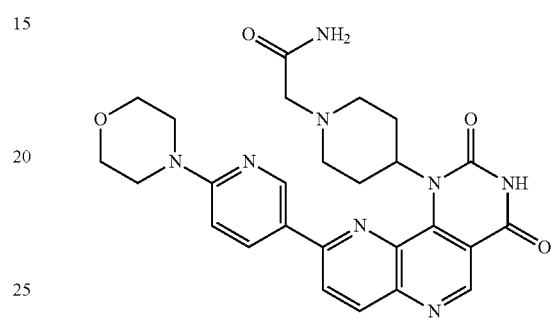
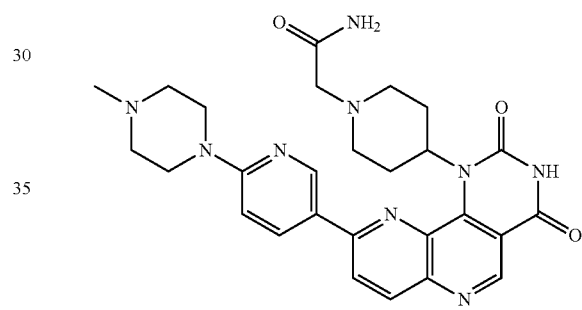
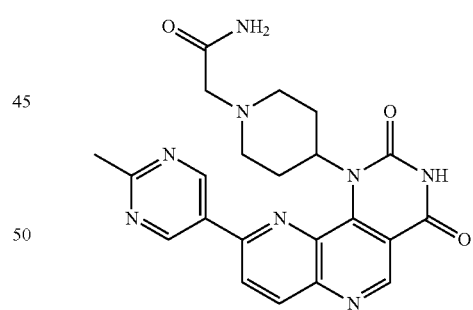
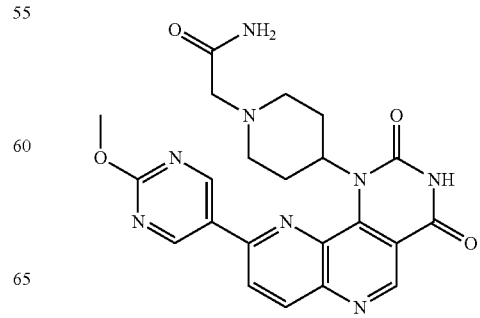

163
-continued
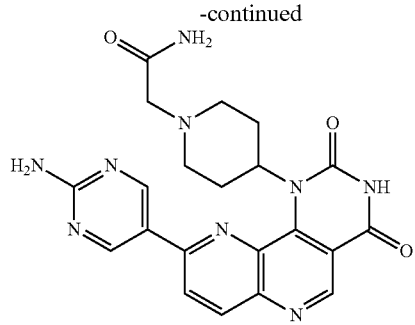
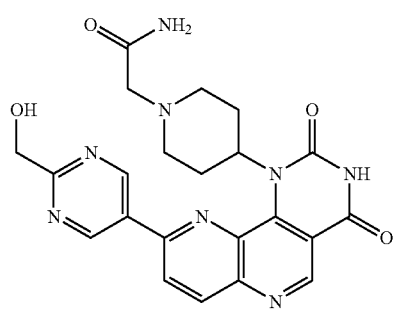 [SMILES: NC(=O)CN1CCC(n2c(=O)[nH]c(=O)c3cnc4ccc(-c5cnc(CO)nc5)nc4c32)CC1]
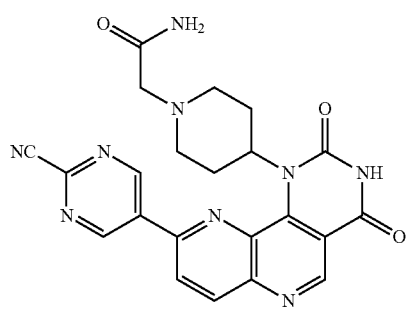
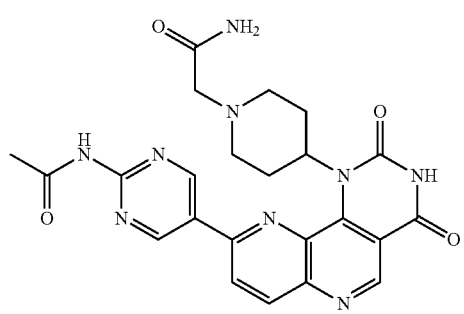 [SMILES: CC(=O)Nc1ncc(-c2ccc3ncc4c(=O)[nH]c(=O)n(C5CCN(CC(N)=O)CC5)c4c3n2)cn1]
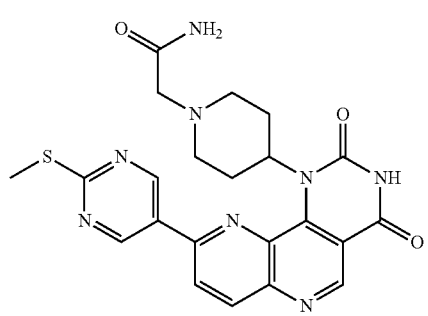 [SMILES: CSc1ncc(-c2ccc3ncc4c(=O)[nH]c(=O)n(C5CCN(CC(N)=O)CC5)c4c3n2)cn1]
164
-continued
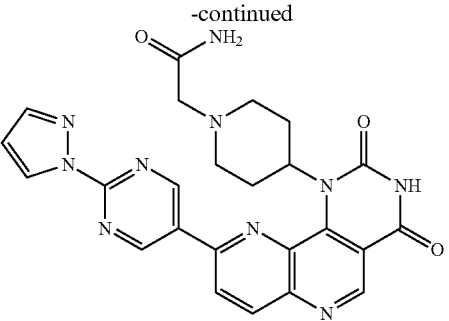
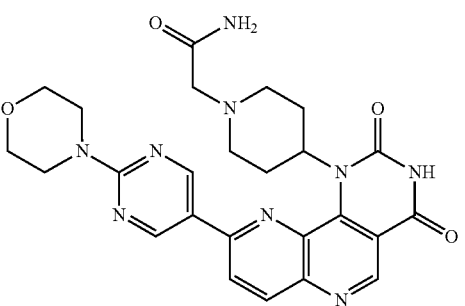 [SMILES: NC(=O)CN1CCC(n2c(=O)[nH]c(=O)c3cnc4ccc(-c5cnc(N6CCOCC6)nc5)nc4c32)CC1]
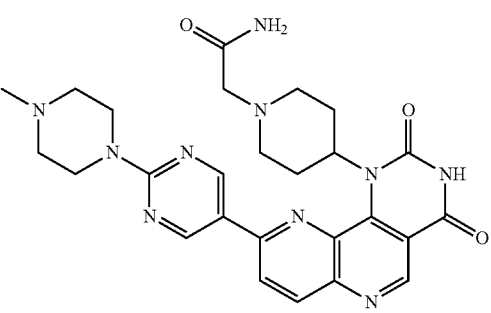
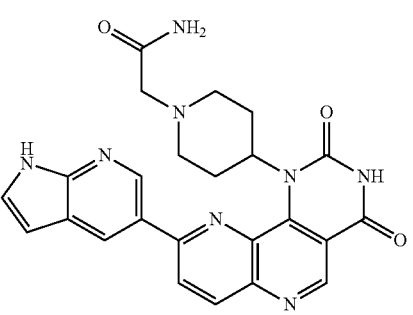 [SMILES: NC(=O)CN1CCC(n2c(=O)[nH]c(=O)c3cnc4ccc(-c5cnc6[nH]ccc6c5)nc4c32)CC1]
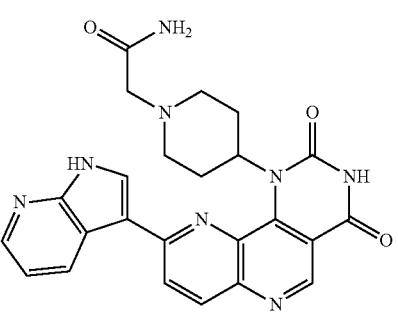 [SMILES: NC(=O)CN1CCC(n2c(=O)[nH]c(=O)c3cnc4ccc(-c5c[nH]c6ncccc56)nc4c32)CC1]

165
-continued
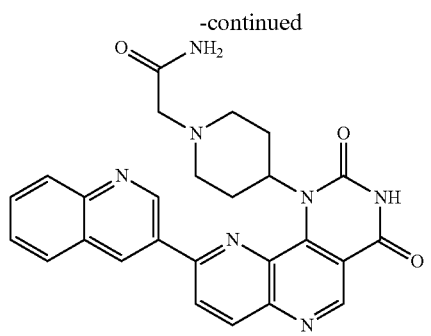
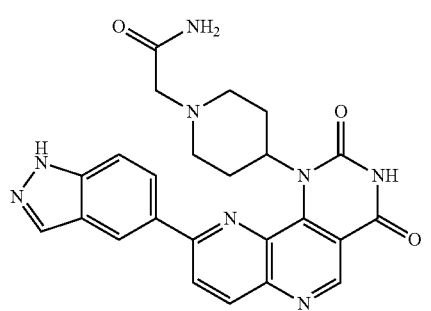 [SMILES: NC(=O)CN1CCC(n2c(=O)[nH]c(=O)c3cnc4ccc(-c5ccc6[nH]ncc6c5)nc4c32)CC1]
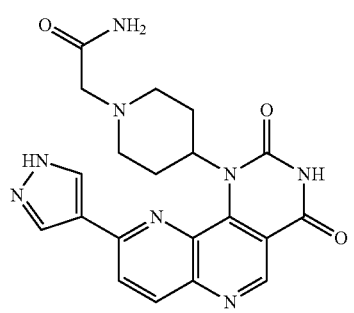 [SMILES: NC(=O)CN1CCC(n2c(=O)[nH]c(=O)c3cnc4ccc(-c5cn[nH]c5)nc4c32)CC1]
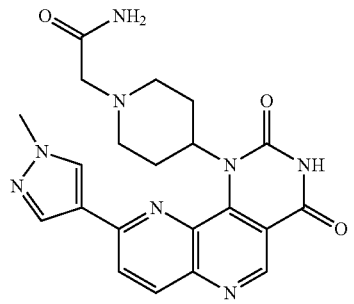 [SMILES: Cn1cc(-c2ccc3ncc4c(=O)[nH]c(=O)n(C5CCN(CC(N)=O)CC5)c4c3n2)cn1]
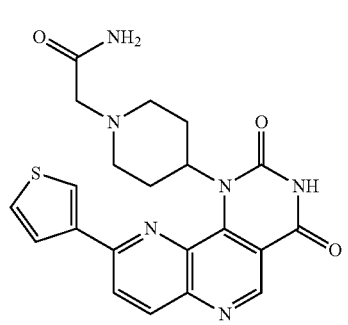 [SMILES: NC(=O)CN1CCC(n2c(=O)[nH]c(=O)c3cnc4ccc(-c5ccsc5)nc4c32)CC1]
166
-continued
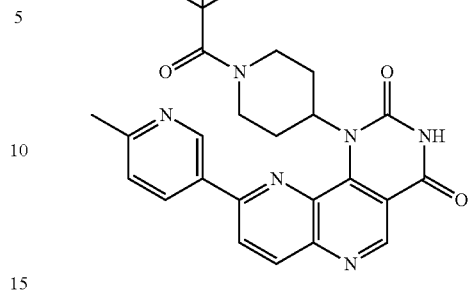
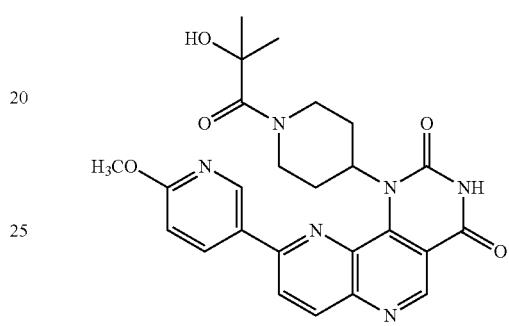
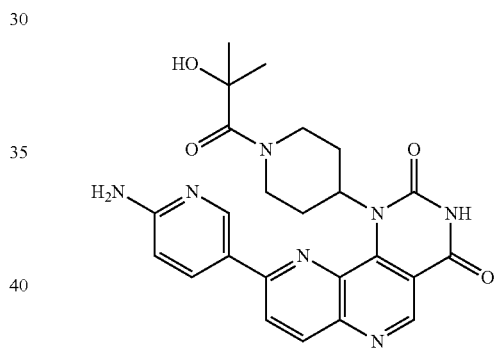
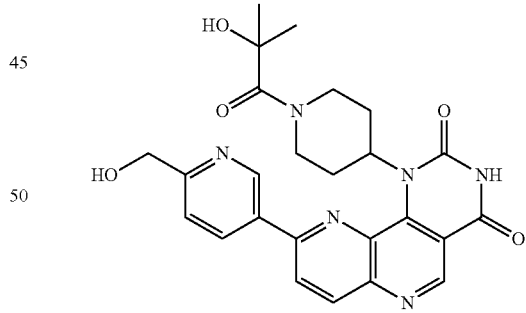
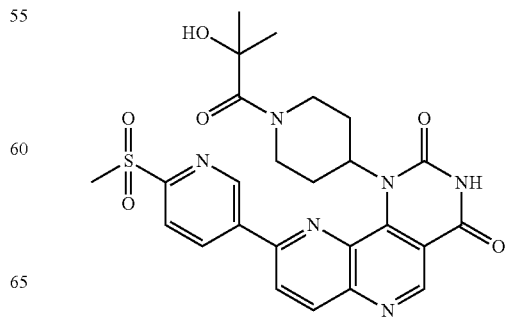

167
-continued
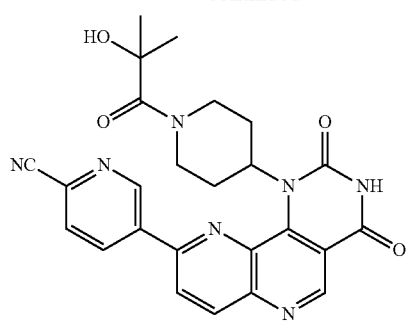 [SMILES: CC(C)(O)C(=O)N1CCC(n2c(=O)[nH]c(=O)c3cnc4ccc(-c5ccc(C#N)nc5)nc4c32)CC1]
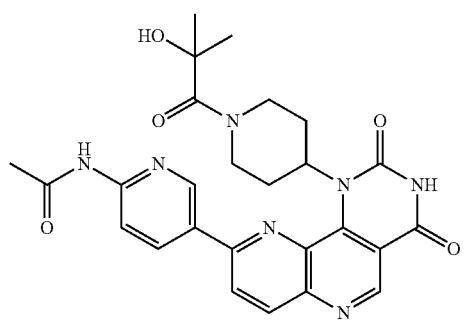 [SMILES: CC(=O)Nc1ccc(-c2ccc3ncc4c(=O)[nH]c(=O)n(C5CCN(C(=O)C(C)(C)O)CC5)c4c3n2)cn1]
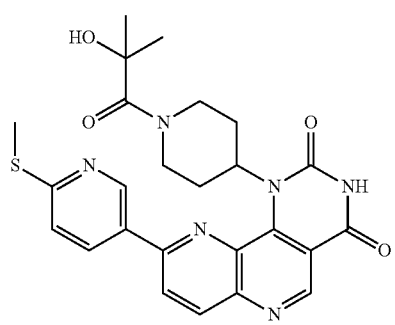 [SMILES: CSc1ccc(-c2ccc3ncc4c(=O)[nH]c(=O)n(C5CCN(C(=O)C(C)(C)O)CC5)c4c3n2)cn1]
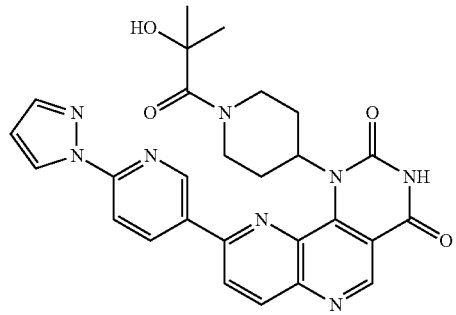 [SMILES: CC(C)(O)C(=O)N1CCC(n2c(=O)[nH]c(=O)c3cnc4ccc(-c5ccc(-n6cccn6)nc5)nc4c32)CC1]
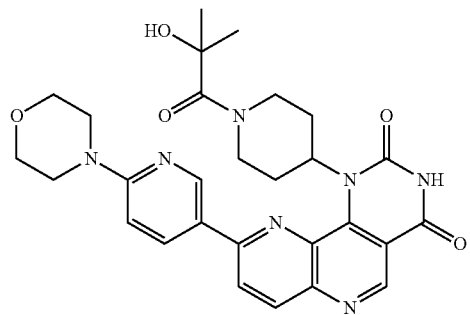 [SMILES: CC(C)(O)C(=O)N1CCC(n2c(=O)[nH]c(=O)c3cnc4ccc(-c5ccc(N6CCOCC6)nc5)nc4c32)CC1]
168
-continued
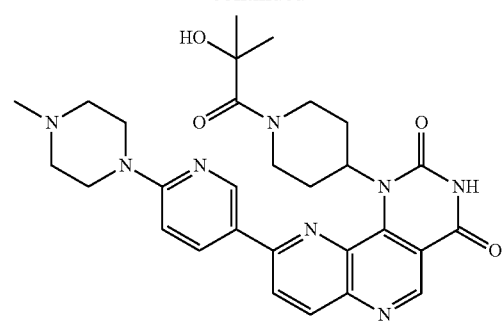 [SMILES: CN1CCN(c2ccc(-c3ccc4ncc5c(=O)[nH]c(=O)n(C6CCN(C(=O)C(C)(C)O)CC6)c5c4n3)cn2)CC1]
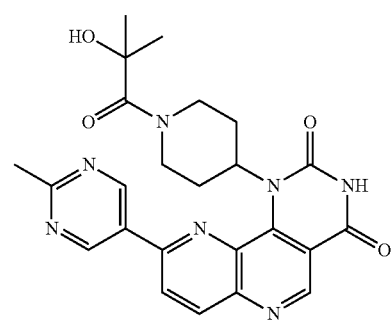 [SMILES: Cc1ncc(-c2ccc3ncc4c(=O)[nH]c(=O)n(C5CCN(C(=O)C(C)(C)O)CC5)c4c3n2)cn1]
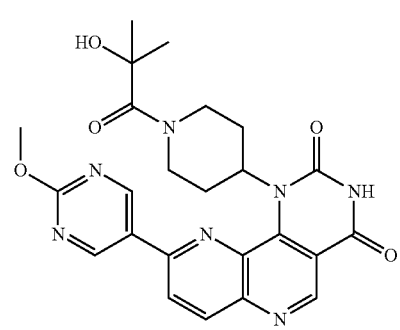 [SMILES: COc1ncc(-c2ccc3ncc4c(=O)[nH]c(=O)n(C5CCN(C(=O)C(C)(C)O)CC5)c4c3n2)cn1]
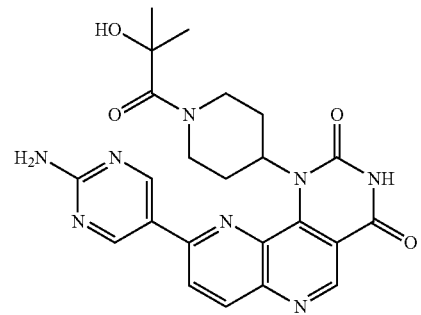
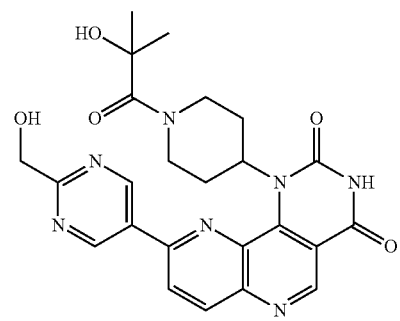 [SMILES: CC(C)(O)C(=O)N1CCC(n2c(=O)[nH]c(=O)c3cnc4ccc(-c5cnc(CO)nc5)nc4c32)CC1]

169
-continued
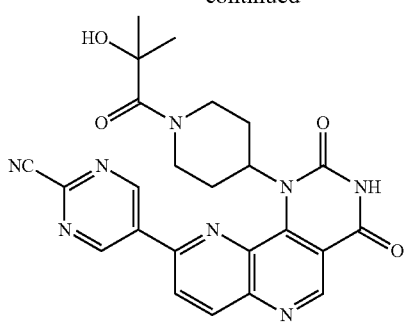
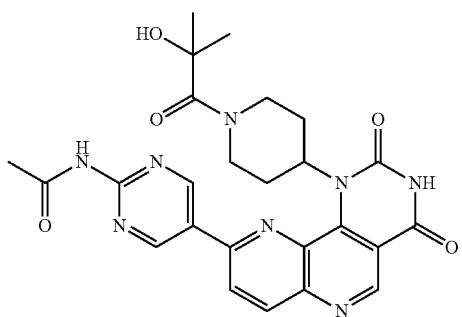 [SMILES: CC(=O)Nc1ncc(-c2ccc3ncc4c(=O)[nH]c(=O)n(C5CCN(C(=O)C(C)(C)O)CC5)c4c3n2)cn1]
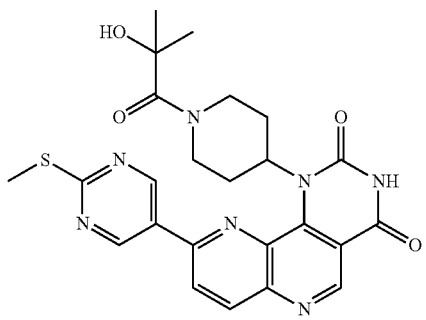 [SMILES: CSc1ncc(-c2ccc3ncc4c(=O)[nH]c(=O)n(C5CCN(C(=O)C(C)(C)O)CC5)c4c3n2)cn1]
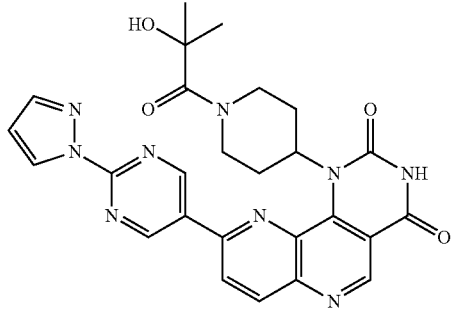
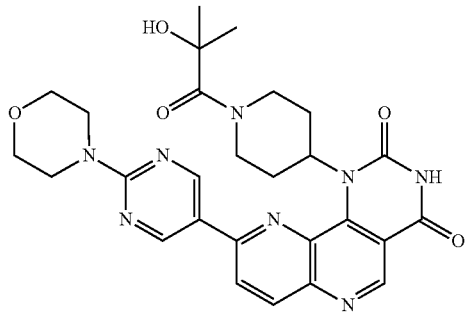 [SMILES: CC(C)(O)C(=O)N1CCC(n2c(=O)[nH]c(=O)c3cnc4ccc(-c5cnc(N6CCOCC6)nc5)nc4c32)CC1]
170
-continued
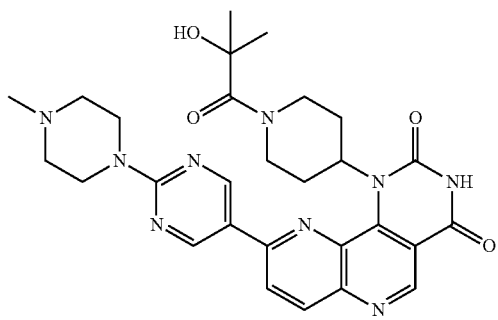 [SMILES: CN1CCN(c2ncc(-c3ccc4ncc5c(=O)[nH]c(=O)n(C6CCN(C(=O)C(C)(C)O)CC6)c5c4n3)cn2)CC1]
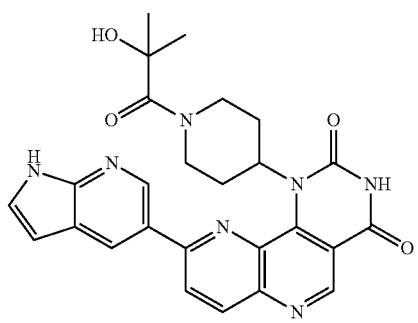 [SMILES: CC(C)(O)C(=O)N1CCC(n2c(=O)[nH]c(=O)c3cnc4ccc(-c5cnc6[nH]ccc6c5)nc4c32)CC1]
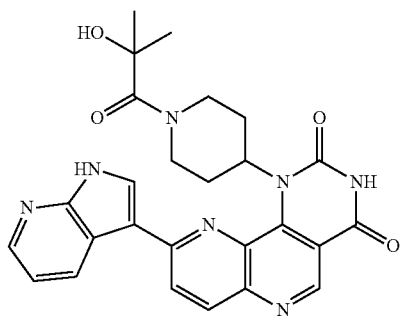 [SMILES: CC(C)(O)C(=O)N1CCC(n2c(=O)[nH]c(=O)c3cnc4ccc(-c5c[nH]c6ncccc56)nc4c32)CC1]
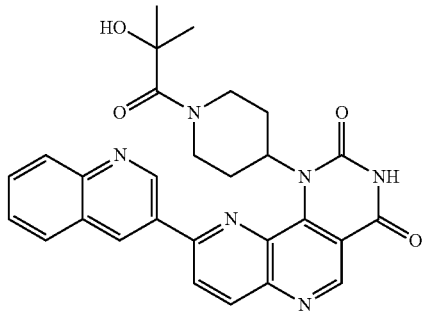 [SMILES: CC(C)(O)C(=O)N1CCC(n2c(=O)[nH]c(=O)c3cnc4ccc(-c5cnc6ccccc6c5)nc4c32)CC1]
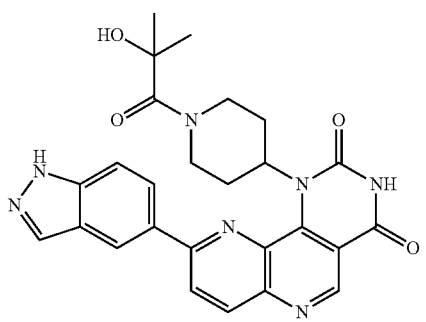 [SMILES: CC(C)(O)C(=O)N1CCC(n2c(=O)[nH]c(=O)c3cnc4ccc(-c5ccc6[nH]ncc6c5)nc4c32)CC1]

-continued

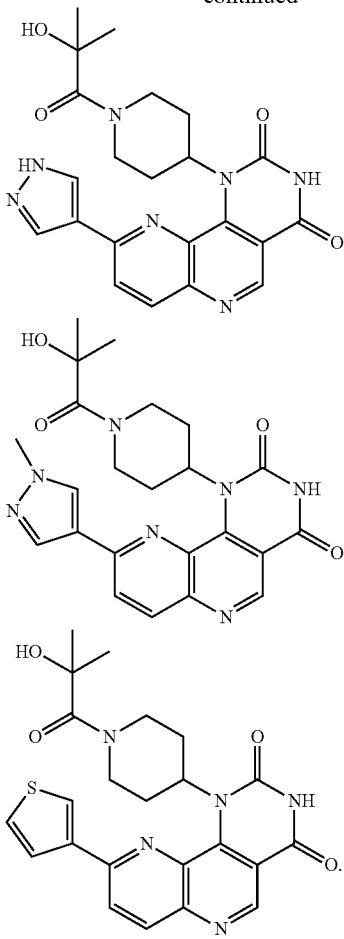

7. A pharmaceutical composition, containing the compound of claim 1, or a pharmaceutically acceptable salt or a stereoisomer thereof and one or more pharmaceutically acceptable carriers, and optionally further containing one or more antitumor agents and immunosuppressants, wherein the antitumor agents and immunosuppressive agents are
   (1) anti-metabolites selected from capecitabine, gemcitabine and pemetrexed disodium;
   (2) growth factor inhibitors selected from pazopanib, imatinib, erlotinib, lapatinib, gefitinib and vandetanib;
   (3) antibodies selected from Herceptin and Avastin;
   (4) mitotic inhibitors selected from paclitaxel, vinorelbine, docetaxel and doxorubicin;
   (5) anti-tumor hormones selected from letrozole, tamoxifen, fulvestrant, flutamide and triptorelin;
   (6) alkylating agents selected from cyclophosphamide, nitrogen mustard, melphalan, chlorambucil and carmustine;
   (7) platinum metals selected from carboplatin, cisplatin and oxaliplatin;
   (8) topoisomerase inhibitors selected from camptothecin, topotecan and irinotecan;
   (9) immunosuppressants selected from everolimus, sirolimus and temsirolimus;
   (10) purine analogues selected from 6-mercaptopurine, 6-thioguanine and azathioprine;
   (11) antibiotics selected from rhzomorph D, daunorubicin, doxorubicin, mitoxantrone, bleomycin and plicamycin; or
   (12) adrenal cortex inhibitor which is aminoglutethimide.

8. A method for treating proliferative diseases, which comprises administering to a patient a therapeutically effective amount of the compound of claim 1, or a pharmaceutically acceptable salt or a stereoisomer thereof.

9. The method of claim 8, wherein the proliferative diseases includes cancer and non-cancer diseases, wherein the cancer disease is selected from a brain tumor, lung cancer, non-small cell lung cancer, squamous cell carcinoma, bladder cancer, stomach cancer, ovarian cancer, peritoneal cancer, pancreatic cancer, breast cancer, head and neck cancer, cervical cancer, endometrial cancer, colorectal cancer, liver cancer, kidney cancer, esophageal adenocarcinoma, esophageal squamous cell carcinoma, solid tumors, non-Hodgkin's lymphoma, glioma, glioblastoma multiforme, glio sarcoma, prostate cancer, thyroid carcinoma, genital tract carcinoma, carcinoma in situ, lymphoma, histiocytic lymphoma, neurofibromatosis, bone cancer, skin cancer, colon cancer, testicular cancer, small cell lung cancer, gastrointestinal stromal tumor, prostate tumor, mast cell tumor, multiple myeloma, melanoma, glioma glioblastoma, astrocytoma, neuroblastoma, sarcomas; and the non-cancer disease is selected from a skin disease or benign prostate hyperplasia.

* * * * *